United States Patent [19]

Hibino et al.

[11] Patent Number: 4,860,094

[45] Date of Patent: Aug. 22, 1989

[54] CONTROL APPARATUS FOR USE WITH DIFFERENT TYPES OF ENDOSCOPES

[75] Inventors: Hiroki Hibino, Hachioji; Toshiaki Nishikori, Sagamihara; Kenji Kumura, Tachikawa, all of Japan

[73] Assignee: Olympus Optical Co., Ltd., Tokyo, Japan

[21] Appl. No.: 168,085

[22] Filed: Mar. 9, 1988

[30] Foreign Application Priority Data

| Mar. 10, 1987 | [JP] | Japan | 52-54591 |
| Mar. 10, 1987 | [JP] | Japan | 52-54592 |
| Mar. 16, 1987 | [JP] | Japan | 52-60291 |
| Mar. 16, 1987 | [JP] | Japan | 52-60292 |
| Mar. 17, 1987 | [JP] | Japan | 52-61682 |

[51] Int. Cl.$^4$ .......................... H04N 7/18; A61B 1/04
[52] U.S. Cl. ....................................... 358/98; 358/93; 128/6
[58] Field of Search ............. 358/98, 93; 128/4-6

[56] References Cited

U.S. PATENT DOCUMENTS

| 4,327,738 | 5/1982 | Green et al. ................. 358/98 X |
| 4,491,865 | 1/1985 | Danna et al. |

FOREIGN PATENT DOCUMENTS

| 51-65962 | 6/1976 | Japan . |
| 56-3033 | 1/1981 | Japan . |
| 0195818 | 11/1983 | Japan .................. 358/98 |
| 60-76888 | 5/1985 | Japan . |
| 60-243625 | 12/1985 | Japan . |
| 61-82731 | 4/1986 | Japan . |

Primary Examiner—James J. Groody
Assistant Examiner—Victor R. Kostak
Attorney, Agent, or Firm—Armstrong, Nikaido, Marmelstein, Kubovcik & Murray

[57] ABSTRACT

This endoscope apparatus is provided with a plurality of kinds of endoscopes each having an elongate insertable part having an illuminating window and observing window in the tip part. An illuminating light transmitting system leads an illuminating light to the illuminating window. An imaging apparatus receives the returning light from an object entering from the observing window and imaging the object. A signal transmitting system is connected at one end to the imaging apparatus. An illumination connector is provided at the entrance side end of the illuminating light transmitting system and is different in at least one of the illuminating method and signal processing system. The endoscope apparatus is further provided with an illuminating apparatus having an illumination connector receptacle removably connectable with respective illumination connectors of the plurality of endoscopes and feeding illuminating light to the plurality of endoscopes. A signal processing apparatus has a signal connector receptacle removably connectable with respective signal connectors of the plurality of endoscopes and processing signals for the plurality of endoscopes. At least one of the illumination connector receptacle and signal connector receptacle is plural.

34 Claims, 44 Drawing Sheets

FIG.9(A)  FIG.9(B)
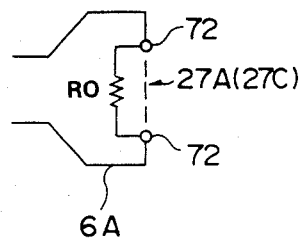
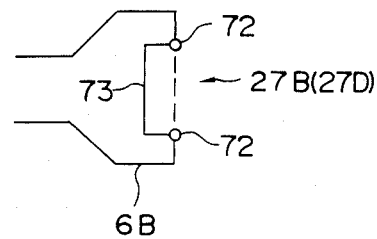
FIG.10(A)  FIG.10(B)
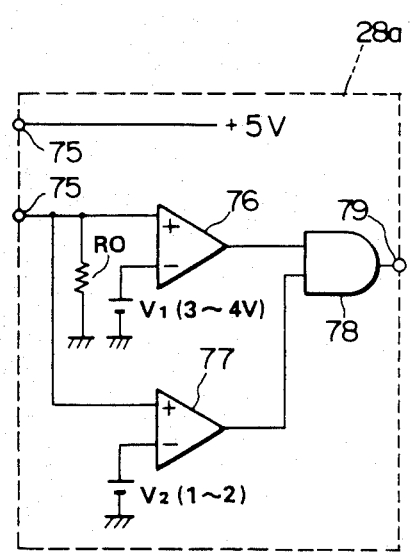
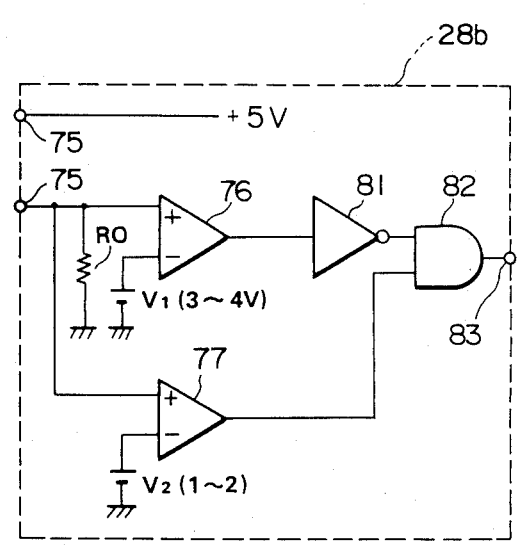

CONTROL APPARATUS FOR USE WITH DIFFERENT TYPES OF ENDOSCOPES

BACKGROUND OF THE INVENTION

1. Field of the Invention

This invention relates to an endoscope apparatus wherein a plurality of kinds of endoscopes different in the illuminating method and imaging system can be used.

2. Related Art Statement

Recently, there is extensively used an endoscope (called a scope or fiber scope)m whereby an organ or the like within a body cavity can be observed by inserting an elongate insertable part into the body cavity and any curing treatment can be made by using, as required, a treating tool inserted through a treating tool channel.

Also, there are suggested various electronic scopes wherein a solid state imaging such as a charge coupled device (CCD) is used for the imaging means. As compared with the fiber scope, an electronic scope has advantages because the resolution is higher, it is easier to record and reproduce picture images and picture image treatments such as the enlargement of picture images and the comparison of two picture images are easier.

Along the color picture image imaging systems of the above mentioned electronic scope, there are a field sequential system wherein the illuminating light is switched sequentially to R (red), G (green) and B (blue) as shown, for example, in the gazette of a Japanese patent laid open No. 82731/1986 and a synchronous system (also called a color mosaic system) wherein a filter array in which color filters transmitting respectively colors such as R, G and B are arranged in the form of a mosaic is provided on the front surface of a solid state imaging device as shown, for example, in the gazette of a Japanese patent laid open No. 76888/1985. The field sequential system has an advantage because that the size can be made smaller than in the synchronous system. On the other hand, the synchronous system has an advantage because that no color is displaced.

There are many kinds of the above mentioned electronic scopes depending on the use thereof. For example, an electronic scope in which the outside diameter of the insertable part is about 10 mm is used for the upper or lower digestive organ. On the other hand, for example, an electronic scope in which the outside diameter of the insertable part is about 5 mm is necessary for the bronchus. It is physically and functionally unreasonable to use the same kind of imaging device and the same kind of imaging system for various electronic scopes in which the outside diameters of the insertable parts are over a wide range. For example, in order to realize an electronic scope for the bronchus (small diameter), an imaging device of a small number of pixels can not help being used.

In case the number of pixels is small, in order to prevent the reduction of the resolution, the field sequential type color imaging system whereby an object is field sequentially illuminated with lights of respective wavelengths of R, G and B and is field-sequentially imaged under these illuminations and the images are combined and color-displayed is more advantageous than the synchronous type imaging system wherein a color mosaic filter is used.

On the other hand, for the outside diameter of about 10 mm of the insertable part, it is advantageous in improving the picture quality to increase the number of pixels and to synchronize the imaging system.

Now, the above mentioned fiber scope or electronic scope is used generally as connected to a light source apparatus feeding an illuminating light adapted to each scope and a video processor processing video signals.

In the above mentioned fiber scope, field sequential type electronic scope and synchronous type electronic scope, the illuminating method and signal processing are different. The conventional video processor corresponds to either of the field sequential type or synchronous type. Therefore, the user has to prepare respectively different video processors and make different operations depending on the kind of scope, which is low in economy and efficiency.

In the gazette of a Japanese patent laid open No. 243625/1985, there is disclosed a connecting system whereby a fiber scope, provided with an optical fiber bundle for transmitting images, is connected to a controlling apparatus of a field sequential type electronic scope so that the image may be observed on the displaying picture surface of a monitor television or the like. However, in this system, a scope provided with a synchronous type imaging means can not be used.

Thus, in the prior art, a plurality of kinds of endoscopes different in the illuminating method and imaging system could not be used in a common video processor. This is not limited to the above described field sequential type and synchronous type. For example, a scope for observing an object in a visible ray range and a scope for observing an object in an infrared ray range can not be used in a common video processor.

OBJECTS AND SUMMARY OF THE INVENTION

An object of the present invention is to provide an endoscope apparatus wherein a plurality of kinds of endoscopes different in at least one of the illuminating method and signal processing system can be used with a common control apparatus and the formation can be simplified.

Another object of the present invention is to provide an endoscope apparatus wherein an endoscopes provided with a field sequential type imaging means and an endoscope provided with a synchronous type imaging means can both be used with a common control apparatus and the formation can be simplified.

The endoscope apparatus of the present invention is provided with a plurality of kinds of endoscopes different in at least one of the illuminating method and signal processing system and each having an elongate insertable part having an illuminating window and observing window in the tip part, an illuminating light transmitting device means leading an illuminating light to the above mentioned illuminating window, an imaging device imaging an object image by receiving the returning light from the object incident from the above mentioned observing window, and a signal transmitting device is connected. At one end to the above mentioned imaging device, an illuminating connector is provided at the entrance side end of the above mentioned illuminating light transmitting device and a signal connector is provided at the other end of the above mentioned signal transmitting device. The endoscope apparatus is further provided with an illuminating device having an illuminating connector receptacle removably connectable with each illuminating connector of the above mentioned plurality of kinds of endoscopes and feeding an illuminating light adapted to each of the above mentioned plurality of kinds of endoscopes and a signal processing device having a signal connector receptacle removably connectable with each signal connector of the above mentioned plurality of kinds of endoscopes and processing the signal for each of the above mentioned plurality of kinds of endoscopes. At least one of the above mentioned illuminating connector receptacle and the above mentioned signal connector receptacle is plural in response to the type of the endoscope.

The other features and advantages of the present invention will become apparent enough with the following explanation.

BRIEF DESCRIPTION OF THE DRAWINGS

FIGS. 1 to 11 relate to the first embodiment of the present invention.

FIG. 1 is a perspective view showing the entire system of an endoscope apparatus.

FIG. 2 is a block diagram showing the formation of an imaging apparatus body and field sequential type electronic scope.

FIG. 3 is an explanatory view showing the formation of a synchronous type electronic scope.

FIG. 4 is an explanatory view showing the formation of a fiber scope fitted with a field sequential type externally fitted camera.

FIG. 5 is an explanatory view showing the formation of a fiber scope fitted with a synchronous type externally fitted camera.

FIG. 6 is an explanatory view showing the formation of a fiber scope.

FIG. 7 is a block diagram showing the formation of a field sequential type process circuit.

FIG. 8 is a block diagram showing the formation of a synchronous type process circuit.

FIG. 9 (A) is an explanatory view showing the formation of a type signal generating circuit of a field sequential type scope.

FIG. 9 (B) is an explanatory view showing the formation of a type signal generating circuit of a synchronous type scope.

FIG. 10 (A) is a circuit diagram showing the formation of a discriminating circuit for a field sequential type scope.

FIG. 10 (B) is a circuit diagram showing the formation of a discriminating circuit for a synchronous type scope.

FIGS. 11 (A) and (B) are perspective views showing modifications of a connector and connector receptacle.

FIG. 12 is a block diagram showing the formation of an output circuit.

FIG. 13 is a circuit diagram showing the formation of a discriminating circuit.

FIG. 14 is an explanatory view showing another example of a scope discriminating means.

FIG. 15 is a block diagram showing a modification of an output circuit.

FIG. 16 is a block diagram showing a modification of an output circuit.

FIG. 17 is a block diagram showing the formation of an imaging apparatus body.

FIG. 18 is an explanatory view showing a light source part.

FIG. 19 is a block diagram showing the formation of an imaging apparatus body.

FIG. 20 is a perspective view showing an example of the system of this embodiment.

FIG. 21 is a perspective view showing a rotary filter.

FIG. 22 is an explanatory view showing a part of a rotary filter as being rotated.

FIG. 23 is a perspective view showing a modification of a rotary filter.

FIG. 24 is a partly sectioned view of FIG. 23.

FIG. 25 is an explanatory view showing a modification of a rotary filter.

FIG. 26 is a perspective view showing a modification of an imaging apparatus body.

FIG. 27 is a block diagram showing the formation of an imaging apparatus body in a modification of this embodiment.

FIG. 28 is a block diagram showing the formation of an imaging apparatus body in a modification of this embodiment.

FIG. 29 is a perspective view showing the entire system of an endoscope apparatus.

FIG. 30 is a block diagram showing the formation of an imaging apparatus body.

FIG. 31 is an explanatory view showing a light source part.

FIG. 32 is an explanatory view showing a concrete formation of a light source apparatus.

FIG. 33 is a perspective view showing a light source apparatus.

FIG. 34 is a perspective view showing a modification of FIG. 33.

FIGS. 35 and 36 are perspective views showing respectively modifications of a moving mechanism of a rotary filter.

FIGS. 37 and 38 are explanatory views showing respectively modifications of a moving mechanism of a rotary filter.

FIG. 39 is a perspective view showing an endoscope apparatus in a modification of this embodiment.

FIG. 40 is an explanatory view showing a light source pat.

FIG. 41 is an explanatory view showing a rotary filter.

FIG. 42 is a block diagram showing the formation of a field sequential type process circuit.

FIG. 43 is a perspective view showing the appearance of an endoscope apparatus.

FIG. 44 is a block diagram showing a light source part and field sequential type video processor as combined with each other.

FIG. 45 is a block diagram showing a light source part and synchronous type video processor as combined with each other.

FIG. 47 is a perspective view showing the entire system of an endoscope apparatus.

FIG. 48 is a block diagram showing the formation of an imaging apparatus body.

FIG. 49 is a perspective view showing a modification of a connector.

FIG. 50 is a block diagram showing the formation of an imaging apparatus body.

FIG. 51 is an explanatory view showing a light source part.

FIG. 52 is a perspective view showing the appearance of an endoscope apparatus.

FIG. 53 is a block diagram showing the formation of an imaging apparatus body.

FIG. 54 is a block diagram showing the formation of an imaging apparatus body.

FIG. 55 is an explanatory diagram showing transmitted wavelength regions of respective filters of a rotary filter for special picture images.

FIG. 56 is an explanatory diagram showing another example of transmitted wavelength regions of respective filters of a rotary filter for special picture images.

FIG. 57 is a block diagram showing the formation of an imaging apparatus body.

FIG. 58 is a sectioned view of a light source part.

FIG. 59 is a sectioned view on line A-A' in FIG. 58.

FIG. 60 is a perspective view showing fitting and removing a filter cassette.

FIG. 61 is a perspective view showing a light source apparatus.

FIG. 62 is a perspective view showing another example of a light source apparatus.

DETAILED DESCRIPTION OF THE PREFERRED EMBODIMENT

FIGS. 1 to 11 show the first embodiment of the present invention.

Figure 1:
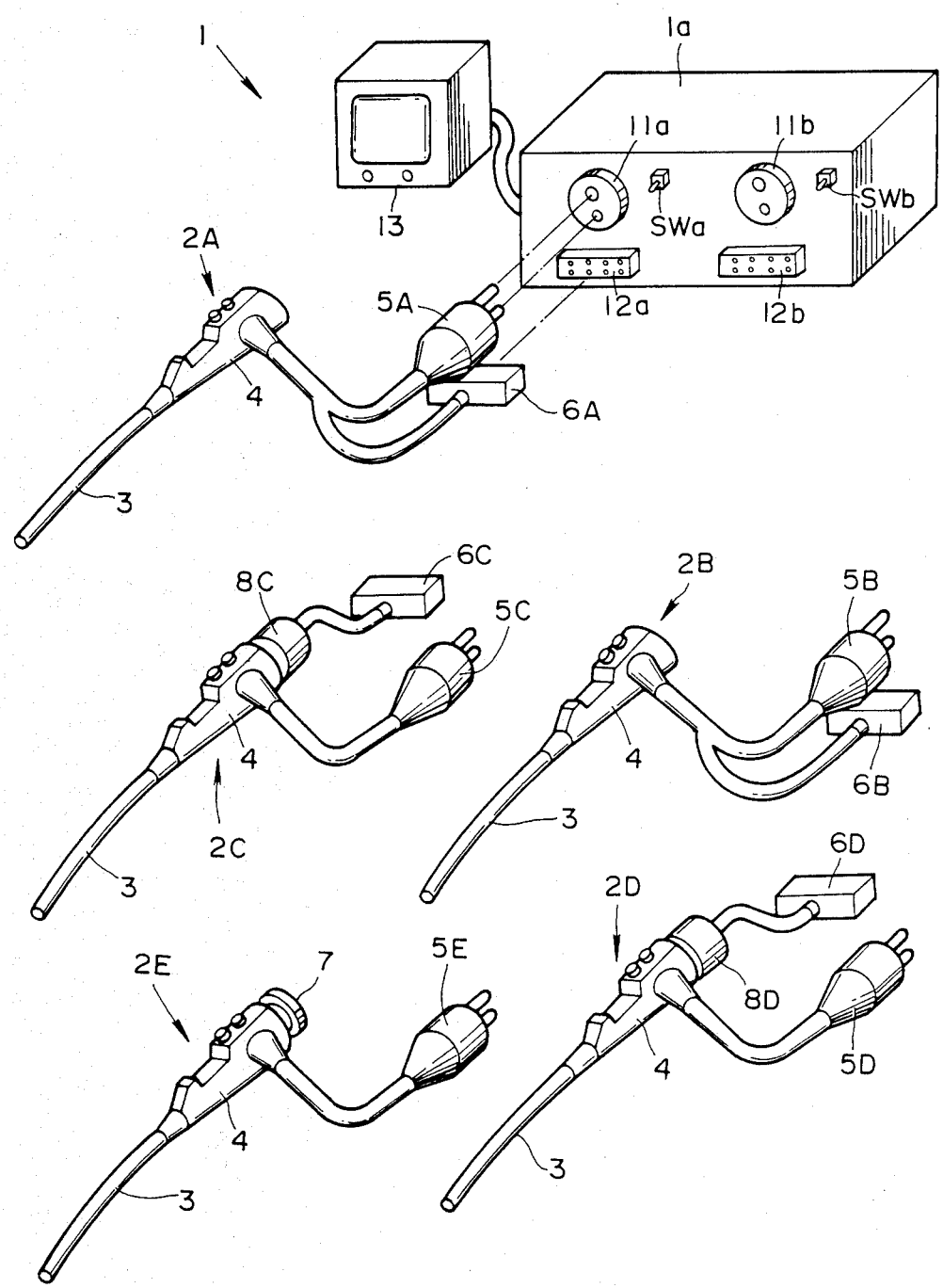

As shown in FIG. 1, an endoscope apparatus 1 of the first embodiment has an imaging apparatus body 1a to which any of scopes (endoscopes) 2A, 2B, 2C, 2D and 2E can be connected. There are five kinds of scopes as shown in FIG. 1, that is, a field sequential type electronic scope 2A, an electronic scope (which shall be mentioned as a synchronous type electronic scope hereinafter) 2B using a color mosaic filter, a fiber scope 2C externally fitted with a field sequential type TV camera (which shall be mentioned as a fiber scope fitted with a field sequential type TV camera hereinafter), a fiber scope 2D externally fitted with a synchronous type TV camera (which shall be mentioned as a fiber scope fitted with a synchronous type TV camera hereinafter) and a fiber scope 2E. Each of the above mentioned respective scopes 2A, 2B, 2C, 2D and 2E has an elongate insertable part 3 and an operating part 4 connected to the rear end side of this insertable part 3. A universal cord 5 is extended from this operating part 4 and is provided at the tip with a light source connector 5A, 5B, 5C, 5D or 5E. In this case, in each of the field sequential type electronic scope 2A and synchronous type electronic scope 2B, a signal connector 6A or 6B is provided in addition to the light source connector 5A or 5B on the side of the above mentioned universal cord 5. The fiber scope 2C, fitted with the sequential type television camera, and fiber scope 2D, fitted with the synchronous type television camera, are fitted respectively with a field sequential type television camera 8C and synchronous type television camera 8D in the eyepiece part 7 of the fiber scope 2E. Signal connectors 6C and 6D are fitted respectively to the tips of signal cables extending out of the respective television cameras 8C and 8D. Two sets of connector receptacles are provided on the front surface, for example, of a housing of the imaging apparatus body 1a so that the connectors 5A, 6A; 5B, 6B; 5C, 6C; 5D, 6D; 5E of these respective scopes 2A, 2B, 2C, 2D and 2E (which shall be represented by the reference numeral 2 in common to all these scopes hereinafter) may be connected to set the respective scopes 2 in a usable state. These connector receptacles consist of a field sequential type light source connector receptacle 11a and field sequential type signal connector receptacle 12a and of a white light source connector receptacle 11b and synchronous type signal connector receptacle 12. The field sequential type light source connector receptacle 11a is in a form that can connect the respective light source connectors 5A and 5C of the same form of the field sequential electronic scope 2A and the fiber scope 2C fitted with the field sequential type television camera (these two scopes 2A and 2C are mentioned also as field sequential type scopes). The field sequential type signal connector receptacle 12a adjacent to the lower side of the above mentioned field sequential type light source connector receptacle 11a is in a form that can connect the respective signal connectors 6A and 6C of the same form of the field sequential type electronic scope 2A and the fiber scope 2C fitted with the field sequential type television camera, that is, of the field sequential type scopes 2A and 2C.

On the other hand, so that the light source connector 5B of the synchronous electronic scope 2B, the light source connector 5D of the fiber scope 2D fitted with the TV camera (these two scopes 2B and 2D are mentioned also as synchronous type scopes) and the light source connector 5E of the fiber scope 2E may be respectively connected to the white light source connector receptacle 11b, these connectors 5B, 5D and 5E are in the same form. Also, so that the signal connector 6B of the synchronous type electronic scope 2B and the signal connector 6D of the fiber scope 2D fitted with the synchronous type TV camera may be connected to the synchronous type signal connector receptacle 12b adjacent to the lower side of this white light source connector receptacle 11b, these connectors 6B and 6D are in the same form.

In case the above mentioned fiber scope 2E is connected to be used, a naked eye observation will be made but, in case the other scopes 2A, 2B, 2C and 2D are to be used, the imaged image can be color-displayed by a color monitor 13 connected to the signal output end of the imaging apparatus body 3.

In this embodiment, the light source connectors 5A, 5B, 5C, 5D and 5E in the respective scopes 2 are provided with light guide connectors and air and water feeding connectors which can be thus connected to the connector receptacles 11a and 11b.

The formations of the interiors of the above mentioned respective scopes 2A, 2B, 2C, 2D and 2E are shown respectively in FIGS. 2, 3, 4, 5 and 6.

A light guide 14 transmitting the illuminating light is inserted through each scope 2, the illuminating light fed to the entrance end surface of the light guide 14 from a light source part 15a or 15b within the imaging apparatus body 1a is transmitted to the exit end surface side and can illuminate the object side in front through a light distributing lens 16 arranged in front of this exit end surface.

In each of the scopes 2, an image forming objective lens 17 is arranged in the tip part of the insertable part 3. In the field sequential type or color mosaic type electronic scope 2A or 2B, a CCD 18 is arranged in the focal plane of this objective 17. On the other hand, in the fiber scope 2E or the fiber scope 2C or 2D fitted with the TV camera 8C or 8D, the entrance end surface of the image guide 19 is arranged to be in the focal plane of the objective 17.

An eyepiece 21 is arranged as opposed to the exit end surface of the above mentioned image guide 19. In the fiber scope 2E, an observation can be made with a naked eye brought close to the eyepiece part 7.

On the other hand, where the field sequential type TV camera 8C or synchronous type TV camera 8D is fitted to the eyepiece part 7 of the fiber scope 2E, a CCD 22 is arranged (through an image forming lens not illustrated) as opposed to the eyepiece 21. A color mosaic filter 23 is arranged on the front surface of the imaging surface of the CCD 18 or 22 used in the synchronous type electronic scope 2B or synchronous type TV camera 8D.

The optical image formed on the imaging surface is photoelectrically converted by the CCD 18 or 22, is amplified by a pre-amplifier 24, is then transmitted to the signal connector 6 (representing 6A, 6B, 6C or 6D) side through a signal transmitting line and is input into a video processor 25a or 25b through the signal connector receptacle 12a or 12b to which this connector is connected. A CCD driving clock is applied to the CCD 18 or 22 from a driver 26a or 26b forming the video processor 25a or 25b.

The other scopes than the fiber scope 2E are provided respectively with type signal generating circuits 27A, 27B, 27C and 27D outputting scope discriminating type signals so that the scope may be discriminated by a discriminating circuit 28a or 28b within the imaging apparatus body 1 through the signal connector 6.

Figure 2:
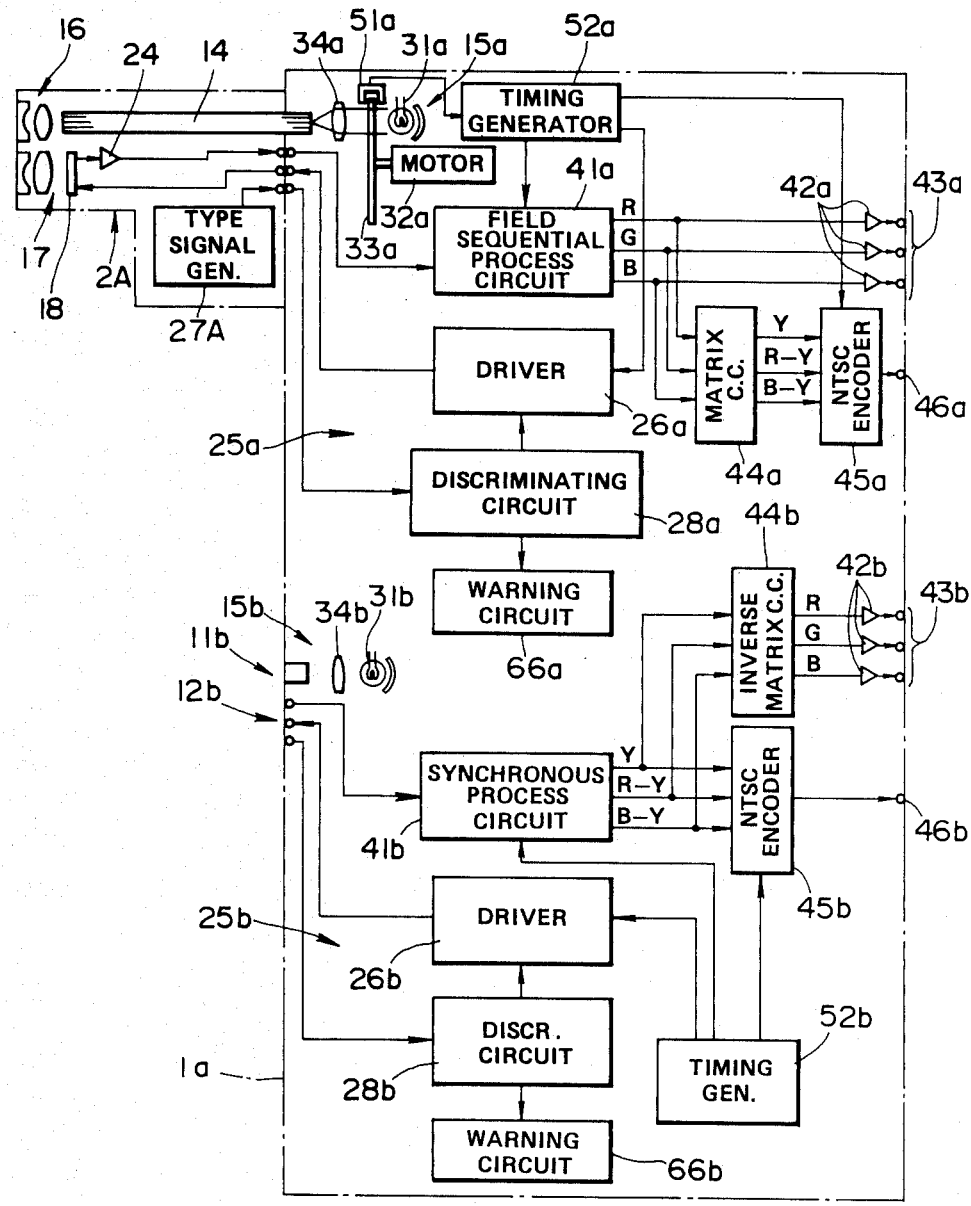
Figure 3:
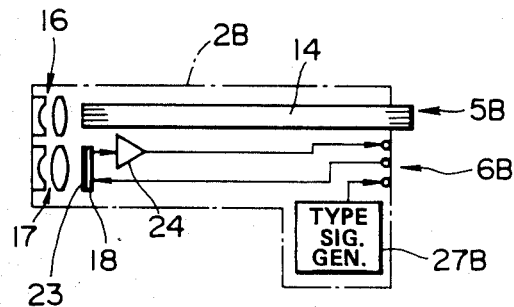

Now, as shown in FIG. 2 (A), two sets of light source parts 15a and 15b and two sets of video processors 25a and 25b are contained within the imaging apparatus body 1a to which any of the above mentioned scopes 2 can be connected.

One light source part 15a is of a field sequential type. The white light of the light source lamp 31a is made of illuminating light of R, G and B through a rotary filter 33a rotated by a motor 32a, is then condensed through a condenser lens 34a and is fed to the entrance end surface of the light guide 14 fitted to the connector receptacle 11a.

The other light source part 15b is a white light source. The white light of the white light source lamp 31b is condensed by the condenser lens 34b, is led to the white light source connector receptacle 11b and is fed to the entrance end surface of the light guide 14 fitted to this connector receptacle 11b.

Now, one video processor 25a is for the field sequential type signal frequency. The signal input into the signal input terminal of the field sequential type signal connector receptacle 12a is input into a field sequential type process circuit 41a and the signals imaged under the illuminating light of the respective wavelengths of R, G and B are output as color signals R, G and B. Then, these color signals R, G and B output three primary color signals R, G and B from three primary color output ends 43a through drivers formed respectively of buffers 42a. A luminance signal Y and color difference signals R-Y and B-Y are produced from the above mentioned color signals R, G and B through a matrix circuit 44a, are then input into an NTSC encoder 45a and are converted to an NTSC system composite video signal which is output from an NTSC output end 46a.

A rotary position sensor 51a detecting the rotary position is provided in one place on the outer periphery of the rotary color filter 33a forming the above mentioned field sequential type light source part 15a. The clock timing of a timing generator 52a is synchronized with the rotation of the rotary filter 33a by the output of this rotary position sensor 52a. The output of this timing generator 52a controls the timing of the field sequential type process circuit 41a.

Figure 7:
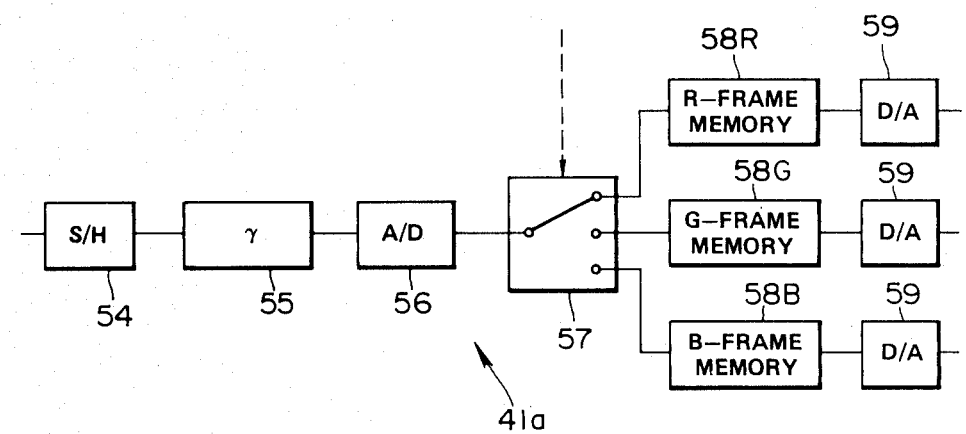

The above mentioned field sequential type process circuit 41a is formed as shown, for example, in FIG. 7. That is to say, the signal input through a pre-amplifier is input into a sample holding circuit 54, is sample-held, is term γ-corrected by a γ-correcting circuit 55 and is converted to a digital signal by an A/D converter 56. The signals imaged under the field sequential illuminations of R, G and B through a multiplexer 57 switched by the signal of the above mentioned timing generator 52a are written into an R frame memory 58R, G frame memory 58G and B frame memory 58b. The signal data written into these respective frame memories 58r, 58G and 58B are read out simultaneously, are converted respectively to analogue color signals R, G and B by D/A converters 59 and are output in the above mentioned output on the above described matrix circuit 44a side. On the other hand, the signal imaged by the CCD 18 or 22 through the synchronous type signal connector 18b is input into the synchronous type process circuit 41b to output a luminance signal Y and color difference signals R-Y and B-Y. These signals are input into an NTSC encoder 45b and are converted to an NTSC system composite video signal which is output from the NTSC output end 46b. They are input also into an inverted matrix circuit 45b and are converted to color signals R, G and B and three primary color signals R, G and B are output from three primary color output ends 43b respectively through buffers 42b forming drivers.

Figure 8:
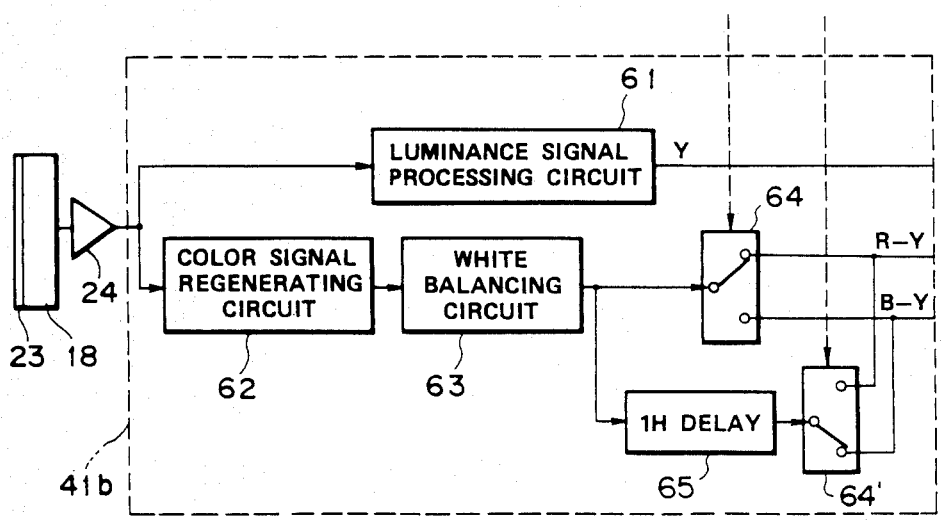

In the above mentioned synchronous type process circuit 41b, as shown, for example, in FIG. 8, the signal from the CCD 18 (or 22) amplified by the pre-amplifier 24 is transmitted through a luminance signal processing circuit 61 to produce a luminance signal Y and is also input into a color signal reproducing circuit 62 to produce color difference signals R-Y and B-Y in each horizontal line in time series which are white balance-compensated in a white balance circuit 63. One of them is input directly into an analogue switch 64. The other is delayed by one horizontal line in a 1H delay line 65 and is input into an analogue switch 64' and color difference signals R-Y and B-Y are obtained by the switching signal of a timing generator 52b.

The respective timing generators 52a and 52b control to apply signals respectively to the drivers 26a and 26b and TNSC encoders 45a and 45b and to make a signal process synchronized with driving pulses used to read signals out of the CCD 18 or 22. In this case, in the field sequential type video processor 25a, the above mentioned timing generator 52a is synchronized with the rotary color filter 33 by he output of the rotary position sensor 51a. The above mentioned NTSC encoders 45a and 45b are formed to contain buffers.

Now, each of the type signal generating circuits 27A, 27B, 27C and 27D is formed by connecting a resistance or the like of a different resistance value, for example, between two terminals. On the other hand, in the discriminating circuits 28a and 28b, whether the scope of either resistance value is connected can be discriminated by comparing the resistance value between two terminals by using a comparator or the like. Any mis-connection will be warned by a buzzer or lighting of an LED.

Examples of the thus operating type signal generating circuit and discriminating circuit are shown in FIGS. 9 and 10.

As shown in FIG. 9, in the above mentioned type signal generating circuits 27A, 27C and 28B, 27D, two terminals 72, for example, in the signal connectors 6A and 6B are connected between them through a resistance R0 of a proper value (for example 220 Ω) between them and are short-circuited between them through a lead wire 73. On the other hand, discriminating circuit 28a, as shown in FIG. 10 (A0, one input end 75 of the input ends 75 connected with the above mentioned two terminals 72 is connected to a current source end, for example, of +5 V and the other input end 75 is connected to the non-inverted input ends of comparators 76 and 77 and is grounded through a resistance R0, for example, of 220 Ω.

A voltage $V_1$, for example, of 3 to 4 V is applied by a reference voltage source to the inverted input end of one comparator 76 and a voltage $V_2$, for example, of 1 to 2 V is applied by a reference voltage source to the inverted input end of the other comparator 77. The outputs of the above mentioned both comparators 76 and 77 are led to an output end 79 through a two-input AND circuit 78.

The above mentioned output end 79 will be "L" in case the signal connector 6A or 6C of the field sequential type scope 2A or 2C is connected to the field sequential type signal connector 12a but will be "H" when the signal connector 6B or 6D of the mosaic type scope 2B or 2D is connected by mistake to this connector receptacle 12a. Then, a warning instructing signal will be output to the warning circuit 66a, the buzzer will be operated or the LED will be lighted to warn the mis-connection.

In the other discriminating circuit 28b, in FIG. 10 (B), the output of the comparator 76 as inverted by an inverter 81 and the output of the comparator 77 are led to an output end 83 through a two-input AND circuit 82.

According to this discriminating circuit 28b, the output end 83 will be "L" in case the synchronous type scope 2B or 2D is connected but will be "h" when the signal connector 6A or 6C of the field sequential type scope 2A or 2C is connected by mistake. Then, a warning instructing signal will be output in the warning circuit 66b and the mis-connection will be warned by the buzzer or LED.

Now, for example, on the front surface of the housing of the imaging apparatus body 1a, a field sequential type current source switch SWa and synchronous type current source switch SWb are provided and can be switched on and off independently of each other.

According to the thus formed first embodiment, as it has the field sequential type scope light source part 15a, field sequential type video processor 25a, synchronous type scope light source part 15b and synchronous type video processor 25b and is provided with connecting means for the respective scopes, even if any of the field sequential type scopes 2A and 2C and synchronous type scopes 2B and 2D is connected, the illuminating light corresponding to the connected scope can be fed and the signal can be processed and the object image imaged by this scope can be color-displayed by the color monitor 13.

Also, in case the fiber scope 2E is used, its light source connector 5E can be connected to the white light source connector receptacle 11b so that a naked eye observation can be made.

The light source connector part and signal connector part are provided adjacently to each other for the field sequential type connector receptacles 11a and 12a and synchronous type connector receptacles 11b and 12b. Those on the field sequential side and those on the synchronous side are made separate from each other. Therefore, the scope as connected can be set in the operating state for a different imaging system by merely switching on and off the switch SWa or SWb without removing the scope each time of use.

Further, as the light source connector receptacles 11a and 11b are provided separately for the field sequential type and white light, the field sequential type light source part and white light source part can be provided separately, the illuminating light can be fed to the respectively different connector receptacles, no output means by switching the field sequential illuminating light and white illuminating light is required and the formation is simple. Also, as the signal connector receptacles 12a and 12b are separate for the field sequential type and synchronous type, no means of delivering the signal from the solid state imaging device 18 or 22 as switched to the field sequential type video processor 25a and synchronous type video processor 25b is required and the formation is simple.

On the other hand, in case a wrong scope is connected to the two sets of connector receptacles 12a and 12b provided in the imaging apparatus body 1a, the wrong connection will be sensed by the discriminating circuit 28a or 28b and will be warned by the warning circuit 66a or 66b.

Therefore, according to this first embodiment, if one imaging apparatus body 1a is provided, a scope different in the color imaging system can be coped with and even the fiber scope 2E can be simultaneously used. In case a wrong connection is made, a warning will be given. Therefore, the apparatus is convenient to use. If the signal connector 6 (signal connector receptacle 12) is made different in form between the field sequential type and synchronous type, the mis-connection can be simply prevented and the mis-operation can be positively prevented.

The signals processed for the above mentioned two color imaging systems coincide in the output form. That is to say, either is made to coincide with the three primary color outputs or NTSC system video signal. Therefore, the same color monitor 13 can be used. (This color monitor may correspond to three primary colors or the NTSC system video signal may be input.) In case the TV camera 8C or 8D is fitted to the fiber scope 2E, the imaged picture image will be displayed in the color monitor 13. In case the TV camera 8C or 8D is removed, the removed state may be displayed on the picture surface of the color monitor 13.

According to the above mentioned first embodiment, in case the signal connector 6A or 6C of the field sequential type scope 2A or 2C is correctly connected to the field sequential type signal connector receptacle 12a, a lamp different from the warning LED may be lighted or an LED of a different color may be lighted to make the right connection known. This can be applied the same also to the synchronous type.

The case that two signal connectors are simultaneously connected to both signal connector receptacles 12a and 12b may be warned. Also, a light source connector connection sensing means may be provided inside the field sequential type light source connector receptacle 11a so that, in case the connector 5E of the fiber scope 2E is connected, the mis-connection may be made known. That is to say, the case that the connector 5E is connected to the connector receptacle 11a and no connector is connected to the signal side connectors 11a and 11b may be warned.

Figure 11A:
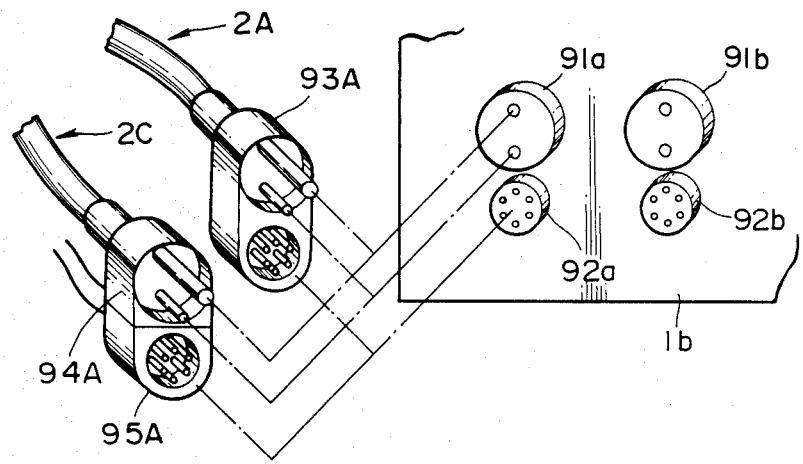

FIGS. 11 (A) and (B) show modifications of connectors and connector receptacles.

In the imaging apparatus body 1b, a round field sequential type light source connector receptacle 91a and signal connector receptacle 92a and white light source connector receptacle 91b and synchronous type signal connector receptacle 92b are provided as separated from each other on the front surface or the like of the housing.

On the other hand, as shown in FIG. 11 (A), the field sequential type scope 2A is provided with a connector 93A integrating the light source connector part and signal connector 94 part so as to be connectable to the field sequential type light source connector receptacle 91a and signal connector receptacle 92a.

Figure 11B:
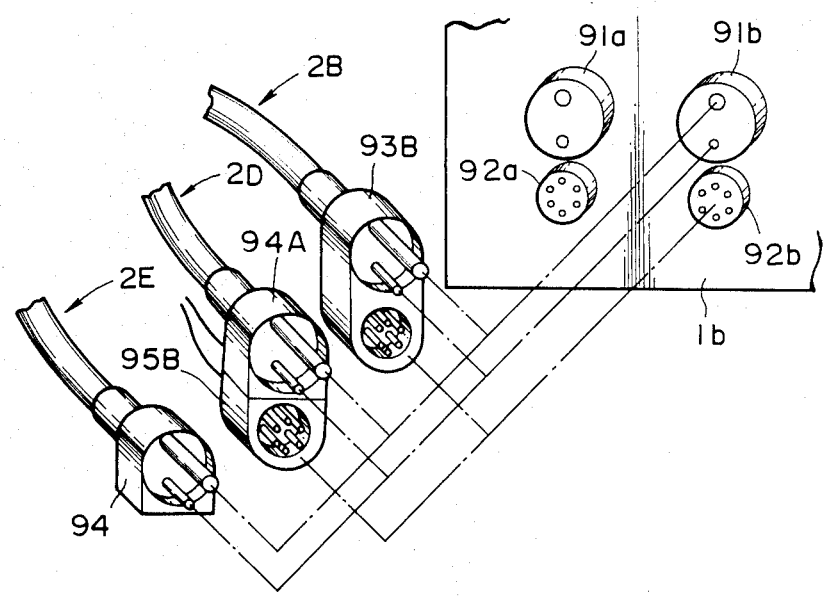

Likewise, as shown in FIG. 11(B), the synchronous type scope 2B is provided with a connector 93B connectable to the above mentioned white light source connector receptacle 91b and synchronous type signal connector receptacle 92b.

Also, as shown in FIG. 11 (A), the fiber scope 2C fitted with a field sequential type TV camera is made to be of the same form as of the connector 93A of the above mentioned field sequential type electronic scope 2A when the light source connector 94A and signal connector 95A are combined with each other and can be used as connected to the field sequential type connector receptacles 91a and 92a.

As shown in FIG. 11 (B), the fiber scope 2D fitted with a synchronous type TV camera is to be made of the same form as of the connector 93B of the above mentioned synchronous type electronic scope 2B when the light source connector 94A and signal connector 95B are combined with each other and can be connected to the white light source connector receptacle 91b and signal connector receptacle 92b.

The light source connector 94 of the fiber scope 2E can feed a white light toward the light guide of the fiber scope 2E when connected to the white light source connector receptacle 92b so that the object may be observed with a naked eye.

In case a connection different from the connection shown in FIGS. 11 (A) and (B) is made, the signal of the type signal generating circuit will be discriminated by the connection of the signal connector as explained in the first embodiment and a warning will be issued.

Figure 12:
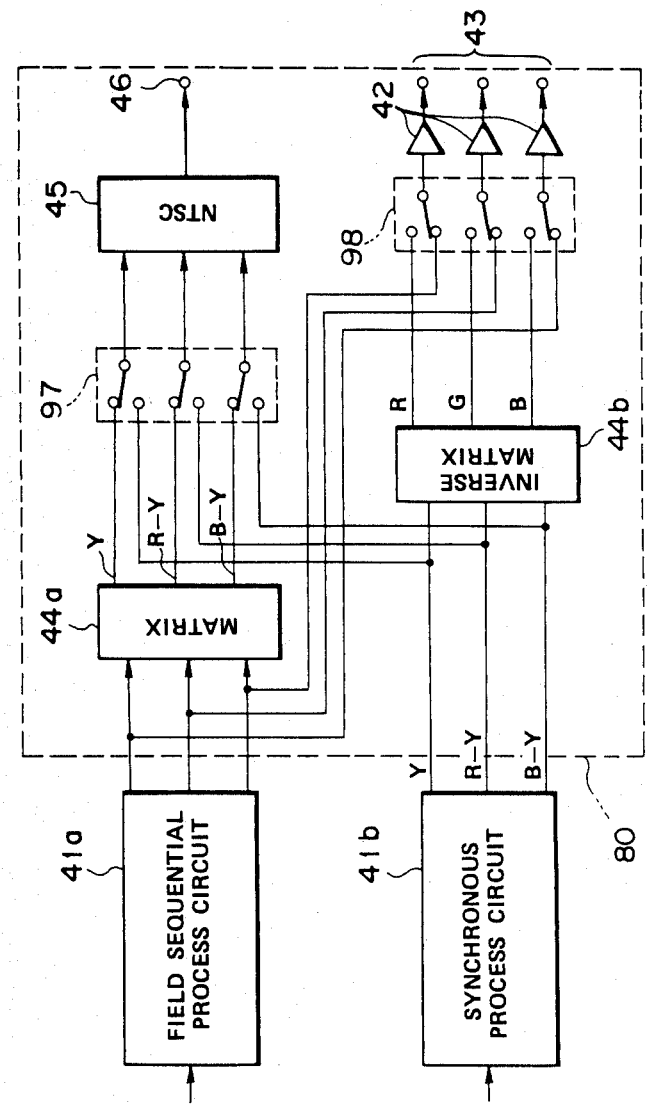
FIGS. 12 to 14 relate to the second embodiment of the present invention.
Figure 13:
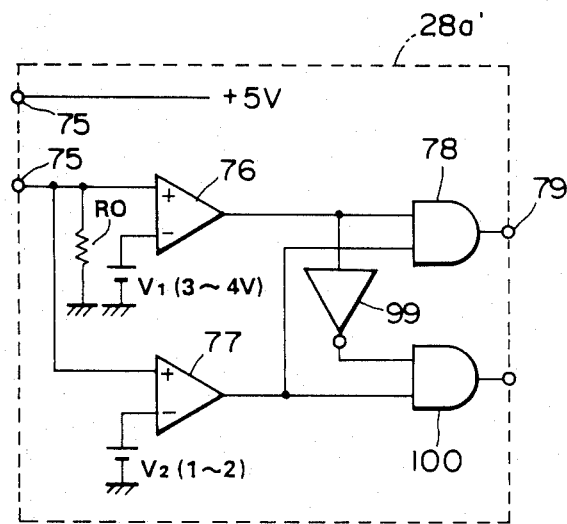
Figure 14:
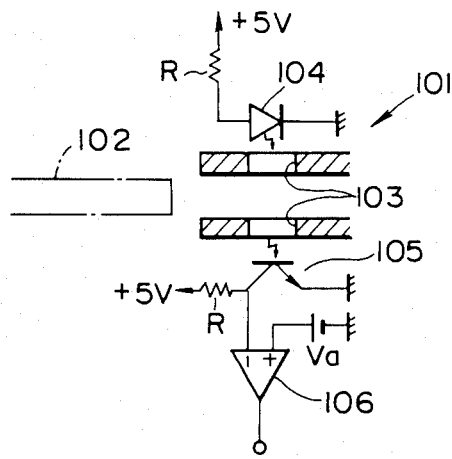

FIGS. 12 to 14 show the second embodiment of the present invention.

In this second embodiment, in an output circuit 80 (provided with a signal converting function), the output ends of the video processors 25a and 25b in the first embodiment are made common.

That is to say, in FIG. 2, a three-circuit two-contact switching switch 97 is provided between the output end of a matrix circuit 44a and the input end of an NTSC encoder 45a and a three-circuit two-contact switching switch 98 is provided also between the output end of the inverse matrix circuit 44b and the input end of the buffers 42b forming drivers.

When one contact side is on, by the above mentioned switching switch 97, the signal of the matrix circuit 44 will be led to the common NTSC encoder 45 and will be made a video signal of the NTSC system by this NTSC encoder 45 and the video signal will be output from the common NTSC output end 46. When the other contact side is selected, the signal of the synchronous type process circuit 41 will be led to the NTSC encoder 45 and ill be output from the common NTSC output end 46.

On the other hand, on the other switching switch 98, when the field sequential type side is selected, the output signal of the field sequential type process circuit 41a will pass through the common buffers 42 forming the drivers to provide three primary color signals from the common RGB output ends 43. When the synchronous type process circuit side is selected, three primary color signals R, G and B having passed through the inverse matrix circuit 44b will be output from the common RGB output ends 43.

The above mentioned switching switches 97 and 98 can be respectively manually switched or can be switched as operatively connected. Also, a type signal output from a scope to which the above mentioned both switching switch 97 and 98 are connected as shown in FIG. 2 is used to be discriminated by the discriminating circuit 28a or 28b. With this discriminated signal, the process circuit 41a or 41b processing the signal corresponding to the scope to which the switching switches 97 and 98 are connected can be switched. In order to do it, the discriminating circuit 28a shown, for example, in FIG. 10 may be formed to be the circuit 28a shown in FIG. 10 (A). In the discriminating circuit 28a shown in FIG. 10 (A), in case the output is "H" when the output of a comparator 76 as inverted by the inverter and the output of a comparator 77 are passed through a two-input AND circuit 100 (in case the field sequential scopes 2A or 2C is connected), the above mentioned switching switches 97 and 98 may be switched to the field sequential side.

In case the above mentioned switching switches 97 and 98 are formed of analogue switches or the like, they can be automatically switched by a connection sensing apparatus 101 shown in FIG. 14.

For example, the field sequential type connector is provided with a discriminating pin 102 which is not found in the synchronous type and the field sequential type connector receptacle is provided with a recess in which this pin can be engaged. Lateral holes 103 are made in both side parts opposed to this recess. A light emitting means such as an LED 104 and a light receiving means such as a phototransistor 105 are arranged. The output of the phototransistor 105 as a light receiving means is input into a discriminating circuit formed of a comparator 106 or the like. The above mentioned LED 104 is fed with a current from a current source, for example, of 5 v, through a resistance R. The phototransistor 105 is fed at the collector with +5 V through a resistance R and is grounded at the emitter. This collector is connected to the non-inverted input end of the comparator 106 and its voltage is compared with the voltage Va connected to the inverted input end. This voltage Va is set, for example, at 2 to 3 V. Normally, as the phototransistor 105 is conducting, the output of this comparator 106 is "L". When the pin 102 is engaged, the light of the LED 104 will be intercepted and the output of the phototransistor 105 will become "H". This output variation is discriminated by the comparator 106. Its output becomes "H". The connected scope is discriminated. The switching switches 44 and 48 are switched.

In case the output of the phototransistor 84 as a light receiving means is "L", the synchronous type process circuit side will be selected.

When the discriminating means shown in FIG. 14 is provided for discriminating the synchronous scope, a mis-connection can be discriminated. In this case, the discriminating pin may be different between the synchronous type and field sequential type.

Figure 15:
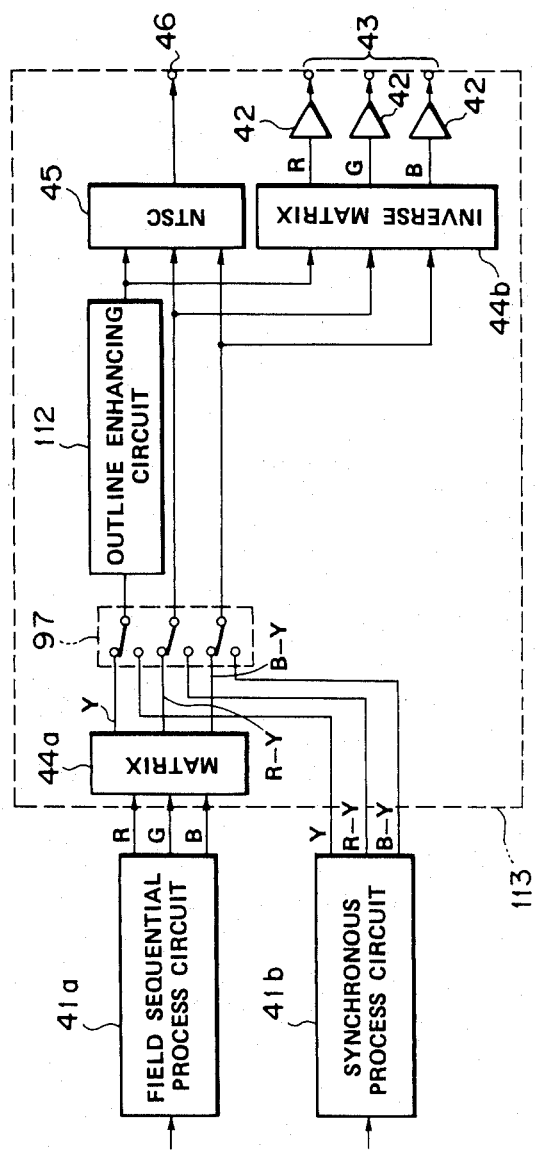
FIGS. 15 and 16 relate to the third embodiment of the present invention.

FIG. 15 shows the third embodiment of the present invention.

In this video processor, in the output circuit 80 having a signal converting function shown in FIG. 12, an output circuit 113 processing the signal to enhance the outline by interposing an outline enhancing circuit 112 for the luminance signal switched by the switching switch 97 is made. The other switching switch 98 shown in FIG. 12 is not provided but may be provided.

The above mentioned switching switch 97 may be switched with the output of the discriminating circuit 28a' or may be manually switched.

The others are the same as is shown in the above mentioned FIG. 12.

In this embodiment, a common outline enhancement is to be made for different luminance signals of two system. Therefore, the number of parts is fewer, the formation is simpler and the cost can be made lower than in the case of providing two sets for the respective systems.

In FIG. 15, not only the outline enhancement (horizontal, vertical or both) but also the NTSC encoder 45 and inverse matrix circuit 44b are commonly used. Also, a line interpolating circuit may be provided instead of the outline enhancing circuit and an auto gain control circuit may be provided.

Further, the commonly used circuits may be not only these but also, for example, a frame memory, stationary picture memory, color burst generator, current source, character generator, superimposing circuit, keyboard controller and color tone adjusting circuit.

Figure 16:
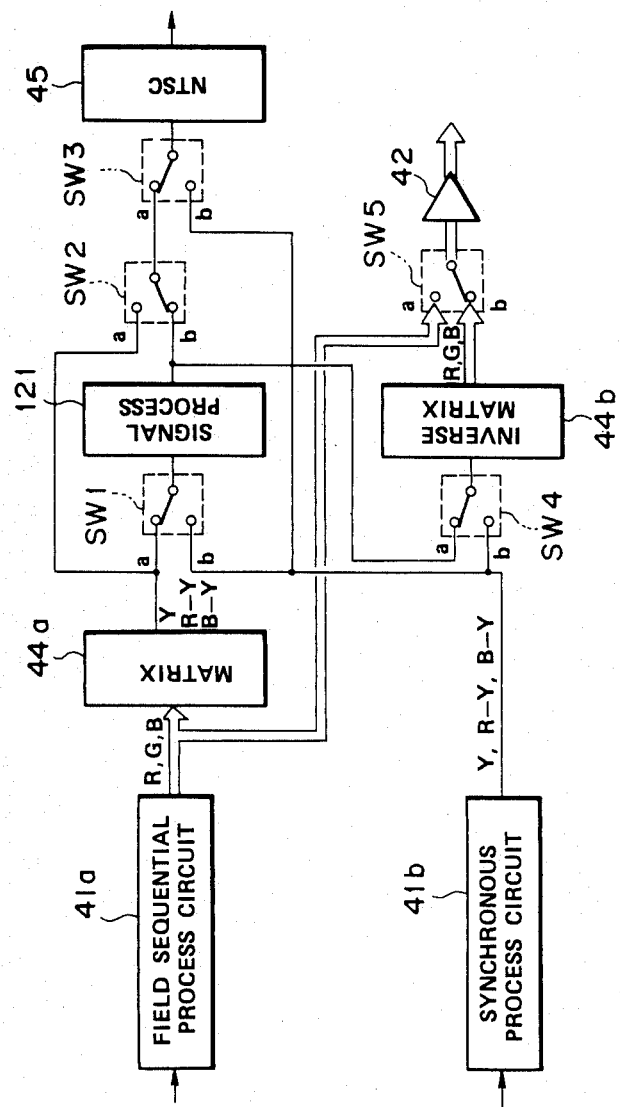

FIG. 16 shows a modification of FIG. 15.

That is to say, in the circuit shown in FIG. 15, (the luminance signal of) any field sequential type or synchronous type signal can be selected to be processed to enhance the outline or the like and, in case the signal is not processed, the deterioration of the signal will be prevented. Therefore, switches SW1 and SW2 are provided respectively before and after a signal processing circuit 121 in the stage after the matrix circuit 44. Also the output of the synchronous type process circuit 41b can be input into the NTSC encoder 45 through a switch SW3 on the output side of the switch SW2. In case the signal having passed through the above mentioned signal processing circuit 121 is output from the RGB output ends, it will be output through a switch SW4, inverse matrix circuit 44b and switch SW5. So that the signals R, G and B of the field sequential type process circuit 41a may not be deteriorated by being returned again to the signals R, G and B through the matrix circuit 44a and inverse matrix circuit 44b, the three primary color signals R, G and B can be output directly from the RGB output end through a switch SW5. In the state of the respective switches SW1 to SW5 in the modification shown in FIG. 16, whether the signal is processed (on) or not (off) is as in the following logical table:

The mark Δ shows that either side will do.

By the way, in the embodiment in FIG. 16, a luminance signal Y and color difference signals R-Y and B-Y are to be processed but only the luminance signal may be processed.

| Logical Table | | | | | | |
|---|---|---|---|---|---|---|
| Output | Signal processing | SW1 | SW2 | SW3 | SW4 | SW5 |
| Field sequential type | On | a | b | a | a | b |
| | Off | Δ | a | Δ | a | a |
| Synchronous type | On | b | b | a | a | a |
| | Off | Δ | b | b | b | b |

In the circuit shown in FIG. 12, in the stage after each switching switch, the luminance signal and respective color signals R, G and B may be processed.

Figure 17:
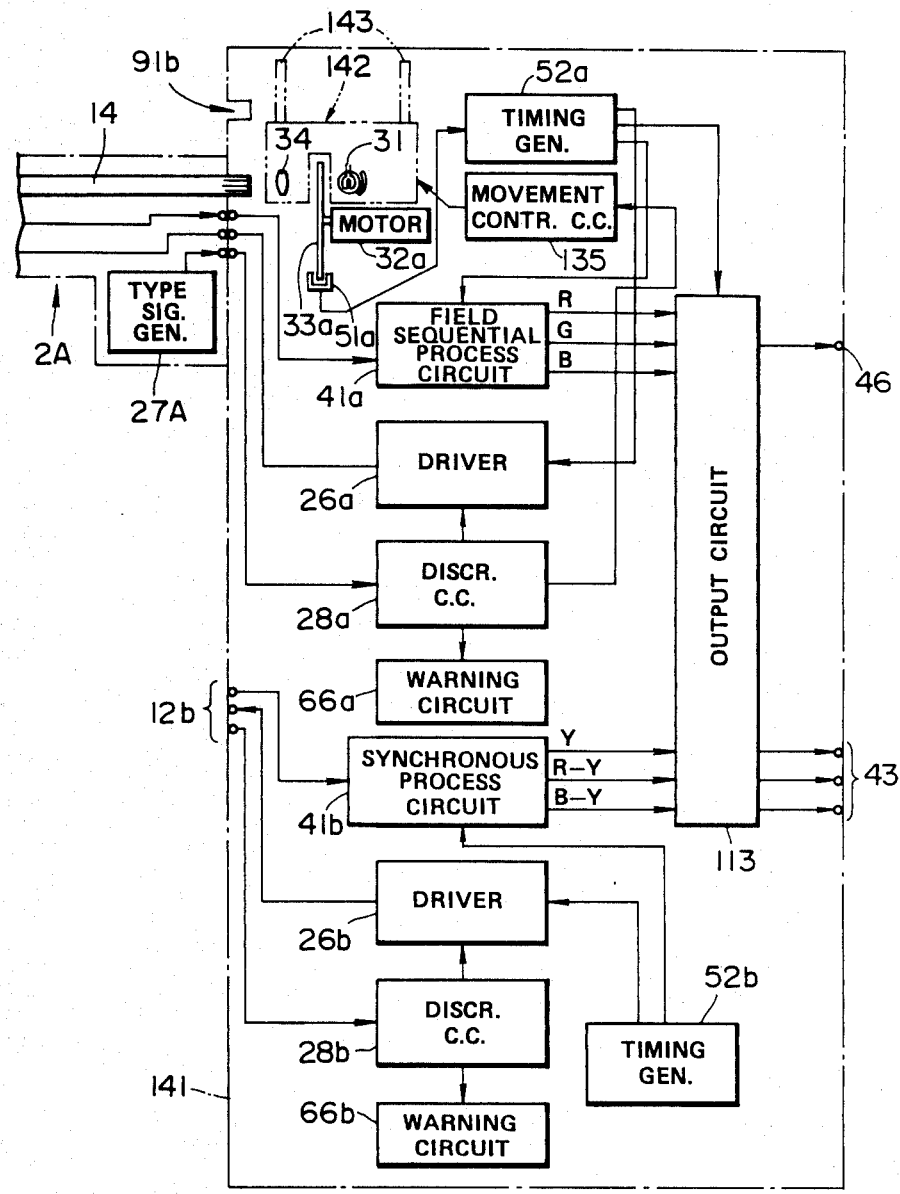
FIGS. 17 and 18 relate to the fourth embodiment of the present invention.
Figure 18:
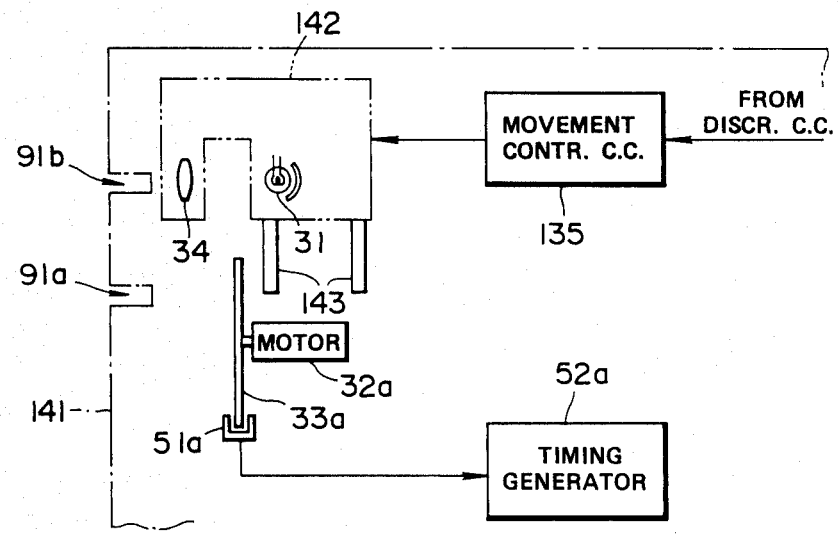

FIGS. 17 and 18 show the fifth embodiment of the present invention.

In this embodiment, a light source part 142 is movable along rails 143.

The connector receptacle part, for example, on the front surface of an imaging apparatus body 141 of this embodiment is of a structure such as shown in FIG. 11. On the other hand, the connector on the scope side is also of the form shown in FIG. 11.

The light source part 142 within the imaging apparatus body 141 is opposed to the inside of a white light source connector receptacle (represented by the same reference numeral as is shown in FIG. 11) 91b usually as shown in FIG. 18. When the field sequential type scope 2A or C is connected, it will be discriminated by the discriminating circuit 28a, by its type signal, the light source part 142 will be moved (downward in FIG. 18 and leftward in FIG. 11) through a movement controlling circuit 135 so as to be opposed to the inside of the field sequential type connector receptacle 91a as shown in FIG. 17 and to feed the illuminating lights of R, G and B having passed through the rotary filter 33a to the field sequential type light source connector part.

In the imaging apparatus body 141 of this embodiment, a commonly used output circuit 113 is used as shown in FIG. 17. The concrete formation of this output circuit 113 is shown in FIG. 15.

The others are of the same formation as in the first embodiment and the operations and effects are substantially the same as in the first embodiment.

In the above mentioned fifth embodiment, the connector receptacle as well as the light source part 142 can be made movable. In such a case, the connector receptacle will not be movable in case the synchronous scope 2B or 2D is connected but will be movable in the case of the field sequential type scope 2A or 2C. It will not be movable in the case of this fiber scope 2E. In such a case, the connector receptacle will be one.

This embodiment can be also made manually movable.

FIGS. 19 to 28 show the sixth embodiment of the present invention.

Figure 20:
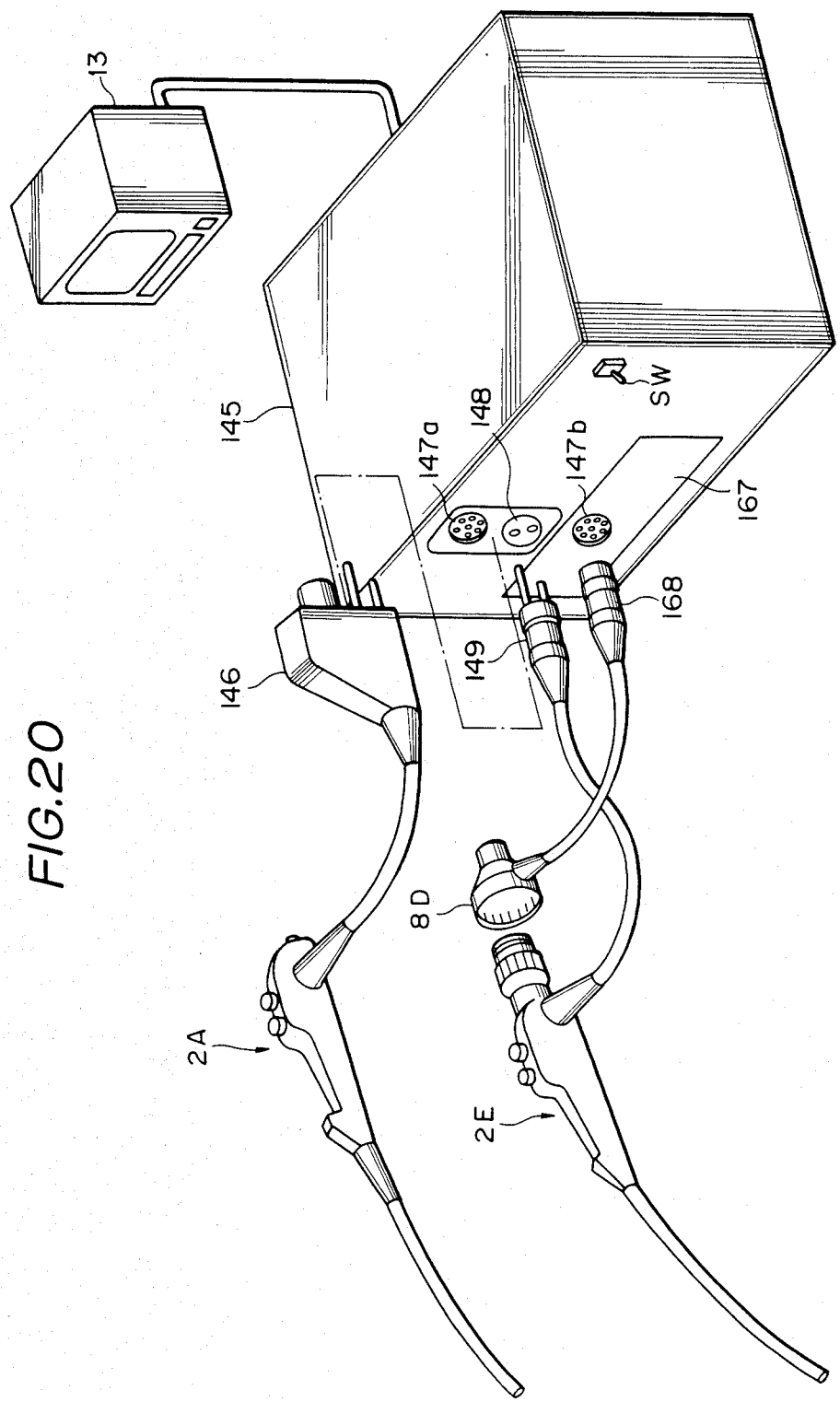

An imaging apparatus body 145 shown in FIG. 20 is provided with an optical source connector receptacle 148 used in common with a field sequential type signal connector receptacle 148 so that the connector 146 of the field sequential type electronic scope 2A may be connected and the image may be color-displayed by the color monitor 13. The above mentioned connector receptacles 147a and 148 can be used as connected with the connector (not illustrate) of the fiber scope 2C fitted with a field sequential type TV camera.

Also, in the case of the fiber scope 2E, its connector 149 can be connected to the light source connector receptacle 148 to make a naked eye observation.

In the light source part inside the above mentioned light source connector receptacle 148, usually a white light is output by using a rotary filter shown, for example, in FIG. 21 and, when the rotary filter is rotated, a field sequential illumination will be made.

In this rotary filter 150, a filter frame 151 is provided with R, G and b color transmitting filters 152R, 152G and 152B and a white color illuminating hole 153 is made in a light intercepting part, for example, between the R and B color transmitting filters 152R and 152B and can have the light intercepted by a light intercepting plate 154 fitted rotatably in a position as a pivotal point on a segment connecting this hole 153 and the center of the filter frame.

Figure 22:
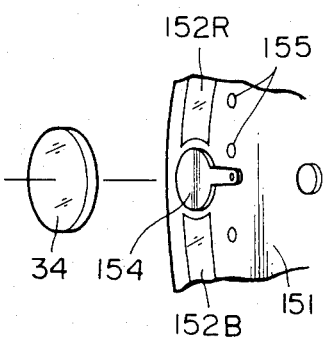

That is to say, in the above mentioned light intercepting plate 154, when the filter frame 151 is rotated by the motor 32a, , due to the centrifugal force, as shown in FIG. 22, the direction connecting the center position of the disc-like light intercepting part with the pivotal point will coincide with the radial direction, in this state, the hole 153 will be intercepted by the light intercepting plate 154 and the ordinary field sequential illumination of R, G and B will be able to be made.

On the other hand, when the filter frame stops, no centrifugal force will act and therefore, as shown in FIG. 14, the light intercepting plate 154 will retreat from the hole 153 under the gravity.

The above mentioned filter frame 151 is controlled in the position so that, when stopped, the hole 153 may be located on the optical axis connecting the light source lamp with the lens 24. For this position control or for detecting the timing of reading out the CCD signal in the case of the field sequence of R, G and B, many holes 155 are provided in the peripheral direction in the filter frame 151, a light emitting device and photosensor 156 are arranged on both sides of the plate surface of the filter frame 151 to form a position detecting rotary encoder. In FIG. 21, the photosensor 156 is fitted to the tip of a sensor fitting plate 157. When a field sequential type signal connector is connected to a field sequential type signal connector receptacle 133a, a rotation/stop circuit 161 will be made operative by the type signal output in such a case and the rotary filter 150 will be rotated by driving the motor 32a to make a field sequential illumination.

Now, a recess is provided on the lower side of the front surface of the above mentioned imaging apparatus body 145 so that a synchronous type pre-processor unit 167 may be plugged in. A mosaic type signal connector receptacle 147b is provided on the front surface of this synchronous type pre-processor unit 167. The signal connector 168 of the mosaic type TV camera 8D or the signal connector (not illustrated) of the synchronous type electronic scope 2B can be connected to this connector receptacle 147b.

Figure 19:
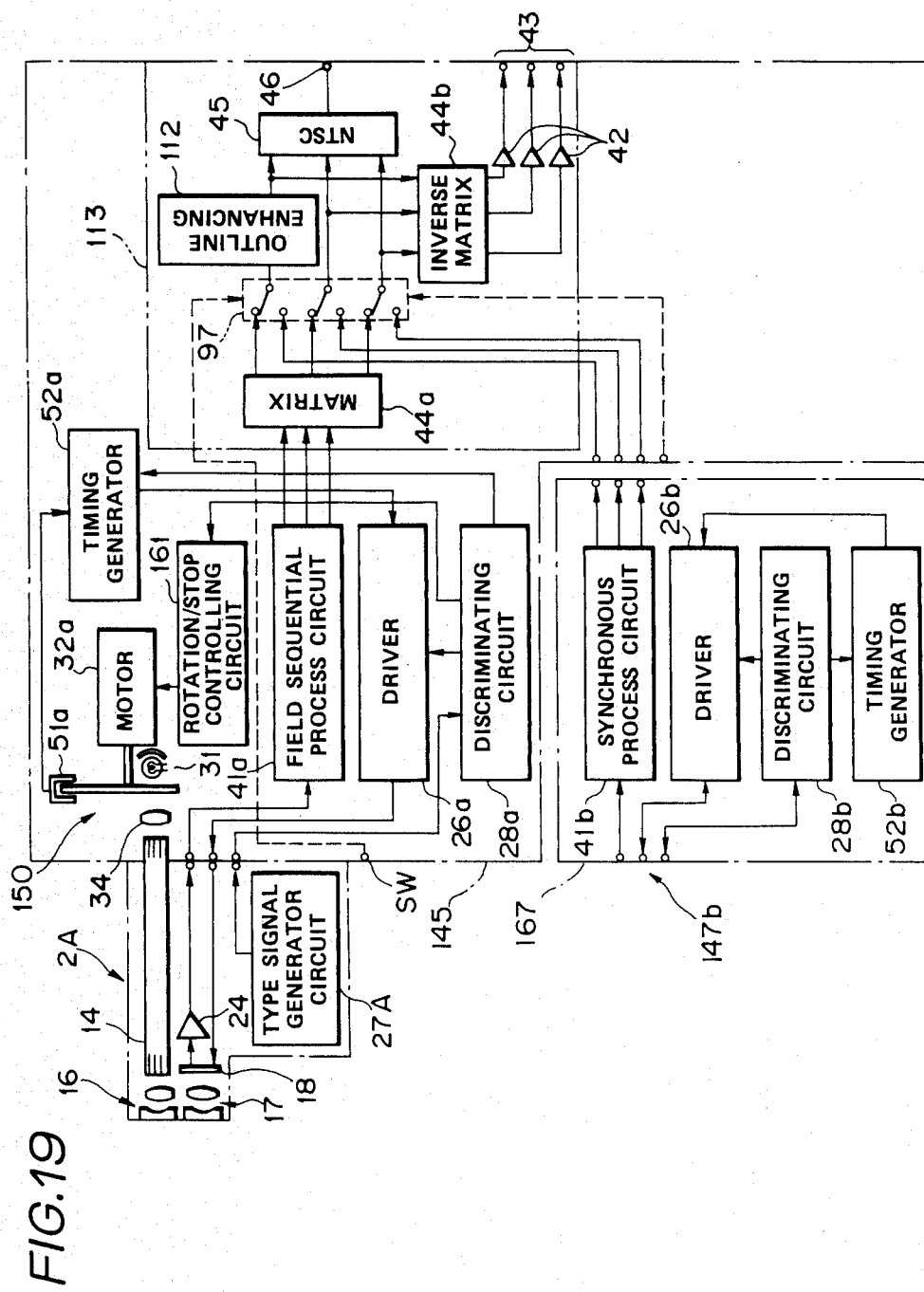
FIGS. 19 to 28 relate to the fifth embodiment of the present invention.
Figure 21:
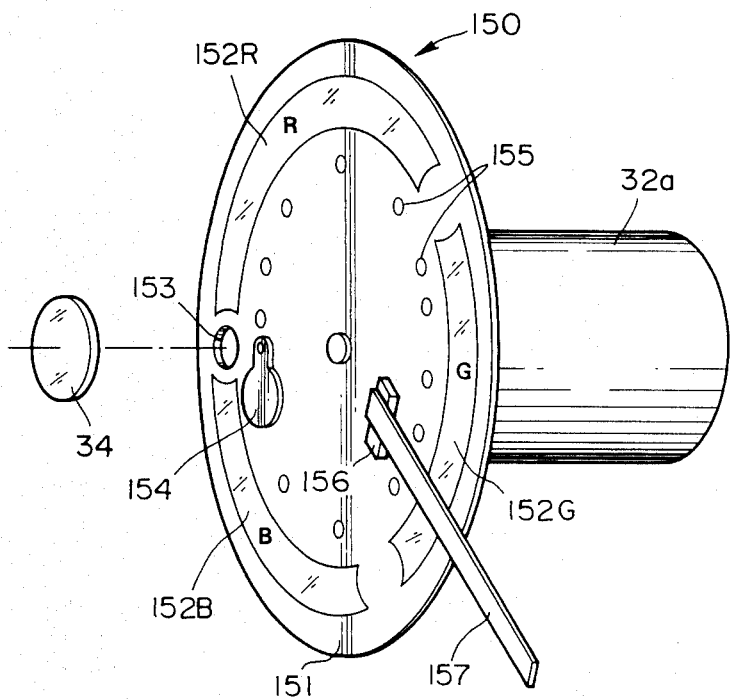

As shown in FIG. 19, a light source part using the rotary filter 150 shown in FIG. 21 and a field sequential type processor are contained within the above mentioned imaging apparatus body.

This field sequential type processor is substantially equal to the one selected in case the switch 103 is switched to the field sequential side in the processor shown in Fig. 17 and further an output circuit 113 provided with a function of processing the signal to enhance the outline as shown in FIG. 15 is made on its output side.

The switching switch 97 within the output circuit 113 provided with the signal processing means enhancing the outline will be switched when the synchronous type pre-processor unit 167 is plugged in.

According to this embodiment, if the mosaic type pre-processor unit 167 is obtained (bought) later as required, even the synchronous type scope can be used and the function of the apparatus can be economically expanded.

So that the field sequential type and synchronous type may be used as switched even in case the synchronous type pre-processor unit 167 is plugged in, a switching switch SW is provided, for example, on the front surface of the apparatus body 145 and the switching of the switching switch 97 can be controlled with this switch SW.

In the above mentioned sixth embodiment, the plugged-in unit can be fitted to the front surface side but the synchronous type video processor unit or a part of it may be slotted into expanding slot provided on the rear side or the like so as to be able to be used for either of the field sequential type and synchronous type scopes.

Figure 26:
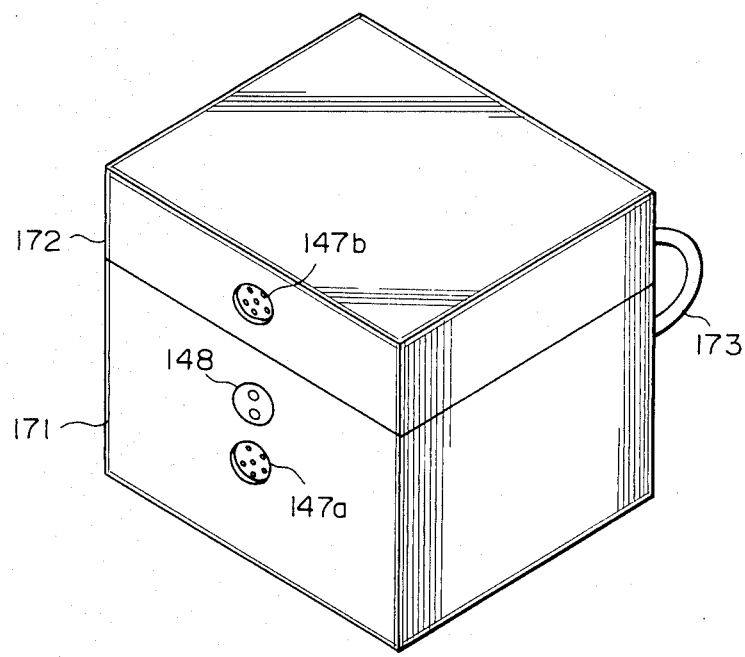

Also, as shown in FIG. 26, the synchronous type video processor 172 may be overlapped on the upper surface of the imaging apparatus body 171 provided with the signal processing means for the field sequential type scope and a signal cable 173 from this synchronous type video processor 172 may be connected to the connector receptacle of the imaging apparatus body 171 so that the scope of either system may be used.

On the front surface of the imaging apparatus body 145, such connector receptacles 147a and 148 as are described above are provided. The synchronous type video processor 142 is also provided with a connector receptacle 147b.

Figure 27:
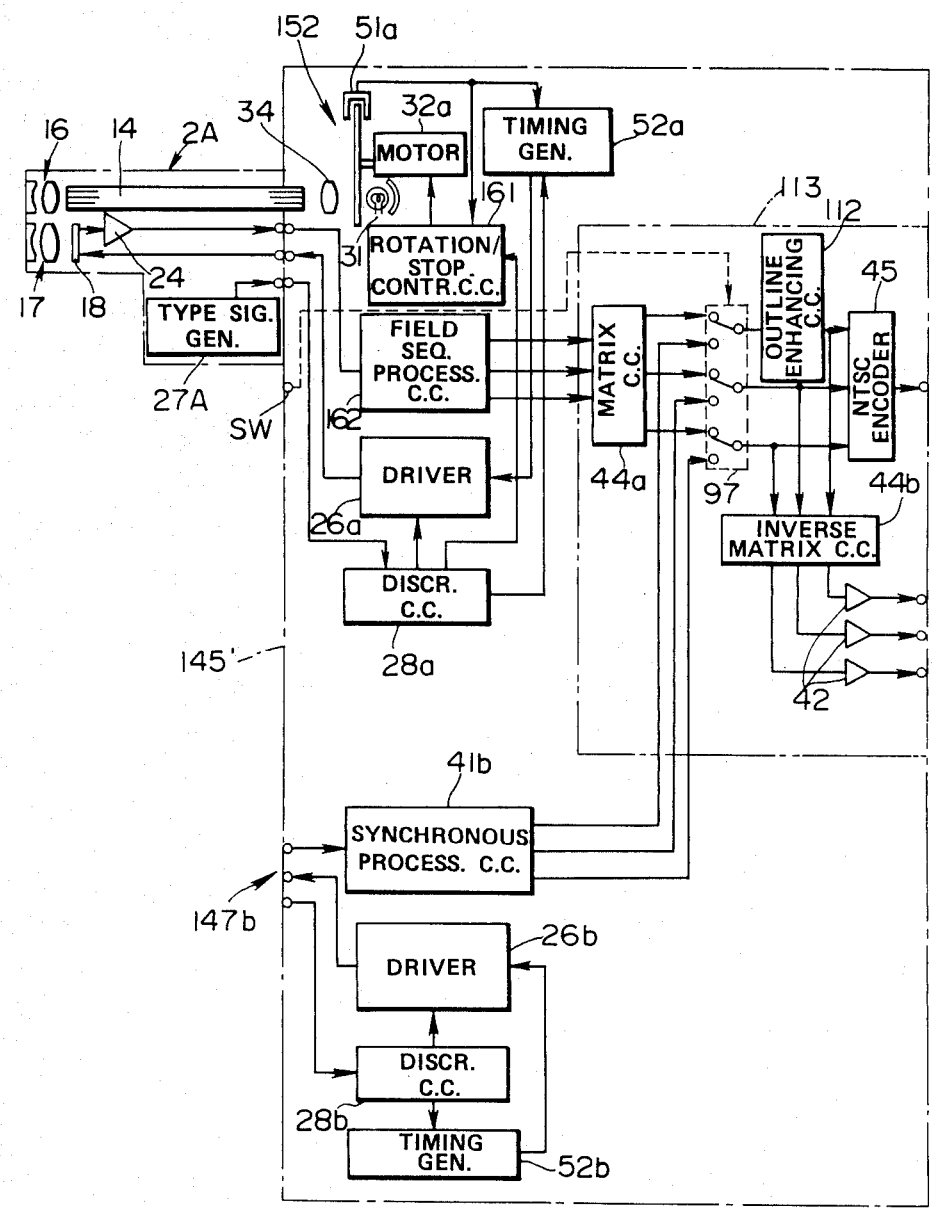

Now, the imaging apparatus body of the formation shown in the above mentioned FIG. 19 may be made an imaging apparatus 145; shown in FIG. 27 made integral from the first. Also, the imaging apparatus body 145' shown in FIG. 27 may be an imaging apparatus body 145" shown in FIG. 28 using light source part shown, for example, in FIG. 19.

Figure 28:
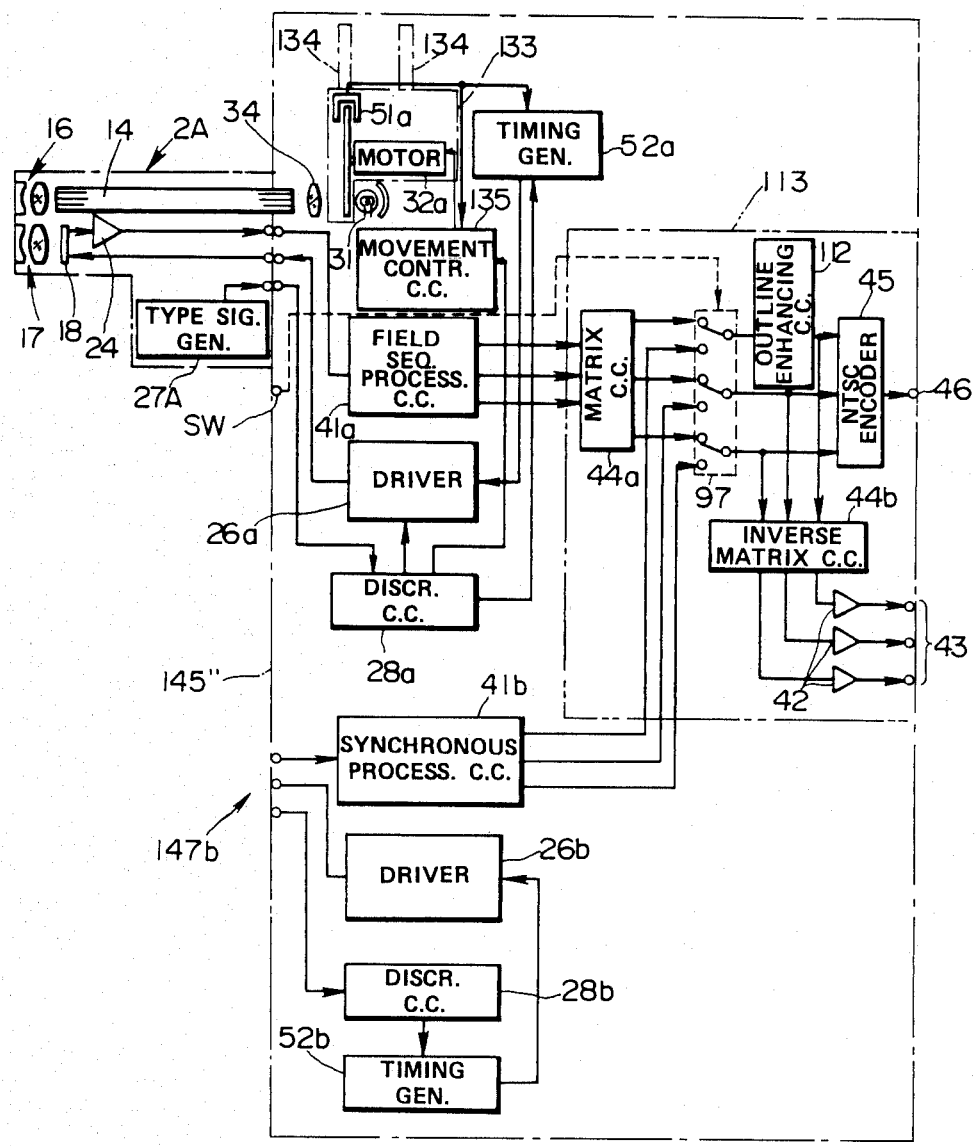

In the above mentioned FIGS. 2 and 28, another signal process than the outline enhancement may be made.

Further, in FIG. 19, the drivers 26a and 26b and discriminating circuits 28a and 28b may be commonly used. The light source part shown in FIG. 19 may be replaced with another formation.

In the apparatus shown in FIG. 19, the synchronous type unit 167 can be used as plugged in and fitted for the field sequential type imaging apparatus body 145 but the field sequential type unit can be also fitted to the synchronous type.

Figure 23:
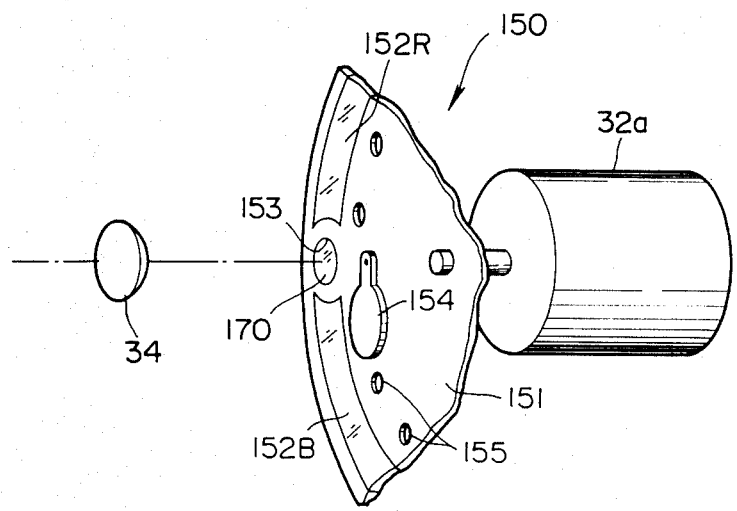
Figure 24:
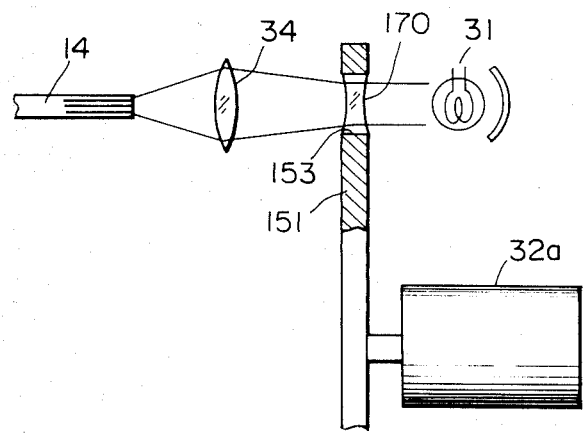

FIGS. 23 and 24 show a modification of the rotary filter 150.

In this example, the rotary filter 150 has a concave lens 170 fitted in the hole 153 of the filter frame 151 shown in FIG. 21. The light source part shown in the cross-section through this hole 153 is as in FIG. 24.

The illuminating light condensed on the light guide fiber end surface when illuminated with a white light is defocused by the above mentioned concave lens 170 so that the light guide fibers may not be burnt and lost. In case the concave lens is not fitted, that is, in case the light is passed through the filter, the illuminating light will be focused on the light guide fiber end surface. In such a case, the light will be reduced by the filter and therefore the light guide fiber end surface will be hardly burnt and lost. In the case of the illumination with a white light by moving in the optical axial direction the lens 34 or light source lamp 31 (on rails) without fitting the concave lens 170, the illuminating light will be defocused but, as in the case of the field sequential type, the illuminating light will be set as focused.

Figure 25:
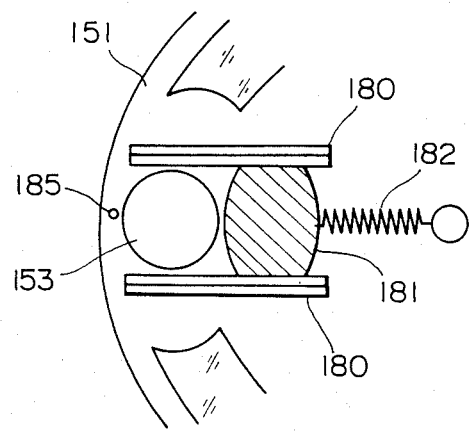

FIG. 25 shows another modification of the rotary filter. In this example, two sliding plates 180 are extended in the radial direction of the filter frame 151 on both sides of the rotary direction of a hole 153 provided in the filter frame 151. A light intercepting plate 181 of a size capable of covering the above mentioned hole 153 is fitted slidably in the radial direction of the filter frame 151 between these sliding plates 180. This light intercepting plate 181 is fixed to the other end of a spring 182 fixed at one end to the above mentioned filter frame 151 on the side nearer to the center than this light intercepting plate 181 and is energized toward the center by this spring 182. A stopper pin 185 regulating the outward movement of the above mentioned light intercepting plate 181 is provided on the radial outside of the filter frame 151 of the above mentioned hole 153.

When the filter frame 151 is rotated by the motor 32a, the above mentioned light intercepting plate 181 will move radially outward of the filter frame 151 against the energizing force of the above mentioned spring 182 under a centrifugal force so as to intercept the above mentioned hole 153 so that the ordinary frame sequential illumination of R, G and B may be made.

On the other hand, when the above mentioned filter frame 151 is stopped, no centrifugal force will act and therefore, a shown in FIG. 25, the light intercepting plate 181 will be moved radially inward of the filter frame 151 by the above mentioned spring 182 and will retreat from the above mentioned hole 153.

FIGS. 29 to 39 show the sixth embodiment of the present invention.

Figure 29:
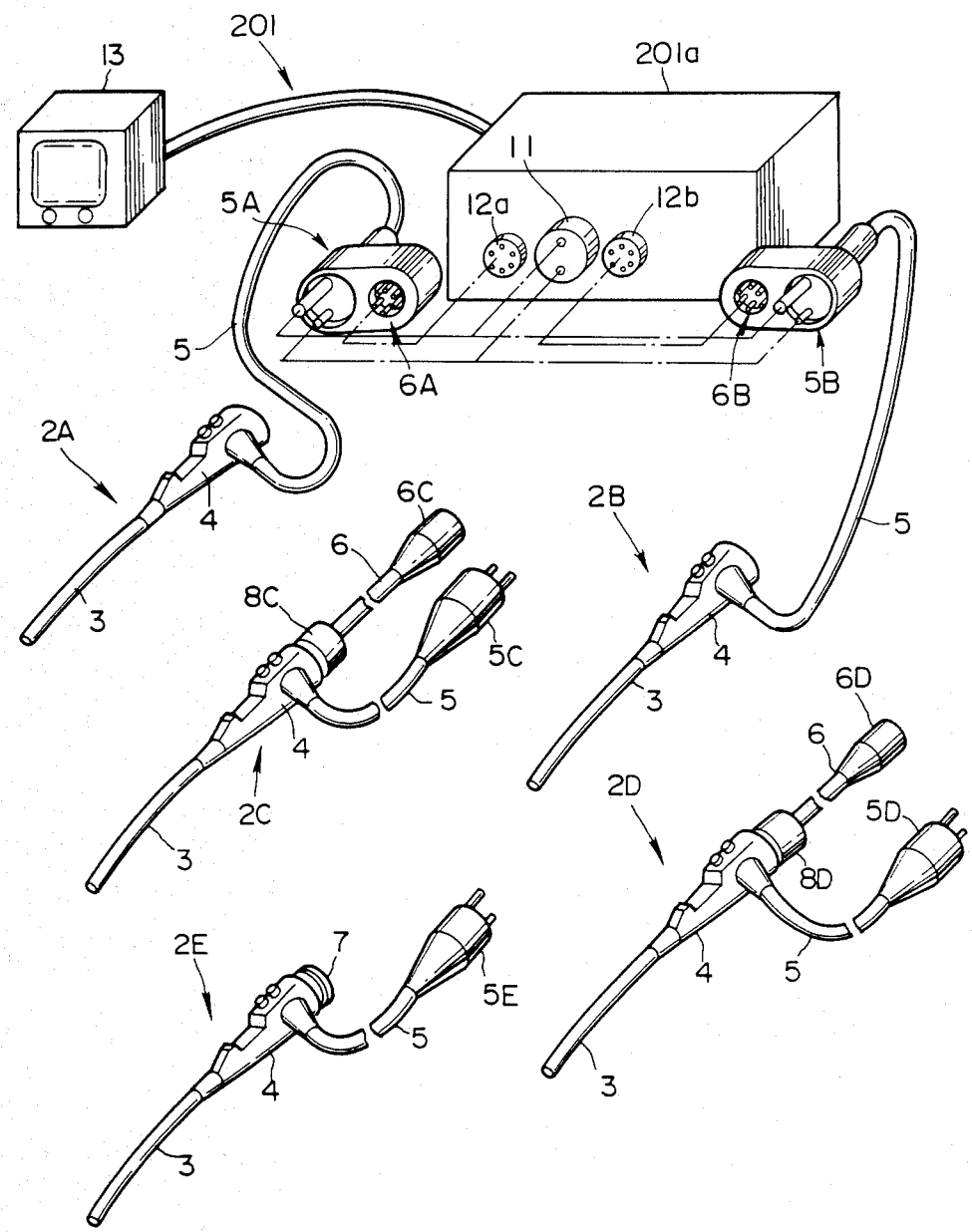

As shown in FIG. 29, in an endoscope apparatus 201 of this embodiment, in the field sequential type electronic scope 2A and synchronous type electronic scope 2B, signal connector 6A and 6B are integrally provided in addition to the light source connectors 5A and 5B on the tip sides of the universal cords 5. In the fiber scope 2C fitted with the field sequential type television camera and fiber scope 2D fitted with the synchronous type television camera, the field sequential type television camera 8C and synchronous type television camera 8D are respectively fitted to the eyepiece part 7 of the fiber scope 2E. The signal connectors 6C and 6D are provided at the tips of the signal cables 6 extended out of the respective television cameras 8C and 8D.

In this embodiment, the light source connectors 5A, 5B, 5C, 5D and 5E of the above mentioned respective scopes 2A, 2B, 2C, 2D and 2E are of the same shapes so as to be connectable to common connector receptacles.

So that the connectors 5A, 6A; 5B, 6B; 5C, 6C; 5D, 6D; 5E of the above mentioned respective scopes 2 may be connected and the respective scopes 2 may be set so as to be usable; for example, on the front surface of the housing of the imaging apparatus body 201, there are provided a light source connector receptacle 11 common to all the scopes 2 and a field sequential type signal connector receptacle 12a and synchronous type signal connector receptacle 12b adjacent, for example, on both right and left sides to this light source connector receptacle. The above mentioned light source connector receptacle 11 is of a form that can be connected with any of the light source connectors 5A, 5B, 5C, 5D and 5E of the sam form of the above mentioned respective scopes 2.

The above mentioned field sequential type signal connector receptacle 12a is of a form that can be connected with the respective signal connectors 6A and 6C of the same form of the field sequential type electronic scope 2A and fiber scope 2C fitted with the field sequential type television camera.

On the other hand, the above mentioned synchronous type signal connector receptacle 12b ia form that can be connected with the respective signal connectors 6B and 6D of the same form of the synchronous type electronic scope 2B and fiber scope 2D fitted with the synchronous type television camera.

Figure 30:
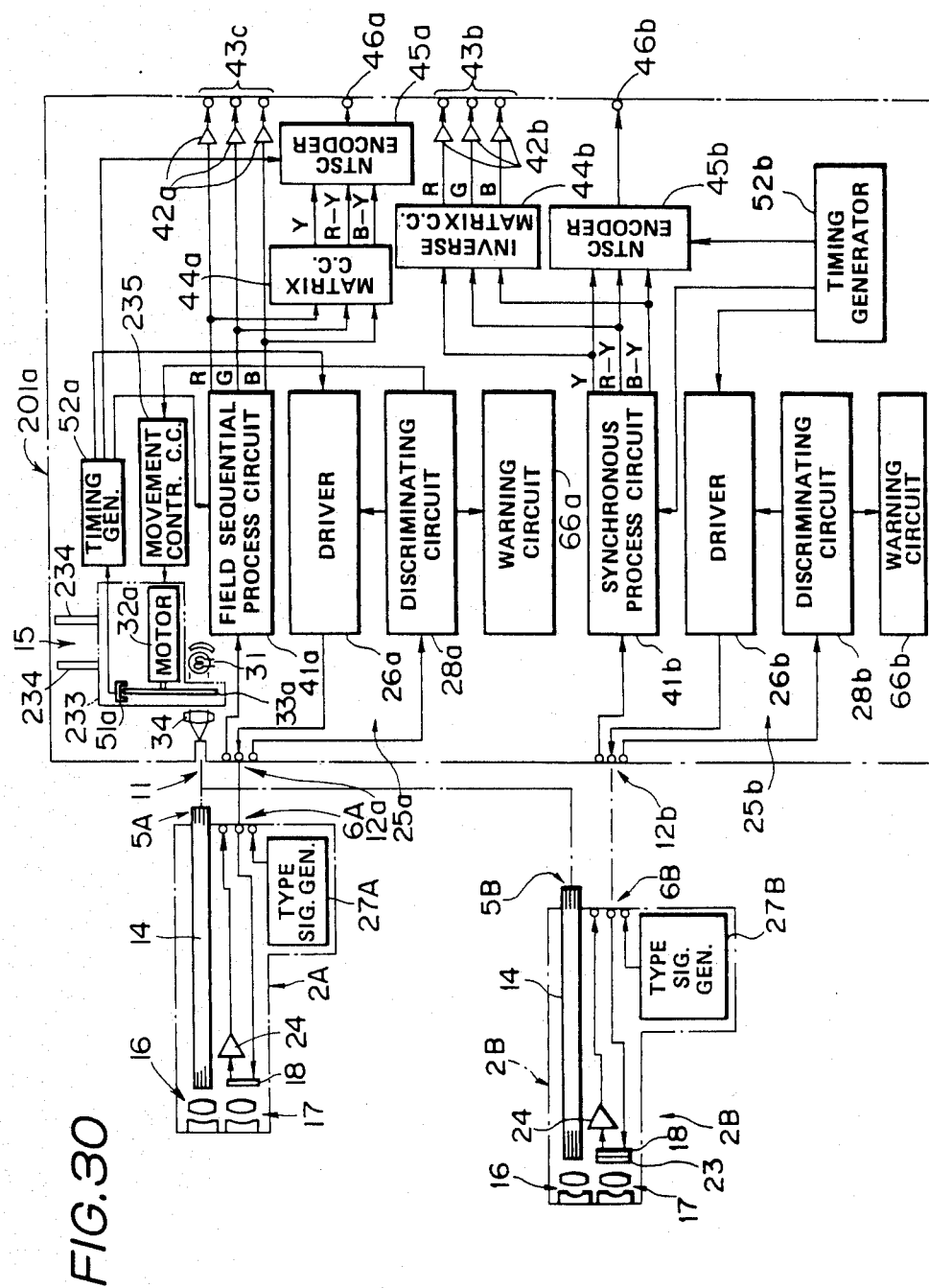

As shown in FIG. 30, the light source apparatus 15 and two sets of video processors 25a and 25b are contained within the imaging apparatus body 201a connectable with any of the above mentioned scopes 2.

In this embodiment, in the above mentioned light source apparatus 15, the light source can be used in common for the field sequential type and the white light.

That is to say, the above mentioned light source apparatus 15 is provided with a light source lamp 31 emitting a white light, a rotary filter 33a arranged in front of this light source lamp 31, having filters transmitting three primary colors of red (R), green (G) and blue (B) and rotated and driven by a motor 32a and a condenser lens 34 arranged in front of this rotary filter 33a. A rotary position sensor 51a detecting the rotary position is provided in one place on the outer periphery of the above mentioned rotary filter 33a.

Figure 31:
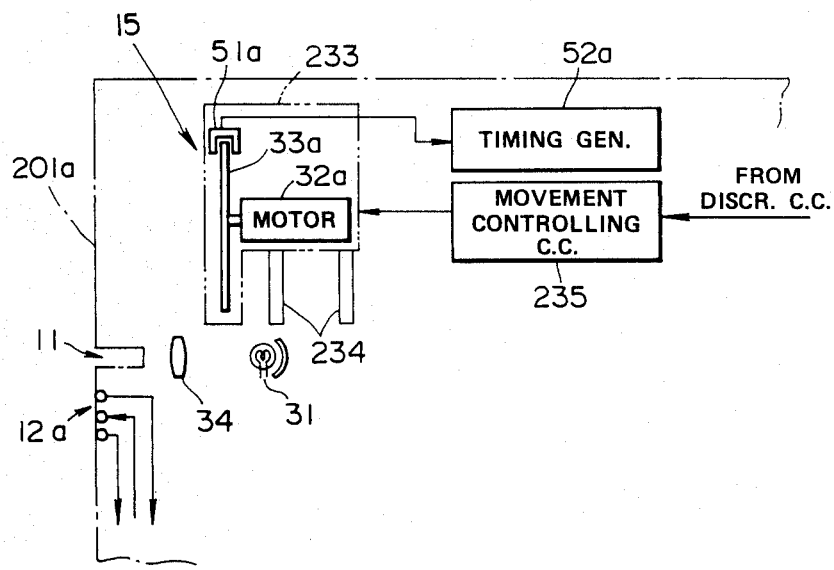
FIGS. 29 to 39 relate to the sixth embodiment of the present invention.

As shown in FIGS. 30 and 31, a rotary filter part 233 consisting of the above mentioned rotary filter 33a, motor 32a and rotary position sensor 51a is movable along rails 234. The above mentioned rotary filter part 233 is set usually in one end part of the rails 234. For example, as shown in FIG. 31, when the rotary filter 33a retreats from the light path between the light source lamp 31 and condenser lens 34, a white light source part will be formed. In this state, the white light emitted from the light source lamp 31 will be condensed by the condenser lens 34 and will enter the entrance end surface of the light guide 14 fitted to the connector receptacle 11. On the other hand, when the rotary filter part 233 is moved to the lower side in the drawing along the rails 234 from this state, as shown in FIG. 30, the rotary filter 33a will be interposed in the course of the light path between the light source lamp 31 and condenser lens 34 to form a field sequential type light source part. In this state, the white light emitted from the above mentioned light source lamp 31 will pass through the rotary filter 33a so as to be made illuminating light of the respective wavelengths of R, G and B in turn, will be condensed by the condenser lens 34 and will enter the entrance end surface of the light guide 14 fitted to the connector receptacle 11.

The above mentioned rotary filter part 233 is controlled in the movement by a movement controlling circuit 235 which is operated by a discriminating signal of the discriminating circuit 208a. That is to say, when the field sequential type scope is identified by a type signal by the type signal generating circuit 27A or 27C, a movement controlling instruction will be output to the movement controlling circuit 235 from the discriminating circuit 28a and the rotary filter part 233 will be moved to the state shown in FIG. 30 from the state shown in FIG. 31. On the other hand, in case the connector of the synchronous type scope 2B or 2D is connected, the rotary filter part 233 will be in the state shown in FIG. 31 and a white light will be fed. Also, in case the fiber scope 2E is fitted, a white light will be fed to the light guide 14 of the fiber scope 2E.

When the field sequential type scope 2A or 2C is fitted and is then removed, the rotary filter part 233 will be returned to the state retreated from the light path of the light source 31 as shown in FIG. 31.

In this embodiment, as the light source connector receptacle 11 is common to all the scopes 2, such misconnection to the connector receptacle of another system as in the case that the light source connector is different depending on the system can be prevented and the operatability is high.

Also, in this embodiment, as the light source part is used in common for the field sequential type and the white light, the field sequential type or synchronous type scope and fiber scope 2E can be coped with without providing two sets of light source parts.

The rotary filter part 233 of the light source apparatus 15 may be manually moved.

The other formations, operations and effects are the same as in the first embodiment.

Figure 32:
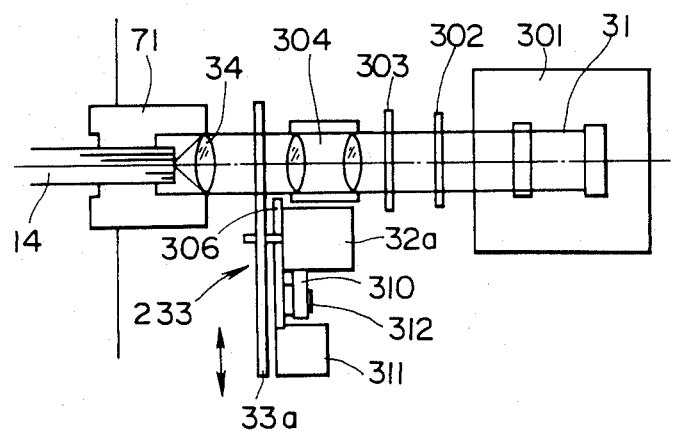
Figure 33:
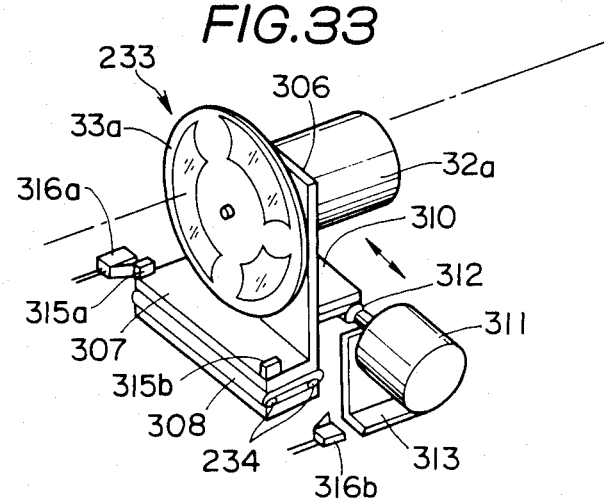
Figure 34:
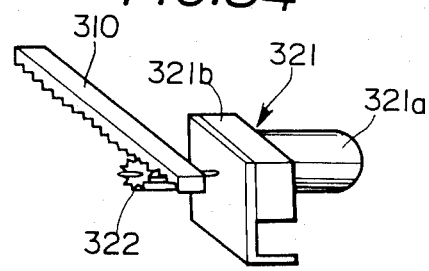

FIGS. 32 and 33 show an example of the concrete formation of a light source apparatus in the sixth embodiment.

As shown in FIG. 32, the white light emitted from the light source lamp 31 contained in a lamp house 301 passes through a cold filter 302, diaphragm 303 and condenser lens 304, then passes through the rotary filter 33a, is condensed by the condenser lens 34 and enters the light guide 14 of the scope fitted to the light source connector receptacle 71.

The above mentioned rotary filter 33a and the motor 32a rotating and driving it are moved by such mechanism as is shown in FIG. 33. That is to say, the above mentioned motor 32a is fitted to a plate-like fitting bracket 306 and a flange part 307 bent in the horizontal direction is formed in the lower part of this fitting bracket 306. Two rails 234 fixed to the housing side of the control apparatus are parallelly provided below this flange part 307. A sliding part 308 in the form holding the rails 234 from the right and left is formed in the bottom part of the above mentioned flange part 307. This sliding part 308 slidably fits the above mentioned rails 234 so that the rotary filter part 233 consisting of the above mentioned rotary filter 33a, motor 32a and rotary position sensor not illustrated may be slidable.

A rack gear 310 is fitted along the moving direction of the above mentioned rotary filter part 233 on the surface on the light source lamp 31 side of the above mentioned fitting bracket 306. A worm gear 312 rotated by the motor 311 is meshed with this rack gear 310. The rotary motor 311 is fixed to the housing side of the control apparatus by a bracket 313. When the above mentioned motor 311 is normally or reversely rotated, the above mentioned rotary filter part 133 will be movable through the above mentioned worm gear 312 and rack gear 310. The above mentioned motor 311 is controlled by the movement controlling circuit 235 shown for example, in FIG. 30. A flat prismatic switch pressing parts 315a and 315b are provided to project on the upper surfaces of both end parts in the moving direction of the flange part 308 of the above mentioned fitting bracket 307. Switching position detecting microswitches 316a and 316b are arranged in the positions pressed by the above mentioned switch pressing parts 315a and 315b at both ends of the moving range of the above mentioned rotary filter part 133. When these microswitches 316a and 316b are pressed by the above mentioned switch pressing parts 315a and 315b, it will be sensed that the above mentioned rotary filter 233 has reached the end of the moving range, the rotation of the above mentioned motor 311 will be stopped and the moving range of the rotary filter part 233 will be regulated. In the illustrated example, when the switch pressing part 315a presses the microswitch 316a, the white light from the light source lamp 31 will pass through the rotary filter 33a, will enter the light guide 14 as a field sequential illuminating light. On the other hand, when the switch pressing part 315b presses the microswitch 316b, the white light from the light source lamp 31 will enter the light guide 14 without passing through the above mentioned rotary filter 33a.

The above mentioned rotary filter pat 233 may be moved by using the rack gear 310 and a pinion 322 meshing with this rack gear 310 and rotated and driven by a gear motor 321 consisting of a motor 321a and reduction gear 321b reducing the speed of the rotation output of this motor 321a.

Figure 35:
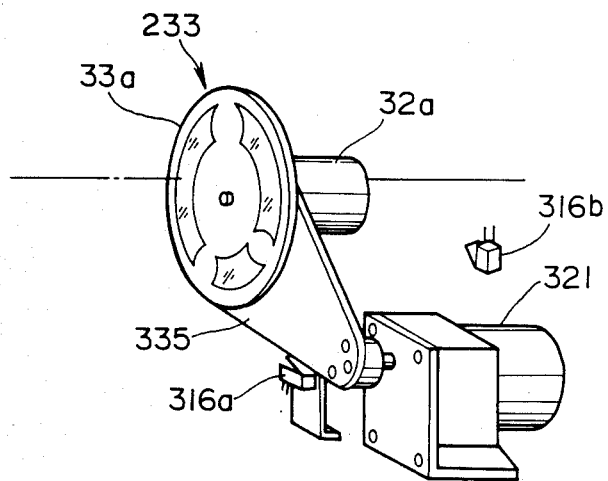

FIG. 35 shows a modification of the moving mechanism of the rotary filter part.

In this example, the rotary filter part 233 is fitted to the expanded diameter side of a substantially fan-shaped fitting bracket 335. The end part on the small diameter side of this fitting bracket 335 is fitted to the output shaft of the gear motor 321. When the above mentioned gear motor 321 is normally or reversely rotated, the above mentioned fitting bracket 335 and the rotary filter part 233 fitted to it will be able to be rotated. Microswitches 316a and 316b sensing that the end of the rotation range has been reached when pressed by the side part in the rotating direction of this bracket 335 are arranged in both end parts of the rotation range of the above mentioned fitting bracket 335. In the illustrated example, when the microswitch 316a is pressed, the white light from the light source lamp 31 will pass through the rotary filter 33a. On the other hand, when the microswitch 316b is pressed, the white light from the light source lamp 31 will enter the light guide 14 without passing through the above mentioned rotary filter 33a.

Figure 36:
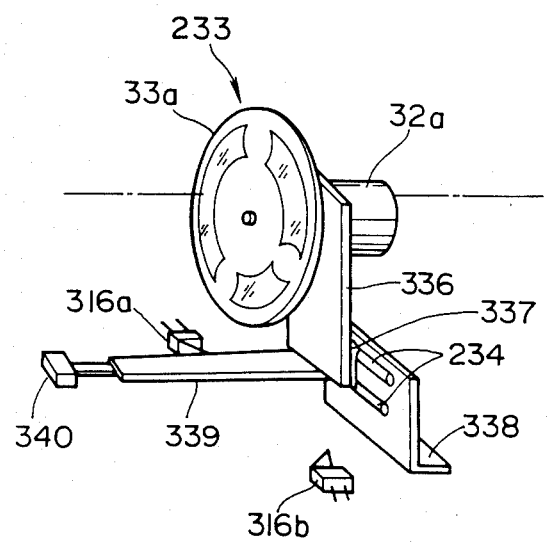

FIG. 36 shows another modification of the moving mechanism of the rotary filter part.

In this example, the rotary filter part 233 is fitted to a fitting bracket 336 and a sliding part 337 slidably fitted to rails 234 fixed to a body fitting bracket 338 fixed to the housing side of the control apparatus is provided on the surface on the light source lamp 31 side of this fitting bracket 336. The rotary filter part 233 fitted to the above mentioned fitting bracket 336 is movable along the above mentioned rails 234. A lever 339 is extended in the advancing direction of the light coming from the light source lamp 31 out of the front surface of the above mentioned fitting bracket 336 and is provided with a grip 340 in the tip part. This grip 340 is projected out of the front surface of the housing, for example, of the control apparatus 201a. When the above mentioned lever 339 is moved in the moving direction of the rotary filter part 233 by gripping this grip 339, the above mentioned rotary filter part 233 will be able to be moved by a manual operation. The microswitches 316a and 316b sensing that the end of the moving range has been reached when pressed by the side part in the moving direction of this lever 339 are arranged in both end parts of the moving range of the above mentioned lever 339. In the illustrated example,, when the microswitch 316a is pressed, the white light from the light source lamp 31 will pass through the rotary filter 33a. On the other hand, when the microswitch 316b is pressed, the white light from the light source lamp 31 will enter the light guide 14 without passing through the above mentioned rotary filter 33a.

Figure 37:
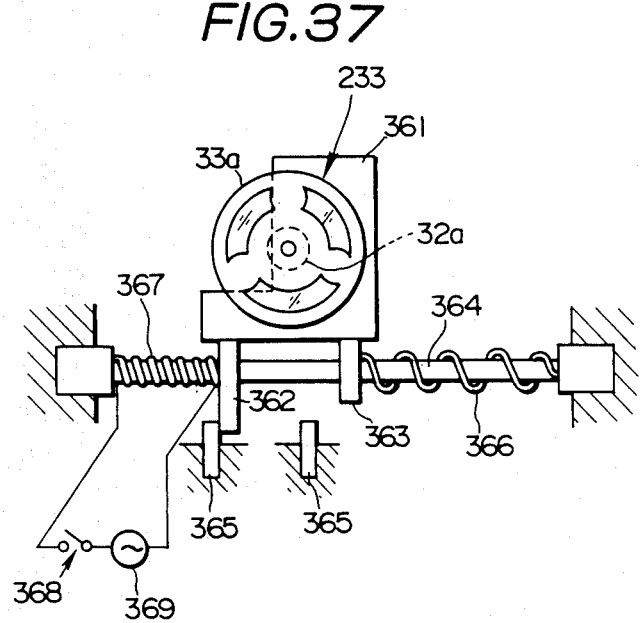

FIG. 37 shows further another modification of the moving mechanism of the rotary filter part 233.

In this example, the rotary filter part 233 is fitted to a fitting bracket 361. Two legs 362 and 363 are provided below this fitting bracket 361. A guide shaft 364 fixed to the housing sides of the imaging apparatus body is passed through these legs 362 and 363. The rotary filter 133 fitted to the above mentioned fitting bracket 361 is movable along the above mentioned guide shaft 364. One leg 362 projects downward to be longer than the other leg 363. Stoppers 365 limiting the moving range of the above mentioned rotary filter part 233 by contacting the leg 362 are provided at a predetermined spacing on both sides of the moving direction of the leg 362. A compression coil spring 366 is externally fitted to the above mentioned guide shaft 364 outside the right side leg 363 in the drawing. This compression coil spring 366 is contacted or fixed at one end to the above mentioned leg 366 and is contacted or fixed at the other end to the housing side of the imaging apparatus body to energize the above mentioned fitting bracket 361 leftward in the drawing. On the other hand, a spring 367 formed of a form memorizing alloy is externally fitted to the above mentioned guide shaft 364 outside the left side leg 362 in the drawing, is contacted or fixed at one end to the above mentioned leg 362, is contacted or fixed at the other end to the housing side of the imaging apparatus body and is connected at both ends with a current source 369 through a switch 368 so that, when the above mentioned switch 368 is closed, the current will be able to be passed through the spring 367. In the above mentioned form memorizing alloy, in the reverse transformation of the martensite phase (low temperature side) to the austenite phase (high temperature side), the deformation in the martensite phase returns to the memorized form in the austenite phase.

The form extended in the austenite phase is memorized in the spring 367 formed of the above mentioned form memorizing alloy. When the spring 367 is electrically heated, it will move the above mentioned fitting bracket 361 rightward in the drawing against the energizing force of the compression coil spring 366.

In this example, when the above mentioned spring 367 is not electrified, the white light from the light source lamp 31 will pass through the rotary filter 33a. On the other hand, when the above mentioned spring 367 is electrified, it will extend, the fitting bracket 361 will be moved rightward in the drawing and the white light from the light source lamp 31 will enter the light guide 14 without passing through the above mentioned rotary filter 33a.

A tension spring energizing the fitting bracket 361 rightward may be provided instead of the above mentioned compression coil spring 366 and the spring 367 of the above mentioned form memorizing alloy may be formed to shrink when it is electrified.

Figure 38:
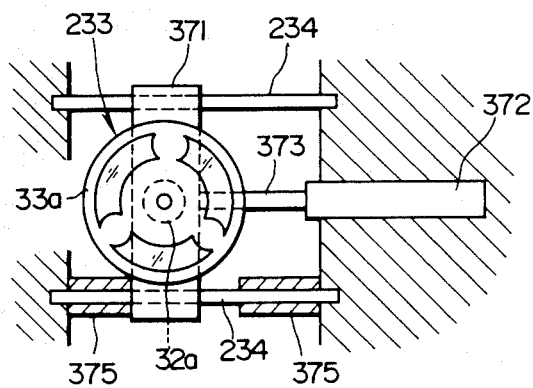

FIG. 38 shows further another modification of the moving mechanism of the rotary filter part.

In this example, the rotary filter part 233 is fitted to a supporting frame 371 which is slidably fitted in the end parts in the vertical direction in the drawing to parallel rails 234 fixed to the housing side of the imaging apparatus body through such auxiliary sliding members as linear ball bearings so that the above mentioned rotary filter part 233 may move along these rails 234. A movable shaft 373 of an air cylinder 372 fixed to the housing side of the imaging apparatus body is fixed at the tip to the subtantially central part of the above mentioned supporting frame 371 so as to be parallel with the moving direction of the above mentioned rotary filter part 233. When the movable shaft 373 of this air cylinder 372 is driven, the rotary filter part 233 fitted to the above mentioned supporting frame 371 will move. One rail 234 is provided with stoppers 375 limiting the moving range of the rotary filter part 233.

A solenoid and plunger may be used in place of the above mentioned air cylinder.

Figure 39:
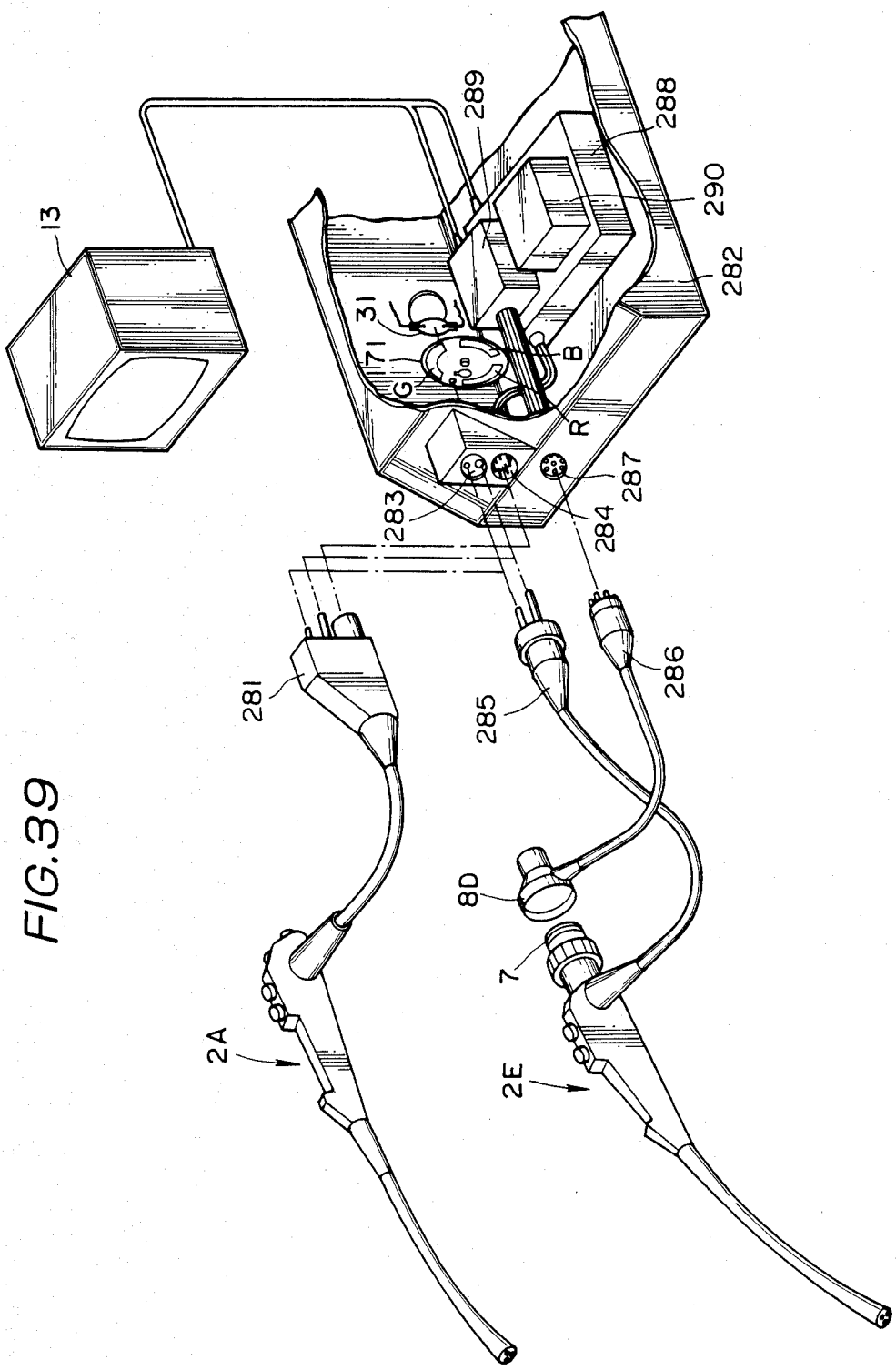

FIG. 39 is a perspective view showing an endoscope apparatus relating to a modification of the sixth embodiment.

In this example, the arrangement of the light source connector receptacle and signal connector receptacle is different from the illustration in FIG. 29.

That is to say, on the front surface of the imaging apparatus body 282, a common light source connector receptacle 283 is provided on the upper side, a field sequential type signal connector receptacle 284 is provided below this light source receptacle 283 and a synchronous type signal connector receptacle 287 is provided below this field sequential type signal connector receptacle 284.

In FIG. 39, for example, the field sequential type electronic scope 2A, fiber scope 2E and mosaic type television camera 8D connectable to this fiber scope 2E are shown.

The connector 281 of the above mentioned field sequential type electronic scope 2A has a light source connector and signal connector made integral and can be connected to the light source connector receptacle 283 and field sequential type signal connector receptacle 284a of the imaging apparatus body 282.

On the other hand, the fiber scope 2E can have its connector 285 connected to the light source connector receptacle 283 for a naked eye observation. For example, the mosaic type television camera 8D is fitted to the eyepiece part 7 to form a scope fitted with the mosaic type television camera and the signal connector 286 of this mosaic type television camera 8D can be used as connected to the mosaic type signal connector receptacle 287.

Though not shown in FIG. 39, the synchronous type electronic scope 2B can be also used. The above mentioned fiber scope 2E as connected with the field sequential type television camera 8C can be also used.

Now, the formation within the imaging apparatus body, 282 is the same as in FIG. 30 and is arranged as shown in FIG. 39.

For example, a field sequential type video processor is contained within a box-like housing 288 on the upper surface of which a housing 289 containing a synchronous type video processor is arranged. A frame memory 290 forming a field sequential type video processor is arranged also on the upper surface of the above mentioned housing 288. A color monitor 13 is connected to the signal output ends of both housings 288 and 289 through signal cables.

A rotary filter 33a and light source lamp 31 are arranged inside the above mentioned light source connector receptacle 283.

Figure 40:
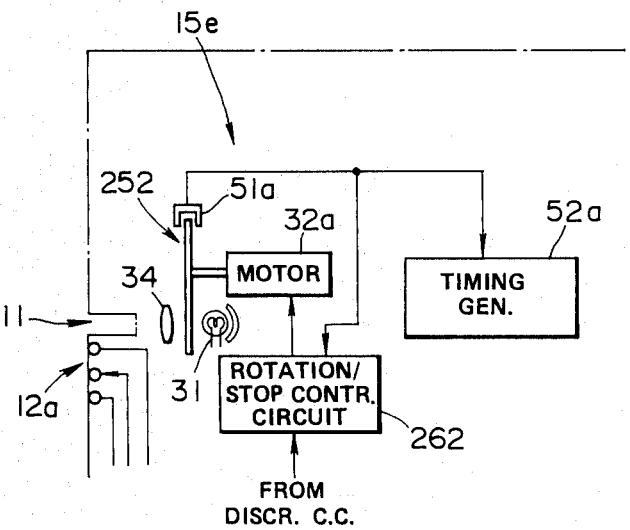
FIGS. 40 to 42 relate to the seventh embodiment of the present invention.
Figure 41:
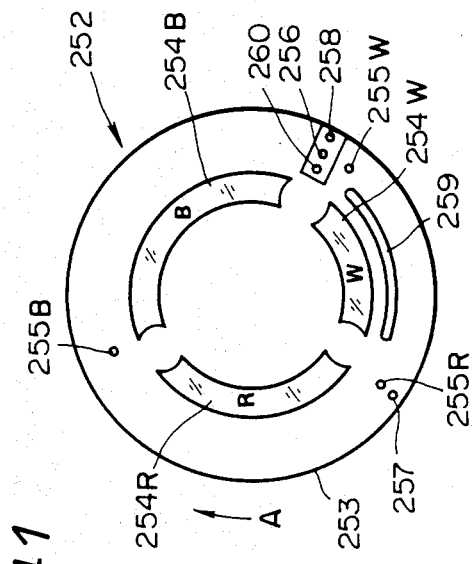
Figure 42:
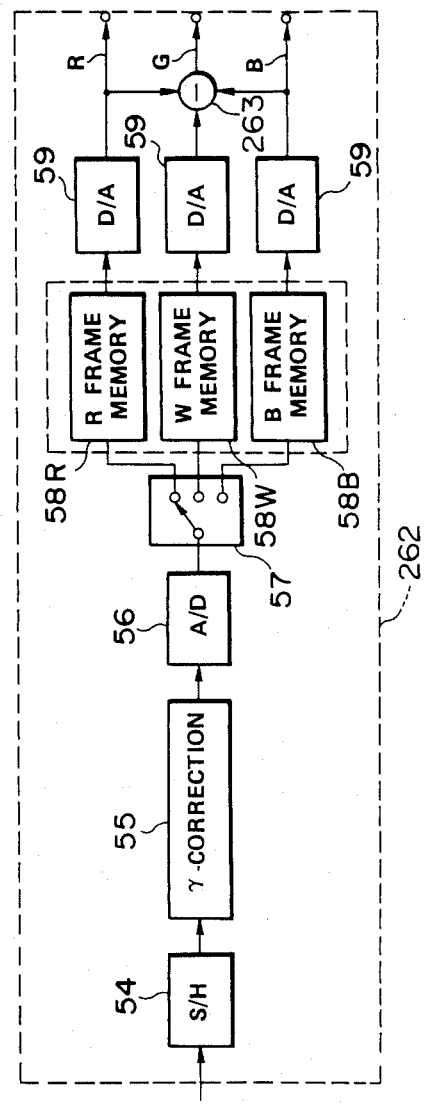

FIGS. 40 to 42 show the seventh embodiment of the present invention.

In this embodiment, the field sequential illuminating light is made of R, W (white) and B instead of R, G and B so that the light source may be commonly used for the field sequential type and white light.

In the light source apparatus 15e contained within the imaging apparatus body 251 in this embodiment, the rotary filter 252 used for the field sequential illumination with the above mentioned illuminating light of R, W and B is provided with fan-shaped window parts in a disc-like filter frame 253 as shown in FIG. 41 and R, W and B color transmitting filters 254R, 254W and 254B respectively transmitting R, W and B are fitted to the respective window parts. This W transmitting filter 254W is a filter transmitting R, G and B. It may be made an approximately transparent plate to transmit all the white light.)

The R, W and B color transmitting filters 254R, 254W and 254B are adjusted in the arcuate lengths so that the illuminating period may be different in response to the photosensitive characteristics of the solid state imaging device 18 or 22.

The above mentioned filter frame 253 is provided with lead pulse (detecting) holes 255R, 255W and 255B respectively near the ends (with respect to the rotating direction A) of the R, W and B color transmitting filters 254R, 254W and 254B so that the lead time just after the illumination respectively with R, W and B may be detected. In case the position opposed to a photosensor 256 arranged as opposed to the light emitting device to hold the filter frame 253 is reached, when the light of the light emitting device is received in the form of a pulse by the photosensor 256, the positions of these lead pulse holes 255R, 255W and 255B will be able to be detected. When this pulse-form light is detected, the detecting signal will be transmitted to the timing generator 52a and a driving pulse for reading out will be applied to the solid state imaging device 18 or 22 through the driver 26a or 26b.

The above mentioned filter frame 253 is provided with a start pulse hole 257 in a position adjacent in the radial direction, for example, to the lead pulse hole 255R. When this position reaches a position opposed to the photosensor 258, the photosensor 258 will output a start pulse.

A slot 259 is arcuately formed in the peripheral outside position of this color transmitting filter 254W in order to detect the position of the W color transmitting filter 254W. The position of the W color transmitting filter 254 can be detected by detecting this slot 259 with the photosensor 260. The stopping position of the rotary filter 252 is controlled by the output of this photosensor 260. That is to say, in case the motor 32a rotating and driving the rotary filter 252 is not rotated and driven, the output of the photosensor 260 will be input into a rotation/stop controlling apparatus 261 and the stopping position of the rotary filter 252 will be controlled so that the stopping position of the rotary filter 252 may be the position in which the slot 259 is opposed to the photosensor 260. In this stopping position, the illuminating light of the light source lamp 31 passes through the W color transmitting filter 254W, is opposed to the light source connector receptacle 11 and can feed a white illuminating light. When a fiber scope is connected to the connector receptacle 11 but nothing is connected to the connector receptacles 12a and 12b or when nothing is connected to the connector receptacles 11, 12a and 12b (both of these states will be able to be discriminated when the high impedance state is sensed by the discriminating circuit) or when the synchronous type scope is connected, this white illuminating state will be made.

On the other hand, when the field sequential type scope is connected, the connection will be sensed by the discriminating circuit 28, a motor 32a rotating and driving instruction signal will be output to the rotation/stop controlling circuit 262, the motor 32a will be rotated and driven and a field sequential illuminating state will be made.

Also in this embodiment the same as in the sixth embodiment, the light source connector receptacle 11 of the imaging apparatus body is commonly used for the white light and field sequential type.

Now, in this embodiment, as the illuminating light is not of R, G and B, the field sequential process circuit 262 is formed as shown, for example, in FIG. 42. That is to say, in the process circuit 41a shown in FIG. 7, the W color signal replaced with the W frame memory 58W instead of the G frame memory 58G (though the memory contents are different, the same frame memory can be used as hardware), further read out of the W frame memory 58W and made an analogue signal by the D/A converter 59 is input into a subtractor 263 and the R color signal and B color signal are subtracted to produce a G color signal. The others are the same as in the process circuit 41a shown in FIG. 7.

In the above mentioned embodiment, the field sequential illumination is made in R, W and G but is not limited to them. For example, the illumination may be made, for example, in R, G, W; W, G, B; Cy (cyanine), Ye (yellow), W; Cy, W, Mg (magenta); W, Ye, Mg.

In this embodiment, the output end may be made common to the field sequential type and synchronous type by using the output circuit 80.

When the fiber scope 2E is connected to the connector receptacle 71 but nothing is connected to the connector receptacle 72, a picture image showing that an observation is being made with a fiber scope may be displayed in the color monitor 13.

Figure 43:
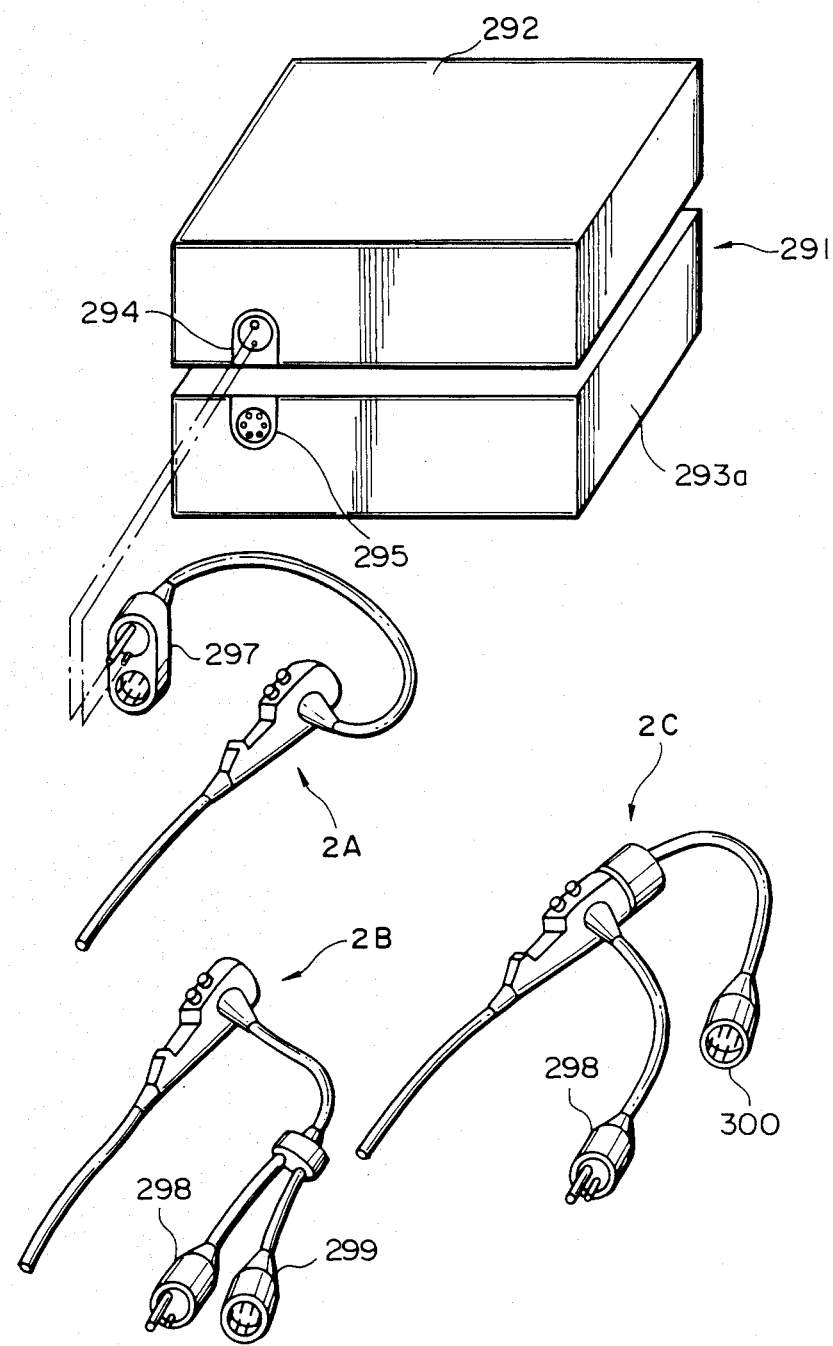
FIGS. 43 to 45 relate to the eighth embodiment of the present invention.
Figure 44:
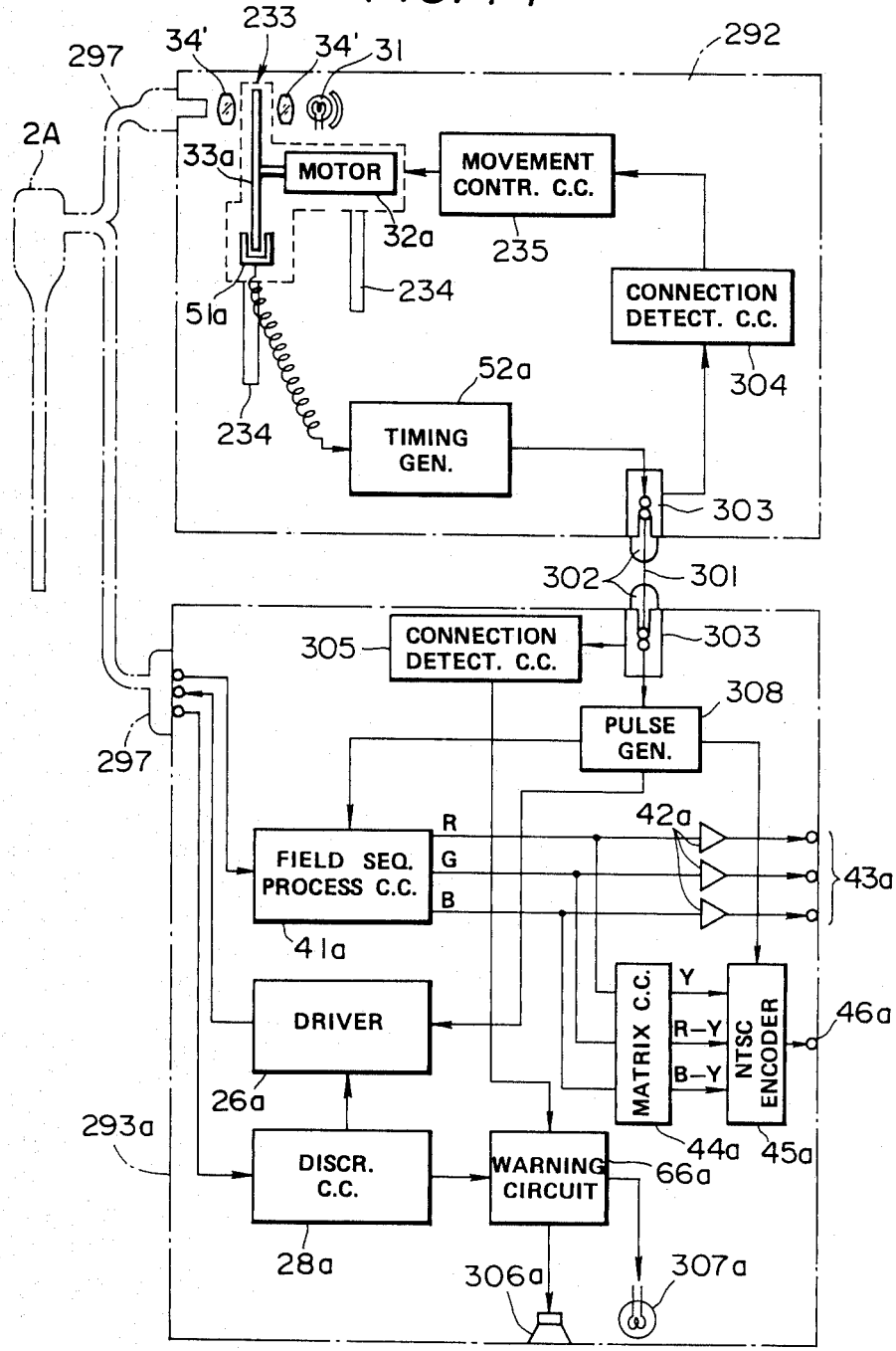
Figure 45:
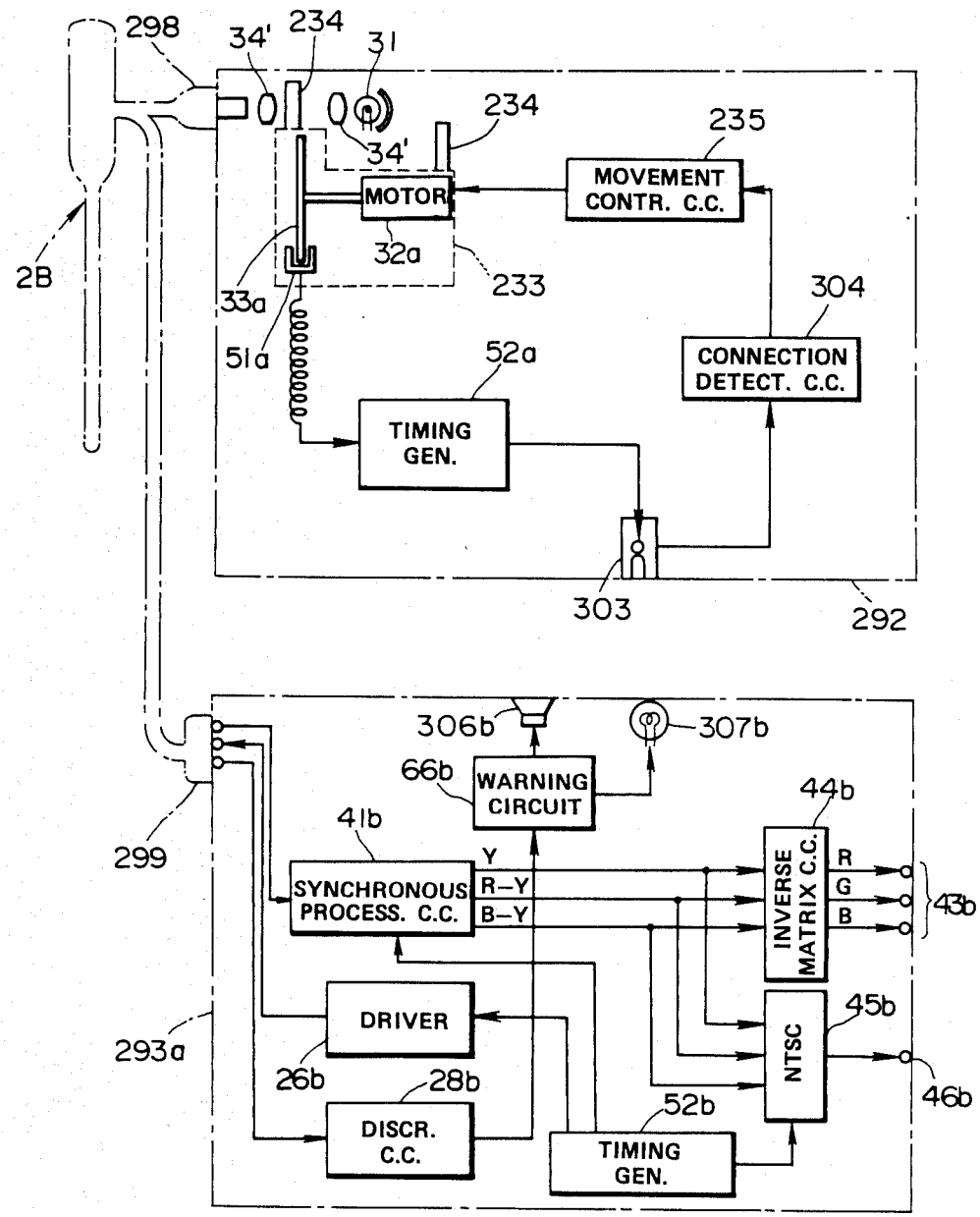

FIGS. 43 to 45 show the eighth embodiment of the present invention.

In this embodiment, the imaging apparatus body 291 is made separate and is formed of a light source apparatus 292 commonly used for all the scopes 2 and a field sequential type video processor part 293a shown in FIGS. 43 and 44 or a synchronous type video processor part 293b shown in FIG. 45. As shown in FIG. 43, a light source connector receptacle 294 common to all the scopes 2 is provided on the lower side of the front surface of the light source apparatus 292. On the other hand, a signal connector receptacle 295 is provided on the upper side of the front surface of each video processor part 293a or 293b. Both these connector receptacles 294 and 295 are provided so as to be vertically adjacent to each other (In FIG. 43, one video processor part 293a is shown) when the light source apparatus 292 is overlapped on the upper surface of the video processor part 293a or 293b.

On the other hand, in the field sequential type electronic scope 2A, the light source connector part and signal connector part of the connector 297 are made integral and can be connected to both connector receptacles 294 and 295 when the light source apparatus 292 is overlapped on the video processor part 293 as shown in FIG. 43.

On the other hand, for example, the connector in the synchronous type electronic scope 2B is divided into a light source connector 298 and signal connector 299 which can be connected respectively to the connector receptacles 294 and 295. Also, for example, in the fiber scope 2C fitted with the field sequential type television camera, the light source connector 298 and signal connector 300 can be connected respectively to the connector receptacles 294 and 295.

Now, in the above mentioned light source apparatus 192, the same as in the light source apparatus 15 shown in FIG. 30, the rotary filter part 233 is made movable and the light source lamp can be commonly used for the field sequential type and white light.

The lens 34 is FIG. 30 is made two lenses 34' in this embodiment.

This light source apparatus 292 is provided with a connector receptacle 303 connecting one of the connectors 302 of a cable 301 for transmitting the timing pulses of the timing generator 52a to a separate field sequential type video processor part 293a and also the field sequential type video processor 293a is provided with the connector receptacle 303.

Also, the above mentioned light source apparatus 292 is provided with a connection sensing circuit 304 sensing whether the connector 302 of the signal cable 301 is connected to the connector receptacle 303. As shown in FIG. 44, when the cable 301 is connected, a movement instructing signal will be output to the movement controlling circuit 235 by the output of this circuit 304, the rotary filter 233 will be moved along the rails 234 and the rotary filter 33a will be interposed in the course of the illuminating light path to make a field sequential illumination.

On the other hand, the field sequential type video processor part 293a is also provided with a connection sensing circuit 305 sensing whether the connector 302 of the cable 301 is connected to the connector receptacle 303 and the output of this sensing circuit 305 is input into the warning circuit 66a. When this warning circuit 661 senses from the discriminating circuit 28 that the field sequential type scope 2A or 2D is connected and when a sensing signal showing that the cable 301 is not connected is input from the connection sensing circuit 305, it will be alerted by a warning buzzer 306 and warning light 307 that the cable 301 is not connected. In case the signal connector 299 of the mosaic type scope 2B or 2D is connected to the signal connector receptacle 229, it will be also alerted.

By the above mentioned cable 301, the timing pulse from the light source apparatus 292 outputs a control signal to the driver or the like through the pulse generator 308 within the video processor part 293. The other formations are the same as of the video processor 25a shown in FIG. 30.

The formation of the mosaic type video processor part 293b shown in FIG. 45 is similar to that of the video processor 25b shown in FIG. 30.

The above mentioned video processor part 293b is provided with a warning circuit 66b operated by the output of the discriminating circuit 28b. When the signal connector of the field sequential type scope 2A or 2C is connected to the synchronous type signal connector receptacle 295, the mis-connection will be sensed by the warning circuit 66b and will be alerted by the buzzer 306b or warning light 307b. The others are of the same formation as is shown in FIG. 30.

In case the above mentioned mosaic type scope 2B or 2D or fiber scope 2E is connected, the rotary filter part 233 will not be moved and therefore the white light of the light source lamp 31 will be condensed and radiated to the connector 298 through the lenses 34'.

According to this embodiment, the field sequential type or synchronous type scope or fiber scope can be accommodated with one unit of the light source apparatus 292. Also, the video processor parts 293a and 293b corresponding to the scope used as in the illustrated example can be selected and used as combined with the above mentioned light source apparatus 292 and can be used also in the case of using another video processor not combined with this light source apparatus.

In FIG. 44, the field sequential type electronic scope 2B is shown as connected but the connector 297 is divided for convenience sake.

In the above mentioned embodiment, the connector as integrated as in the case of the field sequential type scope 2A or as divided as in the case of the synchronous scope 2B can be connected.

In FIG. 43, the light source and signal connectors 297 of the field sequential type electronic scope 2A are made integral but may be divided as in the case of the mosaic type electronic scope 2B. On the contrary, the connectors 298 and 299 of the mosaic type electronic scope 2B may be made integral.

The above mentioned connection sensing circuits 304 and 305 had better be there but are not always necessary.

Also, in the above mentioned embodiment, the rotary filter part 233 is movable but the light source lamp 31, lenses 34 and light source connector receptacle 294 may be made movable. A signal increasing and decreasing the light amount of the lamp 31 may be fed to the light source apparatus 292 through a signal line not illustrated from the video processor part 293a and 293b side to automatically adjust the light.

In the light source apparatus 292, the rotary filter part 233 may be manually moved without using the output of the connection sensing circuit 304.

Figure 46:
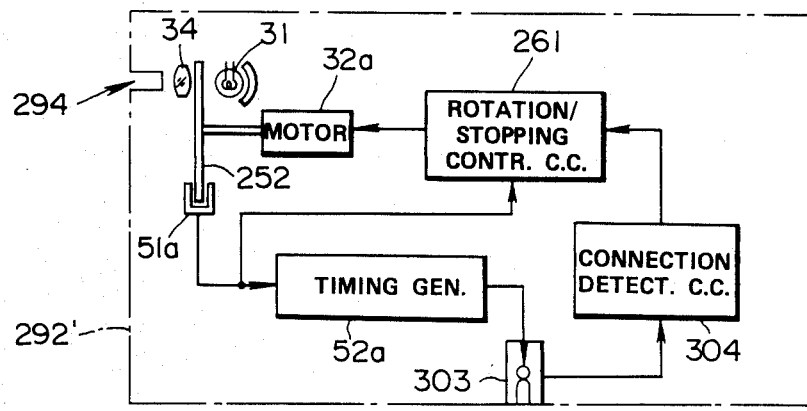
FIG. 46 is a block diagram showing a light source part relating to the ninth embodiment of the present invention.

FIG. 46 shows the ninth embodiment of the present invention.

In this embodiment, the same as in the eighth embodiment, in a light source apparatus 292' separated from the video processor and commonly used for the field sequential type light source and white light source, the rotary filter 252 shown in FIG. 41 is used as a rotary filter of the rotary filter part 233 in FIG. 44 and the rotation/stop is controlled by the rotation/stop controlling circuit 261 (See FIG. 40) without a movable structure. In this case, the field sequential type process circuit 262 shown in FIG. 42 is used instead of the field sequential type process circuit 41a shown in FIG. 44.

Figure 4:
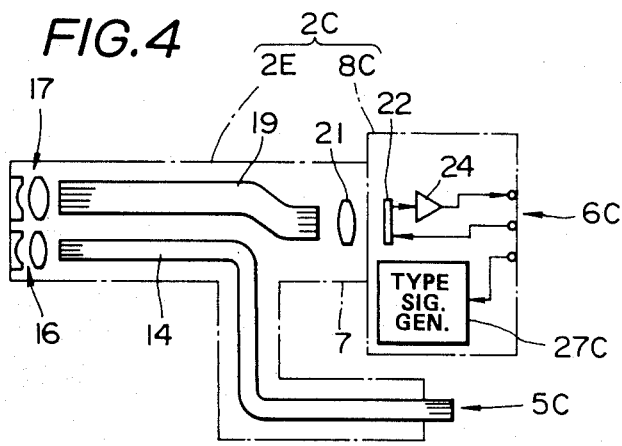
Figure 5:
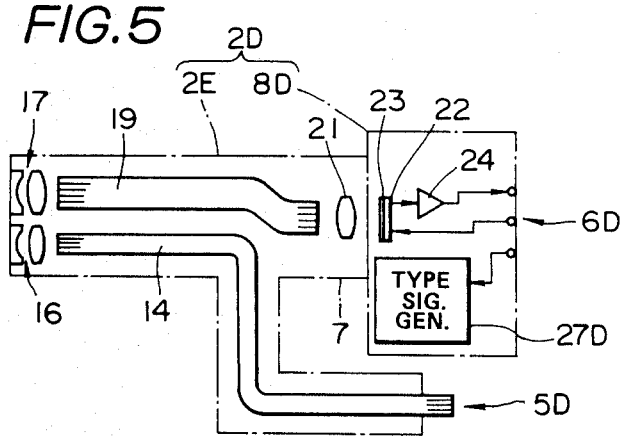
Figure 6:
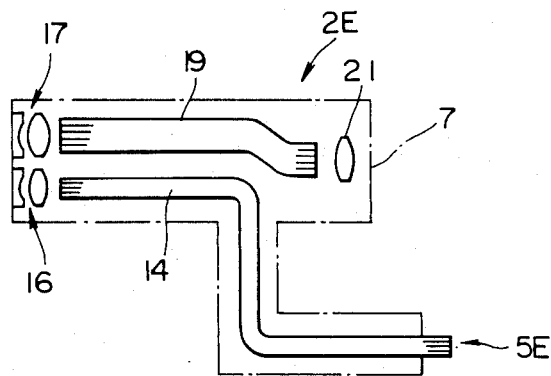

The same as in the eighth embodiment, as shown in FIGS. 4 and 5, this light source apparatus 292' can be used as combined with the field sequential type video processor part 293a and synchronous type video processor part 293b.

According to this embodiment, the same as in the eighth embodiment, the field sequential type or synchronous type scope or fiber scope can be accommodated with one unit of the light source apparatus 292'. No moving means moving the light source part and rotary filter part is required, the cost can be made low and the size can be made small.

In the above mentioned light source apparatus 292', a rotary filter as is shown in FIG. 21, 23 or 25 may be provided instead of the rotary filter 252. However, in this case, the field sequential type process circuit 41a shown in FIG. 44 is used instead of the field sequential type process circuit 262 shown in FIG. 42.

Figure 47:
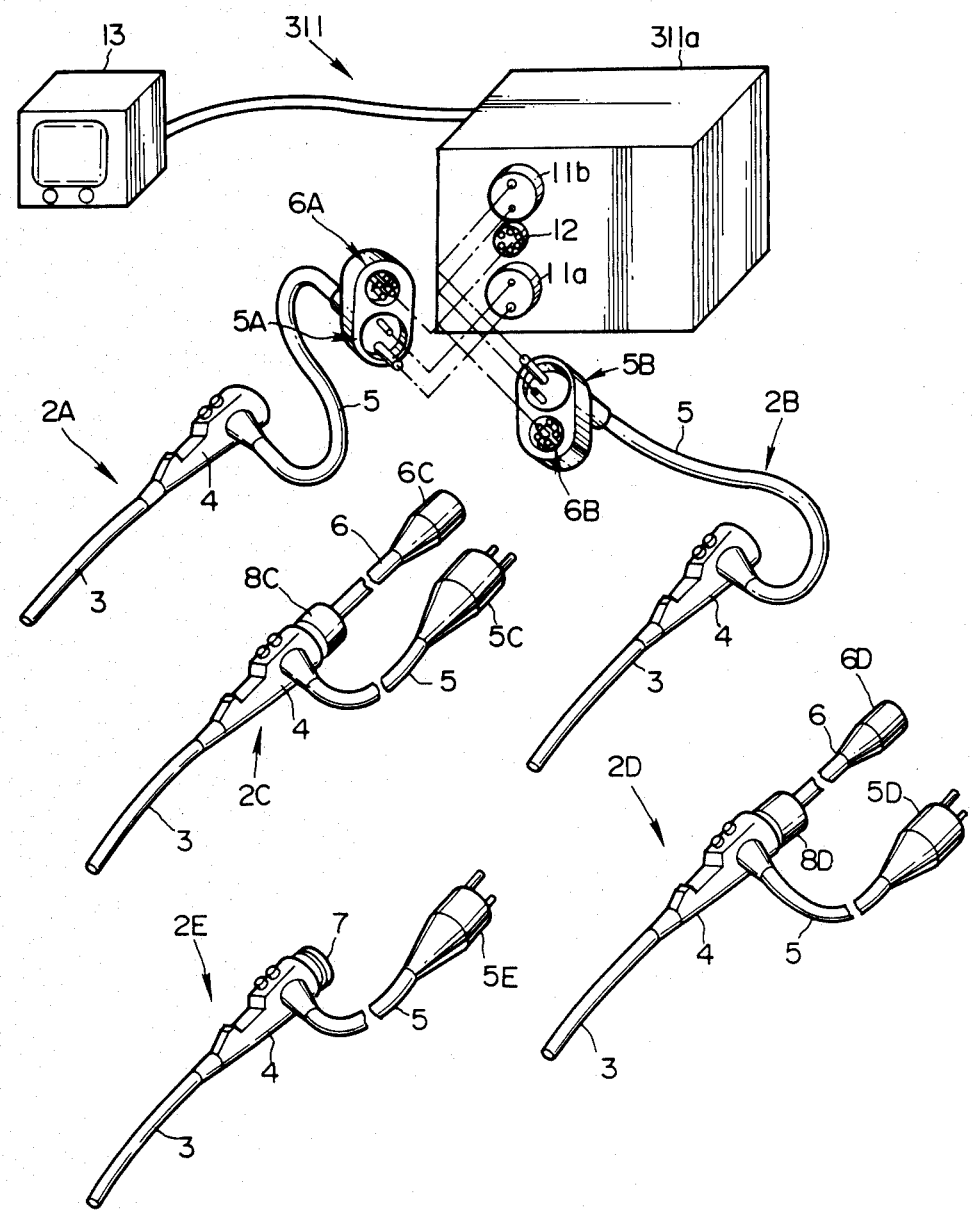
Figure 48:
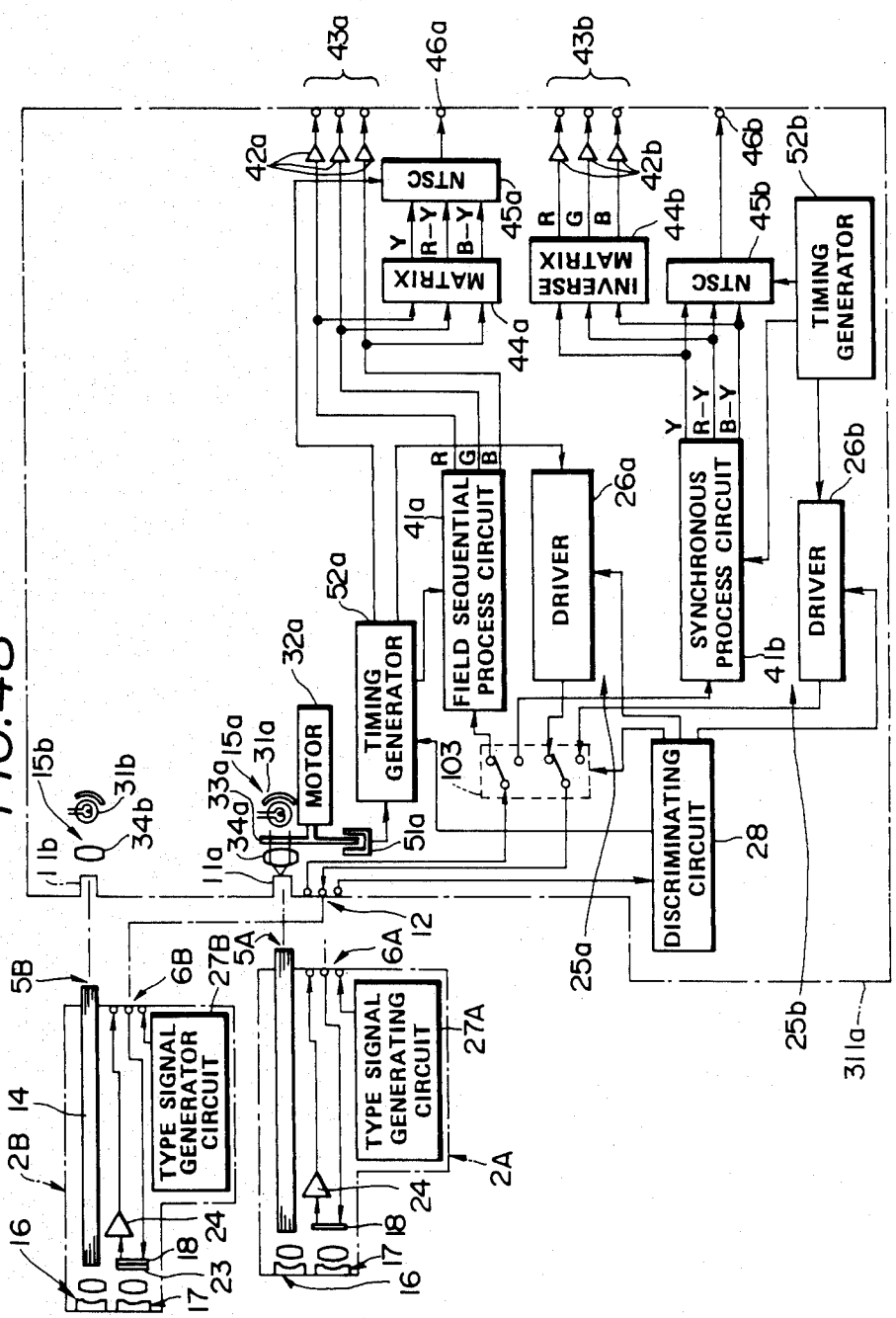

FIGS. 47 and 48 show the tenth embodiment of the present invention.

As shown in FIG. 47, in an endoscope apparatus 311 of this embodiment, in the field sequential type electronic scope 2A and synchronous type electronic scope 2B, the signal connectors 6A and 6BH are integrally provided in addition to the light source connectors 5A and 5B on the tip side. In the fiber scope 2C fitted with the field sequential type television camera and fiber scope 2D fitted with the synchronous type television camera, the field sequential type television camera 8C and synchronous type television camera 8D are respectively fitted to the eyepiece part 7 of the fiber scope 2E and signal connectors 6C and 6D are provided at the tips of the signal cables 6 extend out of the respective television cameras 8C and 8D.

In this embodiment, the signal connectors 6A, 6B, 6C and 6D of the scopes 2A, 2B, 2C and 2D except the fiber scopes 2E are of the same form so as to be connectable to a common connector receptacle.

So that the connectors 5A, 6A; 5B, 6B; 5C, 6C; 5D, 6D; 5E of the above mentioned respective scopes 2A, 2B, 2C, 2D and 2E may be connected to set the respective scopes in a usable state, on the front surface, for example, of the housing of the imaging apparatus 311, there are provided a signal connector receptacle 12 common to the scopes 2A, 2B, 2C and 2E except the fiber scope 2E, a field sequential type light source connector receptacle 11a, for example, vertically adjacent to this signal connector receptacle 12 and a white light source connector receptacle 11b. The above mentioned signal connector receptacle 12 is of a form that can be connected with any of the signal connectors 6A, 6B, 6C and 6D of the same form of the scopes 2A, 2B, 2C and 2D except the fiber scope 2E.

The above mentioned field sequential type light source connector receptacle 11a is of a form that can be connected with the respective light source connectors 5A and 5C of the same form of the field sequential type electronic scope 2A and fiber scope 2C fitted with the field sequential type television camera.

On the other hand, the above mentioned white light source connector receptacle 11b is of a form that can be connected with the respective light source connectors 5B, 5D and 5E of the same form of the synchronous type electronic scope 2B, fiber scope 2D fitted with the synchronous type television camera and fiber scope 2E.

As shown in FIG. 48, two sets of light source parts 15a and 15b and two sets of video processors 25a and 25b are contained within the imaging apparatus body 311a connectable with any of the above mentioned scopes 2.

The formations of the light source parts 15a and 15b are the same as in the first embodiment.

The type signal generating circuits 27A, 27B, 27C and 27D provided in the scopes except the fiber scope 2E are discriminated by the discriminating circuit 28 within the imaging apparatus body 311a through the signal connector 6 and signal connector receptacle.

A field sequential type video processor 25a and synchronous type video processor 25b are connected to the above mentioned common signal connector receptacle 12 through a two-circuit two contact switching switch 103. The above mentioned switching switch 103 is controlled in switching by the above mentioned discriminating circuit 28. That is to say, for example, when the field sequential type scope 2A or 2C is connected, the switching switch 103 will be switched to the field sequential type video processor 25a side but, when the field sequential type scope 2A or 2C is not connected, it will be switched to the synchronous type video processor 25b side. When it is sensed that the synchronous type scope 2B or 2D is connected, the switching switch 103 may be switched to the synchronous type video processor 25b side.

The other formations are the same as in the first embodiment.

In this embodiment, the signal connector receptacle 12 is common to the field sequential type scopes 2A and 2C and synchronous type scopes 2B and 2D. Therefore, such mis-connection as to a connector receptacle of another system in case the signal connector is separate depending on the imaging system can be prevented and the operatability is high.

Further, in this embodiment, the kind of the imaging system of the scope connected to the common signal connector receptacle 12 is discriminated by the discriminating circuit 28 and the connected scope is connected to a video processor 41a or 41b adapted to the imaging system.

The above mentioned switch 103 may be switched to the field sequential type video processor 25a and color mosaic type video processor 25b manually instead of the discriminating circuit 28.

Also, if the light source lamps 31a and 31b of the field sequential type light source part 15a and white light source part 15b are made common and are made switchable to be moved to the positions of the respective light source parts 15a and 15b, both systems will be able to be illuminated with one light source lamp.

Two light source lamps 31a and 31b may be provided on both-sides passing through the center of a rotary plate so that the respective positions may be exchangeable with each other (that is, the light source lamp 31a may be in the position of the light source lamp 31b and the light source lamp 31b may be in the position of the light source lamp 31a) and, even if one light source lamp is broken, the other lamp may be used as an auxiliary lamp.

Also, by using the output circuit shown in FIG. 12 15 or 16, the output end may be made common or such signal processing circuit as for enhancing the outline may be made common.

Figure 49:
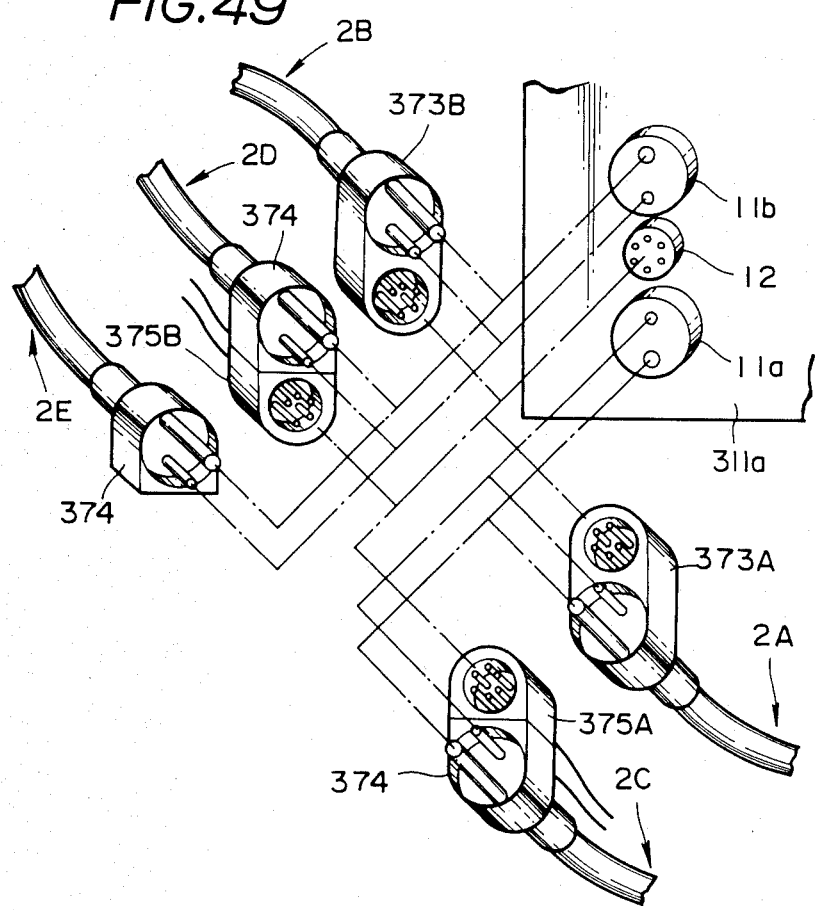
FIGS. 47 to 49 relate to the tenth embodiment of the present invention.

FIG. 49 is a perspective view showing a modification of the connector of the scope 2 in the tenth embodiment.

In the example shown in this drawing, the connector 373A of the field sequential type electronic scope 2A or the connector 373B of the synchronous type electronic scope 2B can have the respective signal connector parts connected to the common signal connector receptacle 12 and the light source connector part can be connected to the light source connector receptacles 11b and 11a provided respectively above and below. Also, the light source connector 374 and signal connector 375A of the scope 2C fitted with the field sequential type television camera or the light source connector 374 and signal connector 375B of the scope 2D fitted with the synchronous type television camera can be respectively made integral. When they are made integral, they will be of the same form as of the connector 373A of the above mentioned field sequential type electronic scope 2A and the connector 373B of the synchronous type electronic scope 2B and will be able to be connected to the above mentioned connector receptacles 12, 11a and 11b. The connector 374 of the fiber scope 2E is in the form which can be made integral with the connectors 375A and 375B of the field sequential type and mosaic type television cameras.

Figure 51:
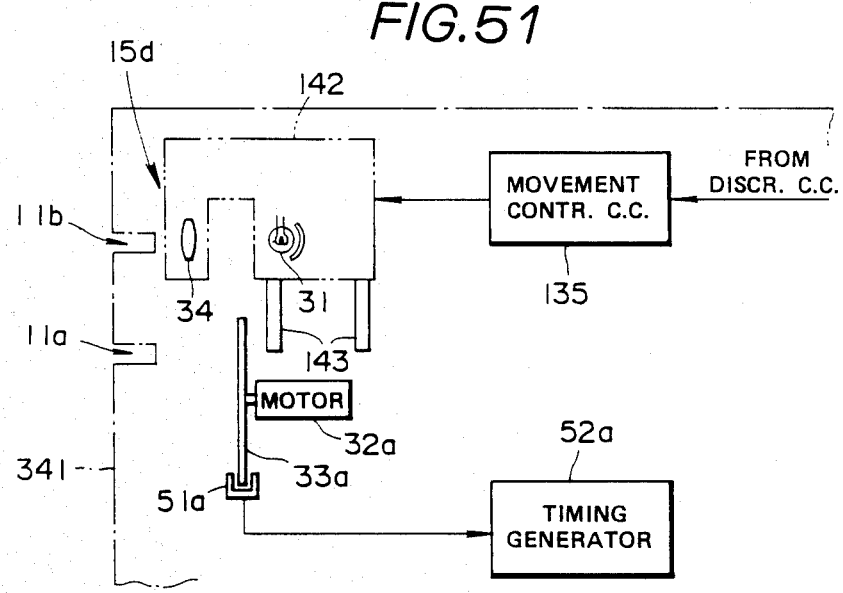
FIGS. 50 and 51 relate to the eleventh embodiment of the present invention.
Figure 50:
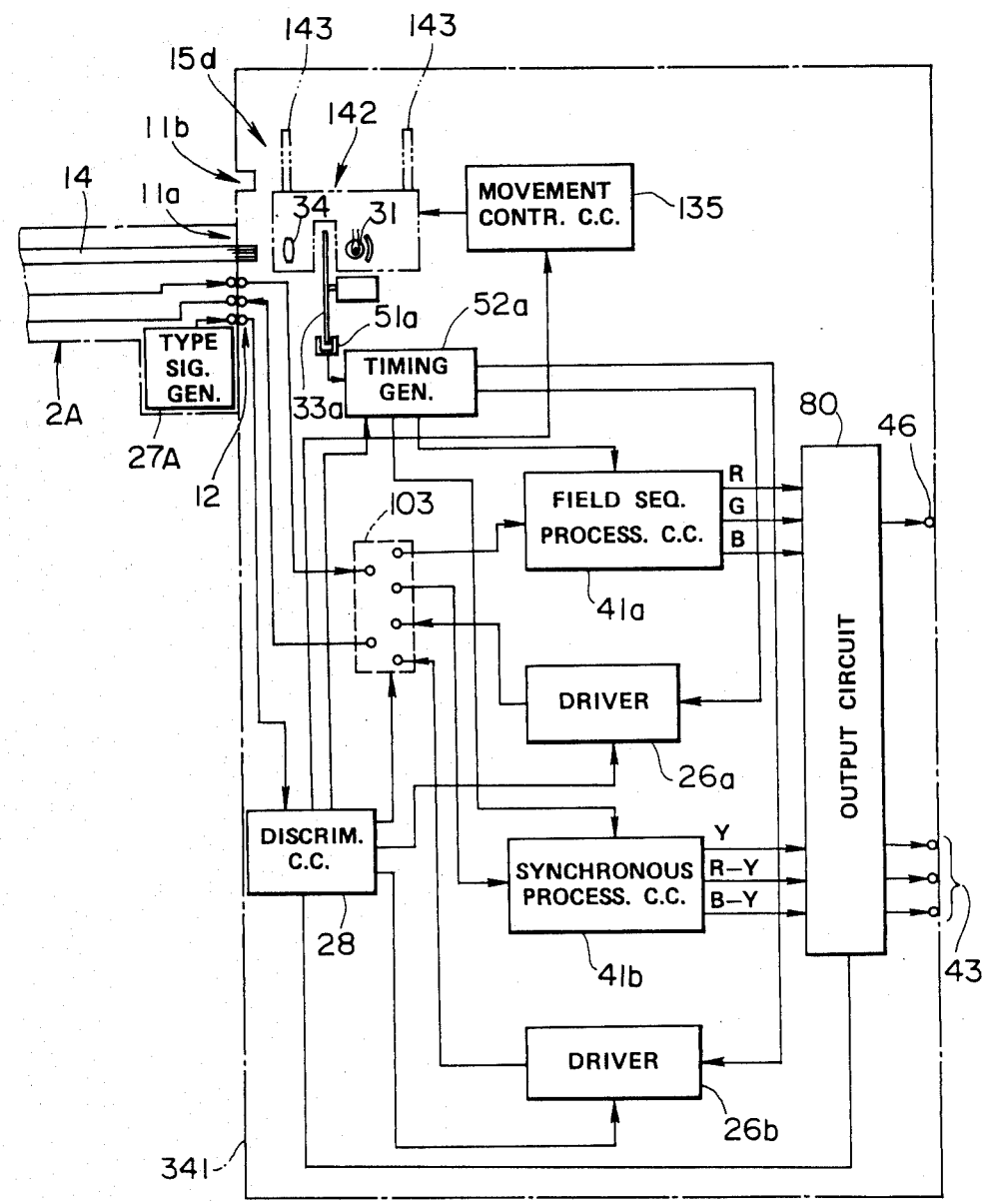

FIGS. 50 and 51 show the eleventh embodiment of the present invention.

In this embodiment, the same as in the fourth embodiment, the field sequential type light source and white light source can be commonly used by moving the light source lamp.

In this embodiment, on the front surface, for example, of the housing of the imaging apparatus body 341. as shown, for example, in FIG. 49, a common signal connector receptacle 12 is provided and a field sequential type light source connector receptacle 11a and a white light source connector receptacle 11b are provided near the common signal connector receptacle 12.

In the light source apparatus 15d contained within the imaging apparatus body 341 in this embodiment, as shown in FIGS. 50 and 51, the light source part 142 consisting of the light source lamp 31 and condenser lens 34 is movable along the rails 143.

The above mentioned light source part 142 is usually set in one end part of the rails 143. When the rotary filter 33a is not interposed in the light path between the light source lamp 31 and condenser lens 34 as shown, for example, in FIG. 51, a white light source part will be formed. In this case, the white light from the above mentioned light source lamp 31 will enter the light guide 14 of the color mosaic type scope 2B or 2D or fiber scope 2E fitted to the light source connector receptacle 11b without passing through the rotary filter 33a. On the other hand, when the light course part 142 is moved to the lower side of the rails 143 from this state, as shown in FIG. 50, the rotary filter 33a will be interposed in the light path of this light source part 143 to form a field sequential type light source part. In this case, the white light from the above mentioned light source lamp 31 will pass through the rotary filter 33a and will enter the light guide 14 of the field sequential type scope 2A or 2C fitted to the light source connector receptacle 11a.

Now, the above mentioned light source part 142 is controlled in the movement by a movement controlling circuit 135 which is operated by the discriminating signal of the discriminating circuit 28. In this embodiment, when a field sequential type scope is identified by the type signal by the type signal generating circuit 27A or 27C, a movement controlling instruction will be output to the movement controlling circuit 135 from the discriminating circuit 28 and the light source part 142 will be moved from the state shown in FIG. 50 to the state shown in FIG. 51.

On the other hand, in case the connector of the synchronous type scope 2B or 2D is connected, the light source part 142 will be in the state shown in FIG. 51 and a white light will be fed. Also, in case the fiber scope 2E is fitted, a white light will be fed to the connector of the fiber scope.

In this embodiment, the signal through the field sequential type process circuit 41a or synchronous type process circuit 41b is output through the output circuit 80 shown, for example, in FIG. 12.

The other formations are the same as in the tenth embodiment.

According to this embodiment, as the light source part is commonly used for the field sequential type and white light, the field sequential type or mosaic type scope or fiber scope can be accommodated without providing two sets of the light source parts.

According to this embodiment, as the signal output end is common to the field sequential type and color mosaic type, it is not necessary to switch the connection of the color monitor 13 or the like depending on the imaging system and the operatability is improved.

The above mentioned light source part 142 may be manually moved.

Also, in this embodiment, the output end may be separate for the field sequential type and mosaic type without using the output circuit 80.

Figure 52:
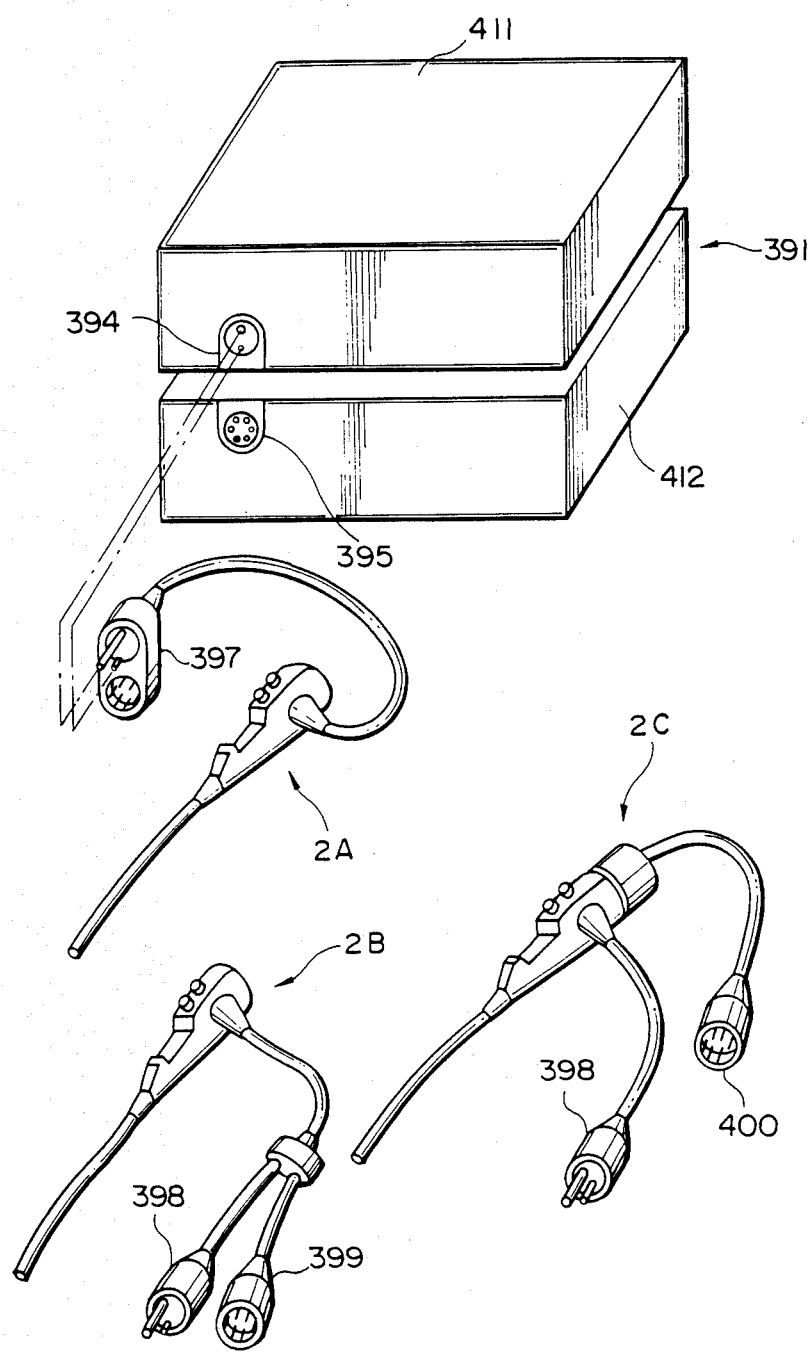
FIGS. 52 and 53 relate to the twelfth embodiment of the present invention.
Figure 53:
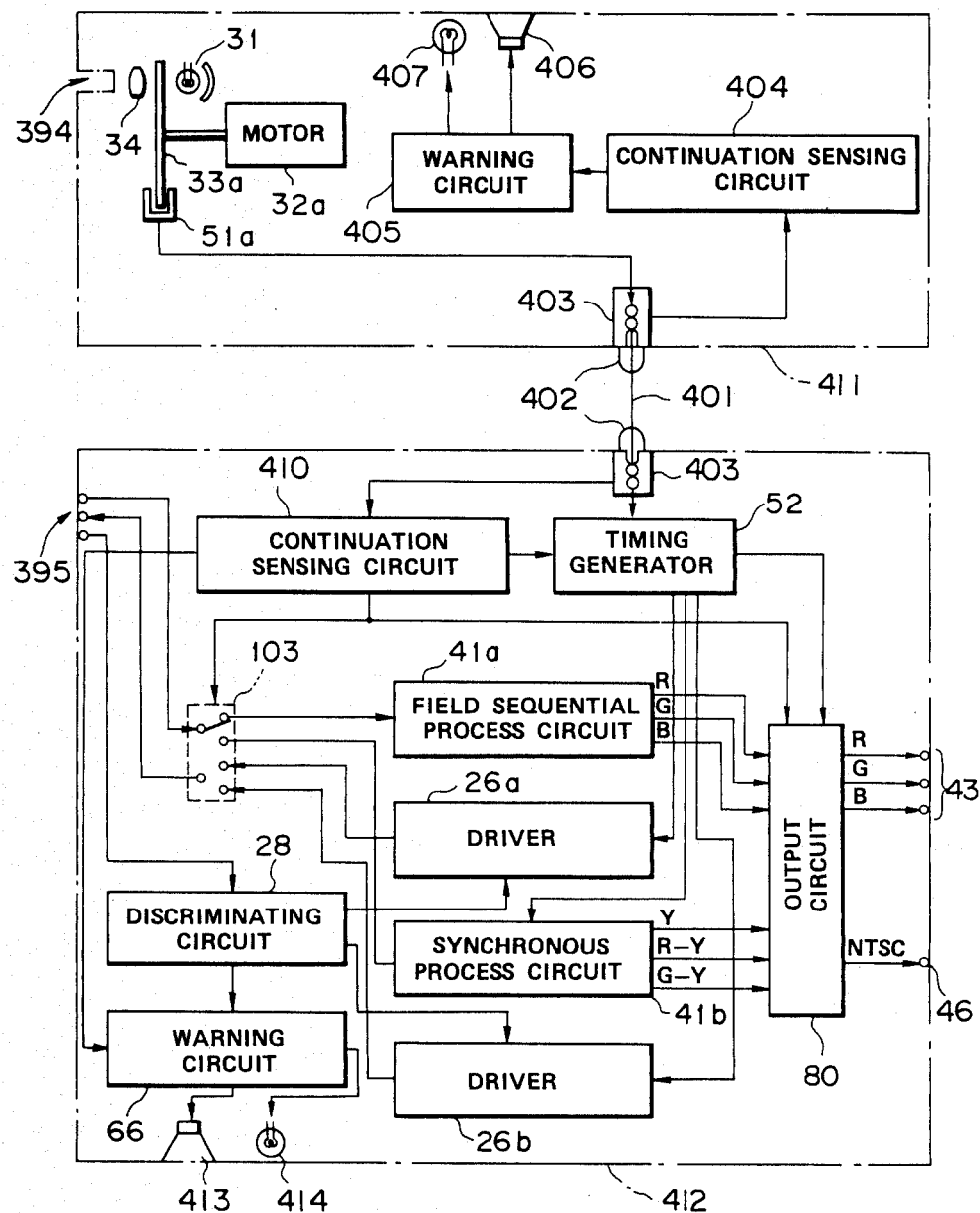

FIGS. 52 to 53 show the twelfth embodiment of the present invention.

In this embodiment, as shown in FIG. 52, an imaging apparatus body 391 is separated into a light source part 411 and video processor part 412.

As shown in FIG. 52, a light source connector receptacle 394 is provided on the lower side of the front surface of the light source part 411. On the other hand, a signal connector receptacle 395 is provided on the upper side of the front surface of the video processor part 412. Both these connector receptacles 394 and 395 are provided so as to be adjacent above and below to each other when the light source part 411 is overlapped on the upper surface of the video processor 412.

On the other hand, on the field sequential type electronic scope 2A, the connector 397 has the light source connector part and signal connector part made integral. As shown in FIG. 52, when the light source part 411 is overlapped on the video processor part 412, both connector receptacles 394 and 395 will be able to be connected with each other.

On the other hand, for example, on the synchronous type electronic scope 2B, the connector is separated into a light source connector 398 and signal connector 399 which can be connected respectively to the connector receptacles 394 and 295. For example, on the fiber scope 2C fitted with the field sequential type television camera, a light source connector 398 and signal connector 400 can be connected respectively to the connector receptacles 394 and 395. Though not illustrated, the fiber scope 2D fitted with the synchronous type television camera can be connected also in the same manner to the above mentioned connector receptacles 394 and 395. The fiber scope 2E can have its light source connector connected to the above mentioned connector receptacle 394.

The above mentioned light source part 411 is separately provided with a field sequential type light source part and white light source part. An example of the field sequential type light source part is shown in FIG. 53. These field sequential type light source part and white light source part are respectively of substantially the same formations as of the field sequential type light source part 15a and white light source part 15b.

The above mentioned video processor part 412 is of substantially the same formation as of the video processor part within the imaging apparatus body 341 shown in FIG. 50. The input end and output end for the signal are made common for the field sequential type and synchronous type.

In this embodiment, a timing generator 52 is provided on the video processor part 412 side. The above mentioned light source part 411 is provided with a connector receptacle 403 connecting one of the connectors 402 of a cable 401 to deliver the output of the rotary position sensor 51a to the timing generator 52 of the video processor part 412. In the same manner, the video processor part 412 is provided with the connector receptacle 403.

Also, the above mentioned light source part 411 is provided with a connection sensing circuit 404 sensing whether the connector 402 of the signal cable 401 is connected to the connector receptacle 403 or not. In the case of illuminating with the field sequential type, if the cable 401 is not connected, a warning by a buzzer 406 driven by a warning circuit 405 or a warning by lighting a lamp 407 will be made by the connection sensing circuit 404.

On the other hand, the above mentioned video processor part 412 is provided in the same manner with a connection sensing circuit 410 sensing whether the connector 402 of the signal cable 401 is connected to the connector receptacle 403 or not and which of the field sequential type light source part and the white light source part is connected. The output of this connecting circuit 410 is input into a warning circuit 44. When the field sequential type light source part 411 and the synchronous type scope 2B or 2D are connected to the video processor part 412 and when the white light source part and the field sequential type scope 2A or 2C are connected to the video processor part 412, a warning by a buzzer 413 driven by the above mentioned warning circuit 66 or a warning by lighting a lamp 414 will be made.

Also, in this embodiment, the switching switch 103 and the switching switches 81 and 82 within the output circuit 80 are switched by the output of the above mentioned connection sensing circuit 410. That is to say, when the field sequential type light source part 411 is connected to the video processor part 412, the above mentioned respective switches 103, 81 and 82 will be switched to the field sequential type side. On the other hand, when the white light source part is connected, the respective switches 103, 81 and 82 will be switched to the synchronous type side. These switches 103, 81 and 82 may be switched manually or by the output of the discriminating circuit 28.

According to this embodiment, with one nit of the video processor part 412, the field sequential type or mosaic type scope can be accommodated and the required light source part can be selected and used.

In this embodiment, the output end may be separate for the field sequential type and mosaic type without providing the output circuit 80.

Also, the output circuit 113 shown in FIG. 15 and the output circuit shown in FIG. 16 may be provided instead of the above mentioned output circuit 80.

As shown in FIG. 18, the light source part 211 may be provided with the field sequential type light source part 15a and white light source part 15b. As shown in FIG. 50, the connector receptacles for the white light source and for the field sequential type light source may be separately provided and the light source lamp 31 may be made movable to be commonly used for the field sequential type and for the white light.

Now, the number of pixels of the solid state imaging device 22 of the television camera 8C or 8D connected to the fiber scope 2E may be larger than the number of pixels of the solid state imaging device 18 of the electronic scope 2A or 2B to improve the resolution. In case the number of pixels of the solid imaging device of the television camera 8C or 8D is thus made larger, the signal processing circuit means corresponding to the number of pixels in the case of the television camera 8C or 8D may be provided.

The number of pixels of each solid state imaging device 18 of the electronic scope 2A or 2B may be the same or different. That is to say, for example, the number of pixels of the field sequential type scope may be made small so that the diameter and size may be small and the number of pixels of the solid state imaging device of the synchronous type scope may be made larger than the number of pixels of the solid state imaging device of the field sequential type scope to elevate the resolution. The number of pixels of each solid state imaging device of the television camera 8C or 8D may be the same or different.

Further, the number of pixels of the solid state imaging device of each of the field sequential type electronic scope 2A and the synchronous type television camera 8D may be the same or different. That is to say, for example, the number of pixels of the solid state imaging device of the field sequential type electronic scope 2A may be made small to make the diameter and size small and the number of pixels of the solid state imaging device of the synchronous type television camera 8D may be made larger than the number of pixels of the solid state imaging device of the field sequential type scope 2A to elevate the resolution. (Even if the television camera is made somewhat larger as it is outside the body, it will have no great influence. It is advantageous to elevate the resolution.) Also, the number of pixels of the solid state imaging device of each of the synchronous type electronic scope 2B and field sequential type television camera 8C may be the same or different.

For example, the field sequential type electronic scope 2A in which the number of pixels of the solid state imaging device or the signal transmitting cable length is different may be provided. In such a case, too, with the discriminating circuit 28, the number of pixels and signal cable length may be discriminated by a type signal from the type signal generating circuit 27 and the manner of driving the driver 26 may be modified to match the number of pixels and cable length. The other scopes 2B, 2C and 2D may be made the same.

In the above described respective embodiments, there may be provided a correcting circuit means correcting the temperature dependency of the light emitting characteristics of the light source lamp 31 or the like.

In response to the characteristics of the fitted scope, a color temperature converting filter may be interposed in the light path of the illuminating light from the light source lamp 31. Thereby, in the case of using the electronic scope, a light beam having the optimum energy distribution can be selected in response to the prismatic characteristics of the solid state imaging device to be used.

In the above described respective embodiments, the signal is transmitted between the scope 2A, 2B, 2C or 2D and the signal processing means through an electric connector means but the present invention is not limited to this. The signal may be transmitted and received by photocoupling. In such a case, a battery may be contained as a current source in the operating part or the like of the scope or the light by the light guide may be fed by a device having a photoelectromotive force such as a solar battery.

A field sequential type and synchronous type television cameras made integral may be fitted to the eyepiece part of the fiber scope 2E and may be used as switched by a switching switch or the like. In this case, together with the switching, the light source side illuminating system and signal processing system are also switched as operatively connected. Thus, for example, the synchronous type is used for the observation of a moving part and, in case an observation with a high resolution image is desired, the field sequential type can be adopted.

The scope capable of naked eye observation is not limited to the fiber scope. A relay lens or the like may be used for the image transmitting means. Further, the present invention can be applied to a scope provided with a field sequential type or synchronous type imaging means in the eyepiece part.

In the above described respective embodiments, the light source is provided outside the scope. However, the present invention can be applied also to a scope containing an LED or the like field-sequentially or synchronously emitting lights in R, G and B.

Different embodiments can be formed by combining parts of the above described respective embodiments and also belong to the present invention.

Figure 54:
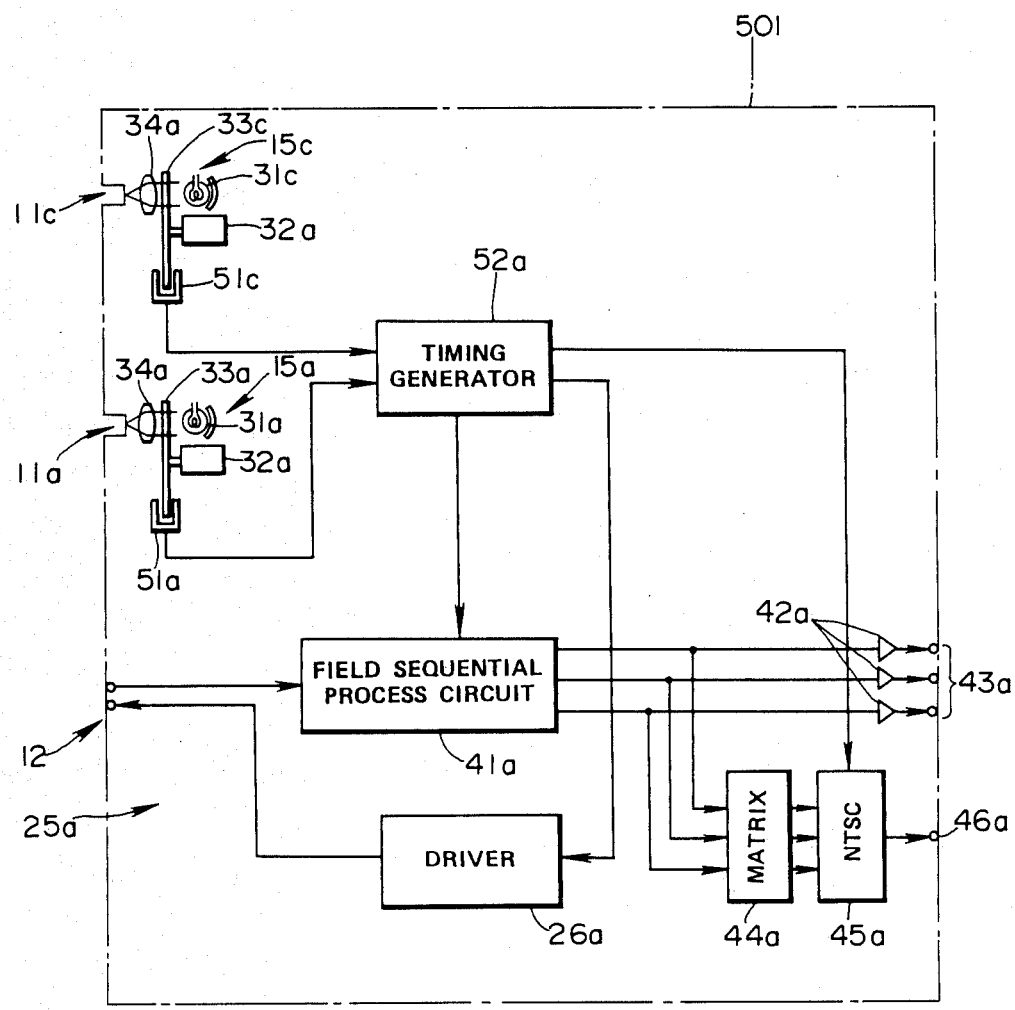
FIGS. 54 to 56 relate to the thirteenth embodiment of the present invention.
Figure 55:
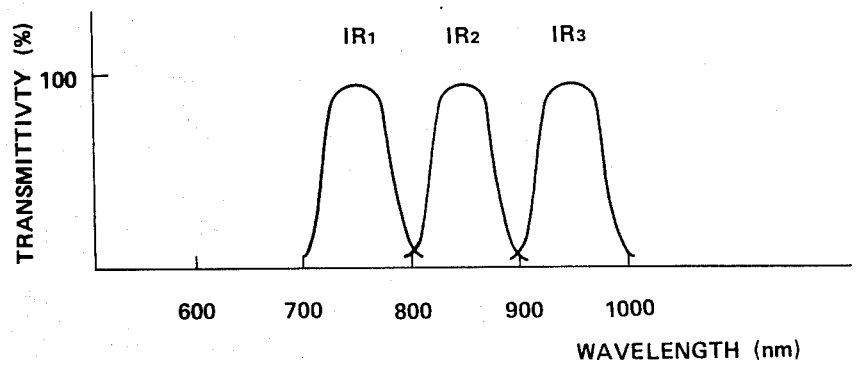
Figure 56:
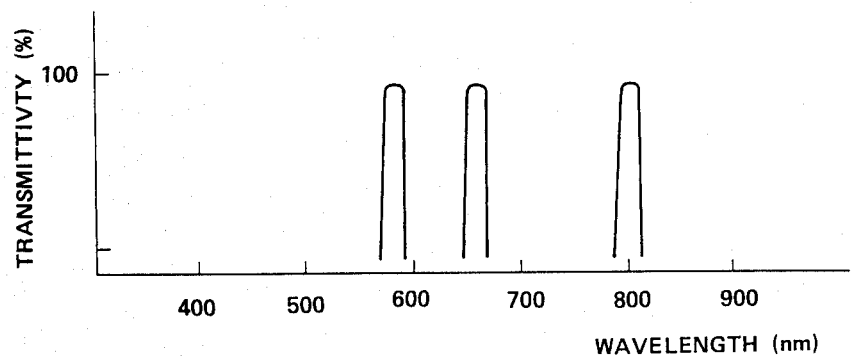
Figure 57:
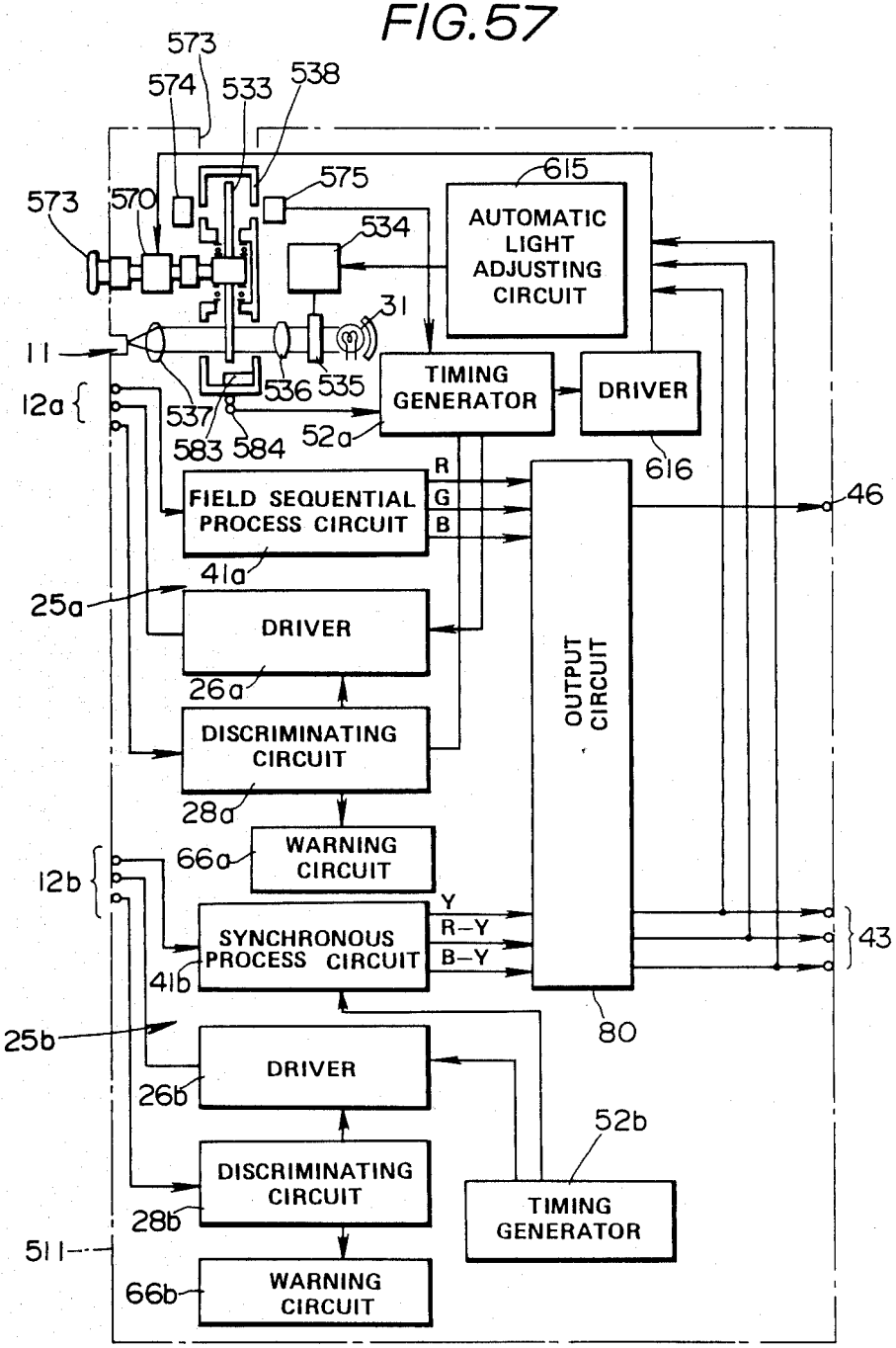
FIGS. 57 to 60 relate to the fourteenth embodiment of the present invention.

FIGS. 54 to 56 show the thirteenth embodiment of the present invention.

In this embodiment, a picture image by different illuminating methods can be obtained by the same imaging system.

An imaging apparatus body 502 of this embodiment has two light source connector receptacles 11a and 11c and one signal connector receptacle 12.

The above mentioned imaging apparatus body 501 is provided with two sets of field sequential type light source parts 15a and 15c emitting illuminating lights from the two light source connector receptacles 11a and 11c and one set of a field sequential type video processor 25a connected to the signal connector receptacle 12.

One light source part 15a is a light source part for obtaining color picture images in an ordinary visible region. The other light source part 15c is a light source part for special picture images. These light source parts 15a and 15c are of substantially the same formation and are different only in rotary filters 33a and 33c. That is to say, the rotary filter 33a for ordinary picture images has color filters separating the light of the visible band into R, G and B arranged in the peripheral direction, whereas the rotary filter 33c for special picture images has three filters transmitting three different wavelength regions in the infrared band as shown, for example, in FIG. 55 or three filters transmitting the lights in three specific narrow bands as shown in FIG. 56 arranged in the peripheral direction. In this case, a light source emitting the light including the transmitted wavelength regions of the respective filters of the rotary filter 33c is used for the lamp 31a of the light source part 15c.

The field sequential type scope for obtaining ordinary color picture images has the signal connector connected to the signal connector receptacle 12 and has the light source connector connected to the light source connector receptacle 11a. In this case, the same as in the other embodiments, the object image illuminated by the field sequential lights of R, G and B is made a video signal by the signal process of the field sequential type video processor 25a.

On the other hand, in the field sequential type scope for obtaining special picture images, the signal connector is connected to the signal connector receptacle 12 and the light source connector is connected to the light source connector receptacle 11c. The field sequential type scope for obtaining special picture images is of substantially the same formation as of the field sequential type scope for obtaining ordinary color picture images. The solid state imaging device may have a sensitivity in the wavelength region (for example, in the infrared band) for forming special picture images. In this case, the field sequential light for forming special picture images as emitted from the light source part 15c will be radiated to the object, the object image by this illuminating light will be made a video signal by the signal process of the above mentioned field sequential type video processor 25a and the object image by a special light will be quasi-color-displayed.

In case the wavelength region shown in FIG. 55 is set as a wavelength region for forming special picture images, the object image in the infrared band will be quasi-color-displayed, the color tone difference difficult to discriminate in a color picture image in the ordinary visible band will be able to be detected and it will be easy to find an affected part or confirm the vein running state.

In case a narrow band near 580 nm, narrow band near 650 nm and a narrow band near 80 nm are set as shown in FIG. 56 as wavelength regions for forming special picture images, the regions near 580 nm and near 800 nm will be regions in which the light absorbing degree of blood is not substantially varied by the oxygen saturated degree (which shall be mentioned as $SO_2$ hereinafter) of the hemoglobin of blood and the region near 650 nm will be a region in which the light absorbing degree of blood is varied by $SO_2$. Therefore, the variation of $SO_2$ can be observed.

The wavelength regions for forming special picture images are not limited to the combinations shown in FIGS. 55 and 56 but may be three different wavelength regions in the ultraviolet band.

Thus, in this embodiment, two kinds of scopes different in the illuminating method can be used in the common imaging apparatus body 501 and the same signal process can be made with the common video processor 25a for two kinds of scopes.

FIGS. 57 to 60 show the fourteenth embodiment of the present invention.

The same as in the imaging apparatus body 201a shown in FIG. 30, an imaging apparatus body 511 of this embodiment has one light source connector receptacle 11 and two signal connector receptacles 12a and 12b. The formation of the video processor side of this imaging apparatus body 511 is substantially the same as of the imaging apparatus body 201a shown in FIG. 30 but an output circuit 80 is used on the output side.

Figures 58, 59:
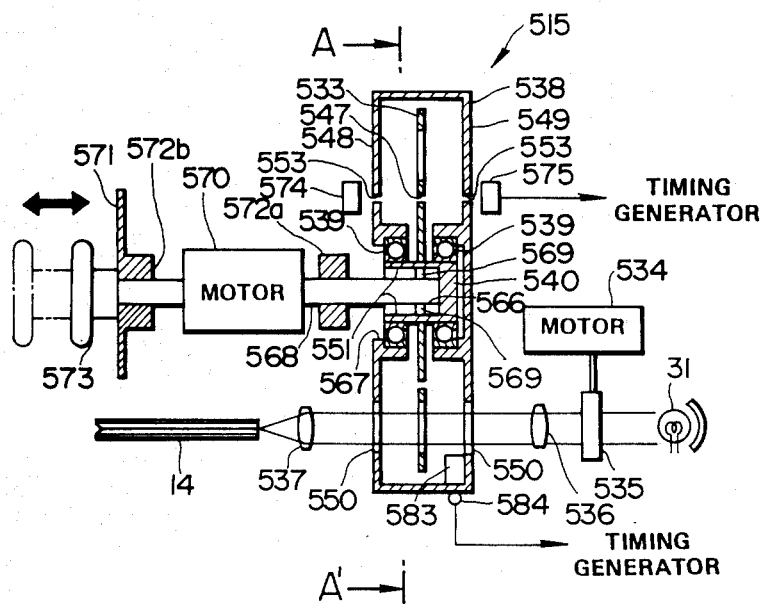

On the other hand, in the light source apparatus 515 contained in the above mentioned imaging apparatus body 511, as shown in FIGS. 58 and 59, a diaphragm 535 driven by a diaphragm motor 534 to adjust the light amount, a condenser lens 536 for condensing the white light entering a rotary filter 533 and a condenser lens 537 making focused and defocused states on the entrance end surface of the light guide 14 are arranged on the light path connecting the light source lamp 31 emitting the white light and the entrance end surface of the light guide 14.

The above mentioned rotary filter 533 is disc-like, has color transmitting filters 532R, 532G and 532B of three primary colors, for example, of R, G and B in the peripheral direction of the plate surface and is provided with a plurality of holes 547 for detecting the timing of reading out the signal of the solid state imaging device in the peripheral direction inside the color transmitting filters 532R, 532G and 532B.

The above mentioned rotary filter 533 is contained in a filter cassette 538 and is provided with a rotary shaft 540 borne by ball bearings 539 provided in the central part of the filter cassette 538 in the rotary center of the rotary filter 533.

Windows 550 are provided through the front plate 548 and back plate 549 of the above mentioned filter cassette 538 so that the white light emitted from the light source lamp 531 may pass through the color transmitting filters 532R, 532G and 532B. Further, windows 553 are provided through the front plate 548 and back plate 549 so as to see the above mentioned timing detecting hole 547. For example, a light emitting device 574 is arranged so as to see the hole 547 from one window 553. For example, a photosensor 575 is provided so as to see the hole 547 from the other window 553.

A hole 566 having groove parts 551 provided in the lengthwise direction is provided on the end surface on the front side of the above mentioned rotary shaft 540. A window 567 is provided in the central part of the front plate 548 so as to see the hole 566.

In the above mentioned hole 566, pins 569 projected in the diametral direction are provided so as to coincide with the above mentioned groove parts 551 and a driving shaft 568 of a rotary filter driving motor 570 supported by a sliding bearing 572a is inserted.

In front of the above mentioned rotary filter driving motor 570, a substantially cylindrical releasably fitting knob 573 passing, for example, through a front plate 576 of the imaging apparatus body 1 and supported by a sliding bearing 572b is provided.

Within the above mentioned filter cassette 538, a filter kind recording part 583 by the combination, for example, of ROM's (read only memories) and contacts for discriminating the kinds of filters is provided and is connected to a contact 584 provided o the side surface of the filter cassette 538.

Figure 60:
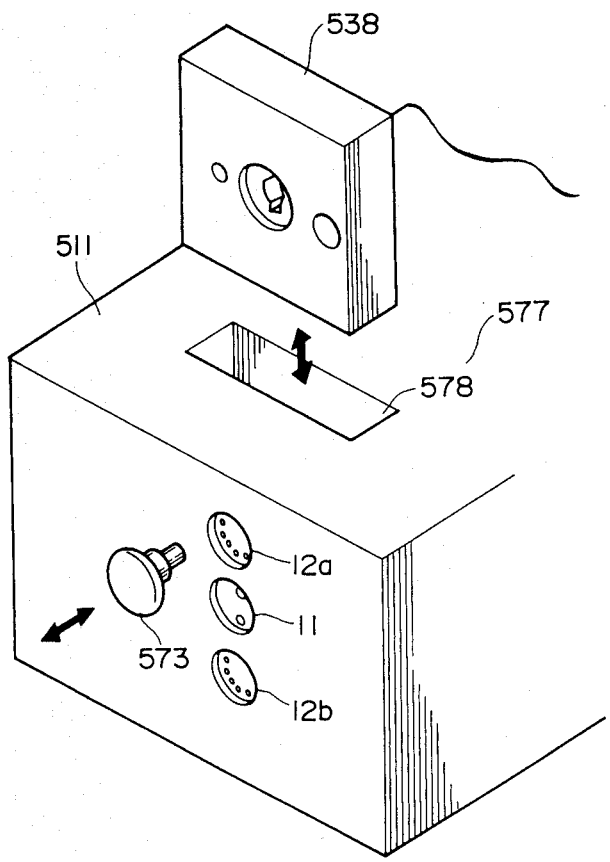

As shown in FIG. 60, the above mentioned filter cassette 583 is inserted through an opening 578 provided in the top plate 577, for example, of the imaging apparatus body 511 and is positioned by positioning pins 579 provided on the bottom surface of the filter cassette 538. After positioning, when the releasably fitting knob 573 is pushed toward the imaging apparatus body 511, the driving shaft 568 of the rotary filter driving motor 570 will be inserted into the hole 566 provided in the rotary shaft 540 supporting the rotary filter 533 and will be connected to transmit the rotation.

The contact 584 of the filter kind recording part 583 will be connected with the timing generator 52a within the imaging apparatus body 511 at the same time as the filter cassette 538 is positioned, the kind and characteristic of the inserted rotary filter 533 will be transmitted to the timing generator 52a and the signal adapted to it can be output to the field sequential type process circuit 41a, mosaic type process circuit 41b, drivers 26a and 26b, output circuit 80 and driver 616.

The above mentioned driver 616 drives the rotary filter driving motor 570 with a synchronous signal adapted to the rotary filter 533 from the timing generator 52a.

The above mentioned position detecting sensor 540 synchronizes the timing of the clock of the timing generator 52a with the rotation of the rotary filter 533 and the output of the timing generator 52a controls the timing of the field sequential type process circuit 41a.

The R, G and B signals from the output circuit 80 are input into an automatic light adjusting circuit 615.

In this automatic light adjusting circuit 615, the diaphragm motor 534 is driven so that the size of the video signal of the object may be fixed and the diaphragm 535 is adjusted.

The color transmitting filters of the rotary filter 533 may be made filters for such special observation as an infrared ray observation as in the thirteenth embodiment. In case a scope or fiber scope provided with a synchronous type imaging means is used as connected to the light source apparatus, it will not be necessary to insert the rotary filter 533 and the white light entering the entrance end surface of the light guide may be defocused by the condenser lens.

In this embodiment, the rotary filter is borne by ball bearings fitted in the central part of the filter cassette but the ball bearings may not be fixed and a resilient member as, for example, a spring may be fixed to the outer ring of the ball bearing to support the rotary filter. When the rotary filter is supported by such resilient member, even in case there is any difference between the axes of the rotary filter driving motor and rotary filter, the difference will be able to be observed by the resilient member.

Thus, according to this embodiment, by fitting and removing the filter cassette 538, different imaging systems, that is, a field sequential type and synchronous type can be accommodated. Also, by replacing the filter cassette 538, ordinary picture images and such special picture images as in the infrared ray band can be obtained.

Figure 61:
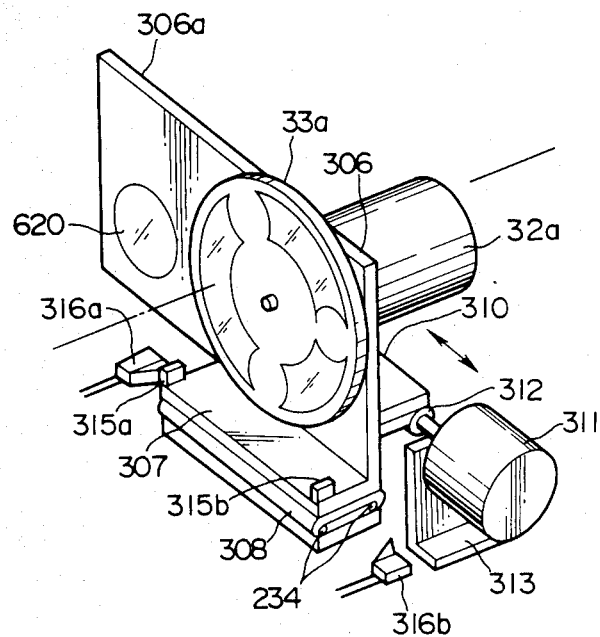
FIGS. 61 and 62 relate to the fifteenth embodiment of the present invention.
Figure 62:
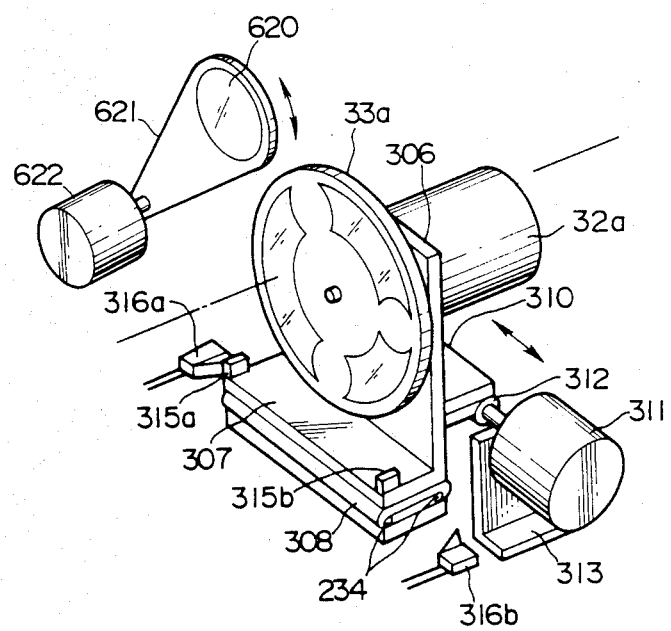

FIGS. 61 and 62 show the fifteenth embodiment of the present invention.

In this embodiment, in a light source apparatus wherein a field sequential light and white light can be output by inserting and removing a rotary filter in and from an illuminating light path as in the fifth, sixth and eighth embodiments, when the rotary filter is retreated from the illuminating light path, a filter for special picture images can be interposed in the illuminating light path.

The light source part shown in FIG. 61 is of substantially the same formation as of the light source part 233 shown in FIG. 33 but the fitting bracket 306 has an extended part 306a extended to the side interposed in the illuminating light path when the rotary filter 33a is retreated from the illuminating light path. In this extended part 306a, a hole is formed in the position interposed in the illuminating light path when the above mentioned rotary filter 33a is retreated from the illuminating light path and a special light filter 620 is fitted in this hole. This special light filter 620 is an infrared ray transmitting filter, ultraviolet ray transmitting filter or specific narrow band transmitting filter.

Thus, in the light source part shown in FIG. 61, when the rotary filter 33a is interposed in the illuminating light path, a field sequential light can be emitted. On the other hand, when the rotary filter 33a is retreated from the illuminating light path, a special light can be emitted. When the object image illuminated by this special light is observed with a synchronous type scope for special picture images, this object image will be made a video signal by the signal process of the synchronous type video processor 25b and the object image by the special light will be quasi-color-displayed. The synchronous type scope for special picture images is of substantially the same formation as of the synchronous type scope for obtaining ordinary color picture images, the color filter array is color-separated into wavelength regions (for example, into an infrared band) for forming special picture images and the solid state imaging device may have a sensitivity in its wavelength region.

In the light source part shown in FIG. 62, a special light filter 620 inserted in and removed from the illuminating light path by a rotary solenoid is further added to the light source part 233 shown in FIG. 33. The above mentioned special light filter 620 is fitted to the expanded diameter side of a substantially fan-shaped fitting bracket 621. The small diameter side end part of the above mentioned fitting bracket 621 is fitted to the output shaft of a gear motor 622. When the above mentioned gear motor 622 is rotated normally and reversely, the fitting bracket 621 and the special light filter 620 fitted to it can be rotated. When the rotary filter 33a is retreated from the illuminating light path, the above mentioned special light filter 620 can be inserted in the illuminating light path.

Thus, in the light source part shown in FIG. 62, when the rotary filter 33a is interposed in the illuminating light path, a field sequential light will be able to be emitted and, when the rotary filter 33a is retreated from the illuminating light path, a white light will be able to be emitted. Further, when the rotary filter 33a is retreated from the illuminating light path and the special light filter 620 is interposed in the illuminating light path, a special light will be able to be emitted.

The other formations, operations and effects are the same as in the fifth, sixth and eighth embodiments.

Figure 63:
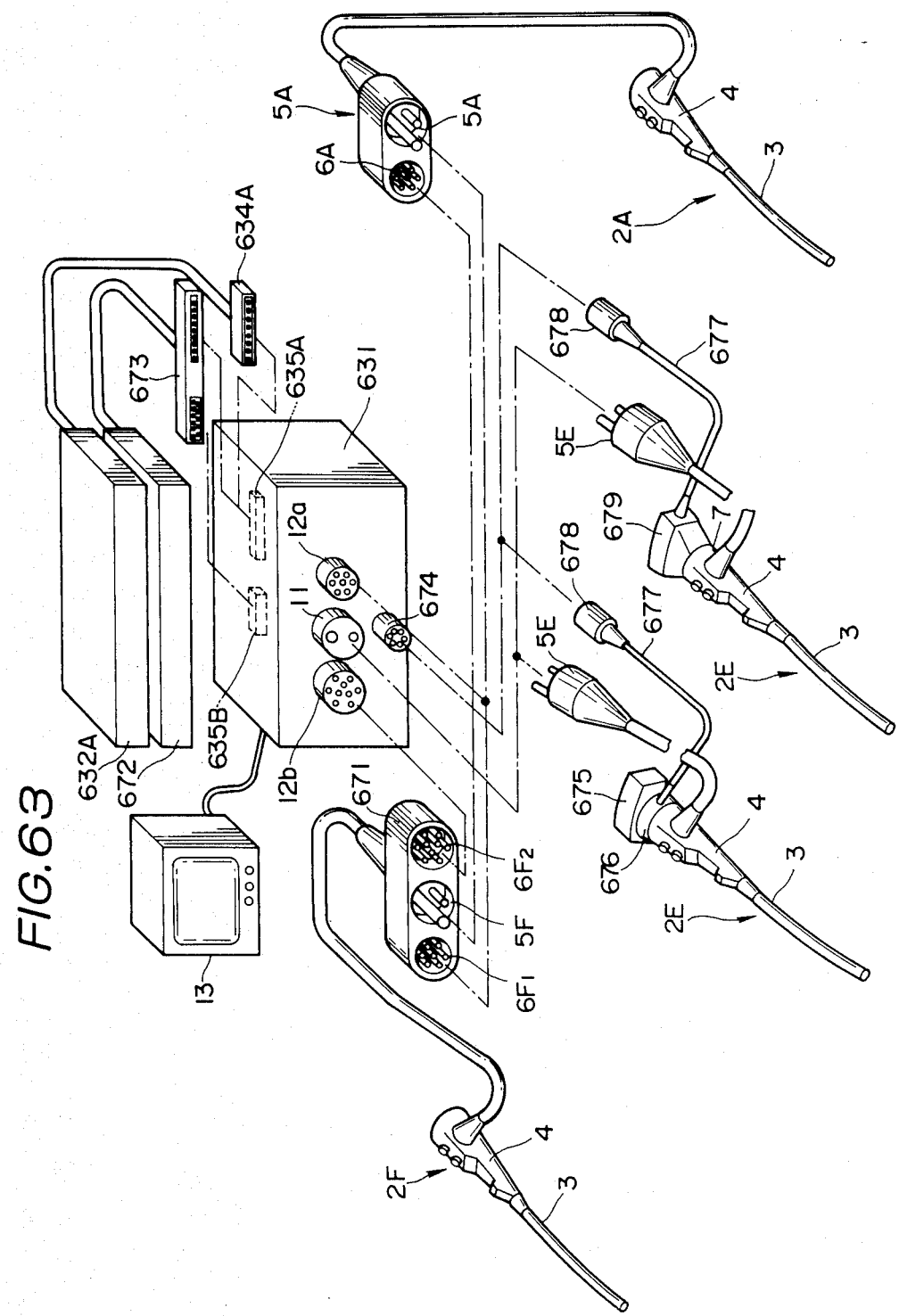
FIG. 63 is a perspective view showing an endoscope apparatus in the sixteenth embodiment.

FIG. 63 shows the sixteenth embodiment of the present invention.

In this embodiment, the light source apparatus 631, field sequential type video processor (abbreviated as VP hereinafter) 632A and synchronous type VP (not illustrated) are made respectively separate.

On the front surface of the above mentioned light source apparatus 631, the same as in the imaging apparatus body 201a shown in FIG. 29, there are provided one light source connector receptacle 11 and two signal connector receptacles 12a and 12b. The field sequential type scopes 2A and 2C (not illustrated) have the light source connector 5A connected to the light source connector receptacle 11 and have the signal connector 6A connected to the signal connector receptacle 12a. In the same manner, the synchronous type scopes 2B and 2D not illustrated have the light source connector 5B connected to the light source connector receptacle 11 and have signal connector 6B connected to the signal connector receptacle 12b.

The above mentioned signal connector receptacles 12a and 12b are connected respectively to the connector receptacles 673A and 673B provided, for example, on the back surface of the above mentioned light source apparatus 631. The connector 364A provided at the end of the signal cable extended out of the field sequential type VP 632A is to be connected to the above mentioned connector receptacle 673A. On the other hand, though not illustrated, the connector provided at the end of the signal cable extended out of the synchronous type VP is to be connected to the above mentioned connector receptacle 635B. A video signal is input from the video processor through the above mentioned connector receptacles 635A and 635B and an object image is to be displayed in the monitor 13 connected to the above mentioned light source apparatus 631.

The synchronous type electronic scope 2F for special picture images is of a solid state imaging device of high pixels or high functions and has a connector 671 integrating two signal connectors 6F1 and 6F2 which can be connected to the above mentioned both signal connector receptacles 12a and 12b and a light source connector 5F which can be connected to the light source connector receptacle 11 in response to the increase of the number of contacts of the signal connectors.

The synchronous type VP 672 processing the signal in response to the synchronous type electronic scope 2F for special picture images has a connector 673 which can be connected at once to both signal connectors 635A and 635B provided on the back side of the light source apparatus 631.

There is considered such mis-connection that the above mentioned connector 671 is connected to the light source apparatus 631 and the field sequential type VP 632A or synchronous type VP (not illustrated) is connected to the light source apparatus 631. However, the scope 2F and VP may be protected by operating a protecting apparatus not illustrated by the discriminating circuit within the light source apparatus 631.

In case the electronic scope 2F is connected to the above mentioned light source apparatus 631, it will be sensed by the discriminating circuit and the contacts of the connector receptacles 12a and 12b will be switched from the ordinary field sequential type and synchronous type process line to the high functional synchronous type process line for special picture images. (In this case, the line of only the field sequential type side may be switched.)

In this embodiment, the light source apparatus 631 is provided with a camera control connector receptacle 674 which is to connect a film camera 675 with a camera control not illustrated provided within the light source apparatus 631 in the case of film photographing with the film camera 675 fitted to the eyepiece part 7 of the fiber scope 2E. In this case, an adapter 676 is held and fitted between the eyepiece part 7 and film camera 675 and the connector 678 of the controller connecting cord 677 extended out of this adapter 676 can be connected.

Conventionally, a contact is in the connecting part of the film camera 675 with the eyepiece part 7 and is connected to a pin provided on the outer periphery of the light source connector 5E and to the controller within the light source apparatus when the light source connector 5E is fitted to the light source connector receptacle 11. This light source connector receptacle 11 does not have its contact receptacle but the adapter 676 is provided with its contact connector 678 and the light source apparatus 631 is provided with the connector receptacle 674 for this connector 678 and therefore even a conventional camera can be used.

Also, the fiber scope 2E fitted with a film camera 679 having a controller connecting cord 677 provided with a connector 678 without interposing the adapter 676 can be used in the same manner. In this case, a contact such as the adapter 676 is provided in the connecting part of the film camera 679 with the eyepiece part 7 and the controller connecting cord 677 may be made detachable from the film camera 679. (Then, the conventional light source can be used for the film camera 679.)

Thus, according to this embodiment, connectors of few contacts can be used as combined without newly providing a connector of many contacts and are therefore advantageous in the space.

Though the progress of the solid state imaging device is fast, even if an endoscope adopting a new device appears, if the number of pixels is below a predetermined number, if a signal processing VP for the new device is pursued, the light source apparatus will be able to be used as it is and the cost to be borne by the users will be low.

In this invention, it is apparent that different working modes in a wide range can be formed on the basis of this invention without deviating from the spirit and scope of the invention. This invention is not restricted by its specific working modes except being limited by the appended claims.

What is claimed is:

1. An endoscope apparatus comprising:
   a plurality of kinds of endoscopes each having
     an elongate insertable part having an illuminating window and observing window in a tip part,
     an illuminating light transmitting means for leading illuminating light to said illuminating window,
     an imaging means for receiving returning light from an object, said returning light entering from said observing window and imaging the object,
     a signal transmitting means connected at one end to said imaging means,
   an illumination connector provided at an entrance side end of said illuminating light transmitting means, and
   a signal connector provided at another end of said signal transmitting means, each endoscope being different in at least one of illuminating method and signal processing system;
   an illuminating means, having an illumination connector receptacle removably connectable with respective illumination connectors of said plurality of endoscopes, for feeding illuminating light to said plurality of endoscopes; and
   a signal processing means, having a signal connector receptacle removably connectable with respective signal connectors of said plurality of endoscopes, for processing signals for said plurality of endoscopes;
   at least one of said illumination connector receptacle and said signal connector receptacle being plural.

2. An endoscope apparatus according to claim 1 wherein said plurality of kinds of endoscopes are endoscopes different from each other in the illuminating method and signal processing system and include a first kind of endoscope provided with a field sequential color imaging means imaging respective images color separated in time series and a second kind of endoscope provided with a synchronous color imaging means having a color-separating means color-separating the image into images of a plurality of wavelength regions.

3. An endoscope apparatus according to claim 2 further comprising a color monitor inputting a video signal from said signal processing means and color-displaying said image.

4. An endoscope apparatus according to claim 2 further comprising a third kind of endoscope comprising an elongate insertable part having an illuminating window and observing window in a tip part, an eyepiece part provided on a rear end side of said insertable part, an illuminating light transmitting means for leading an illuminating light to said illuminating window, an image forming optical system receiving returning light from the object, said returning light entering from the observing window and forming an image, an image transmitting means for transmitting the image formed by said image forming optical system to said eyepiece part and an illumination connector provided at an entrance side end of said illuminating light transmitting means and removably connected to an illumination connector receptacle of said illuminating means.

5. An endoscope apparatus according to claim 4 wherein said first kind of endoscope includes an apparatus comprising said third kind of endoscope and a television camera connected to the eyepiece part of said third kind of endoscope and having an imaging means color-imaging the image as a field sequential image.

6. An endoscope apparatus according to claim 4 wherein said second kind of endoscope includes an apparatus comprising said third kind of endoscope and a television camera connected to the eyepiece of said third kind of endoscope and having an imaging means color-imaging the image as a synchronous image.

7. An endoscope apparatus according to claim 2 wherein both of said illumination connector receptacle and said signal connector receptacle are plural in response to the kind of endoscope.

8. An endoscope apparatus according to claim 2 wherein only said signal connector receptacle is plural in response to the kind of endoscope and said illumination connector receptacle is a single receptacle.

9. An endoscope apparatus according to claim 2 wherein only said illumination connector receptacle is plural in response to the kind of endoscope and said signal connector receptacle is a single receptacle.

10. An endoscope apparatus according to claim 2 wherein said illuminating means and said signal processing means are made integral.

11. An endoscope apparatus according to claim 2 wherein said illuminating means and said signal processing means are made separate.

12. An endoscope apparatus according to claim 11 wherein said signal processing means comprises a first signal processing apparatus processing signals for said first kind of endoscope and a second kind of signal processing apparatus processing signals for said second endoscope.

13. An endoscope apparatus according to claim 11 wherein said illuminating means comprises a first light source apparatus feeding an illuminating light to said first kind of endoscope and a second light source apparatus feeding an illuminating light to said second kind of endoscope and said first and second light source apparatuses are made separate from each other.

14. An endoscope apparatus according to claim 2 wherein at least one of said first kind of endoscope and second kind of endoscope has a discriminating information generating means for generating information distinguishing an image system and said signal processing means has a discriminating means inputting information from said discriminating information generating means and distinguishing the imaging system of a connected endoscope.

15. An endoscope apparatus according to claim 14 further comprising a warning means for warning when a different kind of endoscope is connected to an illumination connector receptacle and signal connector receptacle based upon output of said discriminating means.

16. An endoscope according to claim 14 wherein said illuminating means has an illumination connector receptacle commonly used by the first kind of endoscope and second kind of endoscope and a light source apparatus which can switch and output a field sequential light and white light to said illumination connector receptacle.

17. An endoscope apparatus according to claim 16 wherein said light source apparatus is to switch a field sequential light and white light based upon output of said discriminating means.

18. An endoscope apparatus according to claim 14 wherein said signal processing means has a signal connector receptacle commonly used by said first kind of endoscope and second kind of endoscope, a field sequential signal processing means, a synchronous signal processing means and a switching means selectively connecting one of said field sequential signal processing means and synchronous signal processing means with said signal connector receptacle.

19. An endoscope apparatus according to claim 18 wherein said switching means selects one of the signal processing means for the imaging system of a connected endoscope based upon output of said discriminating means.

20. An endoscope apparatus according to claim 1 wherein said plurality of kinds of endoscopes are endoscopes different from each other in the illuminating method and include a fourth kind of endoscope for observing an object image in a visible band and a fifth kind of endoscope for observing an object image in a specific wavelength region.

21. An endoscope apparatus according to claim 20 wherein said fourth kind of endoscope and fifth kind of endoscope are provided respectively with field sequential imaging means and said illuminating means is provided with an illumination connector receptacle for the fourth kind of endoscope, a light source apparatus outputting to the illumination connector receptacle a field sequential light by a combination of three different wavelength regions in the visible band, an illumination connector receptacle for the fifth kind of endoscope and a light source apparatus outputting to the illumination connector receptacle a field sequential light by a combination of specific wavelength regions.

22. An endoscope apparatus according to claim 20 wherein said fourth kind of endoscope and fifth kind of endoscope are provided respectively with a field sequential imaging means and said illuminating means is provided with an illumination connector receptacle commonly used by the fourth kind of endoscope and fifth kind of endoscope and a light source apparatus which can switch and output to the illumination connector receptacle a field sequential light by a combination of three different wavelength regions in the visible band and a field sequential light by a combination of specific wavelength regions.

23. An endoscope apparatus according to claim 22 wherein said light source apparatus is provided with a lamp, a rotary filter alternately insertable into an illuminating light path between said lamp and said illumination connector receptacle and separating in time series light of said lamp into three different wavelength regions in the visible band and a rotary filter separating in time series light of said lamp into a plurality of specific wavelength regions.

24. An endoscope apparatus according to claim 20 wherein said fourth kind of endoscope is provided with a field sequential imaging means, said fifth kind of endoscope is provided with a synchronous imaging means and said illuminating means is provided with an illumination connector receptacle commonly used by the fourth kind of endoscope and fifth kind of endoscope and a light source apparatus which can switch and output to said illumination connector receptacle a field sequential light by a combination of three different wavelength regions in the visible band and a light including a specific wavelength region color-separated by said fifth kind of endoscope.

25. An endoscope apparatus according to claim 24 wherein said light source apparatus is provided with a lamp, a rotary filter alternatively insertable into an illuminating light path between said lamp and said illumination connector receptacle and separating in time series light of said lamp into three different wavelength regions in the visible band and a filter limited to a light including a specific wavelength region color-separated by said fifth kind endoscope.

26. An endoscope apparatus comprising:
a plurality of kinds of endoscopes each having,
an elongated insertable part having an illuminating window and an observing window in a tip part,
an illuminating light transmitting means for leading an illuminating light to said illuminating window,
an imaging means for receiving returning light from an object, said returning light entering from said observing window and imaging the object,
a signal transmitting means connected at one end to said imaging means,
an illumination connector provided at an entrance side of said illuminating light transmitting means, and a signal connector provided at another end of said signal transmitting means, each endoscope being different in at least one of illuminating method and signal processing system;

an illuminating means, having an illumination connector receptacle removably connectable with respective illumination connectors of said plurality of endoscopes, for feeding illuminating light to said plurality of endoscopes; and a signal processing means, having a signal connector receptacle connectable with respective signal connectors of said plurality of endoscopes, for processing signals for said plurality of endoscopes;

at least one of said illumination connector receptacle and said signal connector receptacle being plural;

said illumination connector and said signal connector of one endoscope being made integral; and said illumination connector receptacle and said signal connector receptacle being provided adjacent to each other so as to be connectable to respective connectors of said endoscope.

27. An endoscope apparatus according to claim 26, wherein said illuminating means and said signal processing means are provided with one illumination connector receptacle connectable to said plurality of kinds of endoscopes, and different kinds of signal connector receptacles are provided at both ends of the illumination connector receptacle.

28. An endoscope apparatus according to claim 26, wherein said illuminating means and said signal processing means are provided with one signal connector receptacle connectable to said plurality of kinds of endoscopes and different kinds of illumination connector receptacles are provided at both ends of the signal connector receptacle.

29. An endoscope apparatus according to claim 26, wherein said illuminating means and said signal processing means are divided into separate units, said illumination connector receptacle and said signal connector receptacle being provided adjacent to each other so as to be connectable to said illumination connector and said signal connector of said endoscope which are made integral, when the separate units are placed side by side.

30. An endoscope apparatus comprising:

a plurality of kinds of endoscopes each having, an elongated insertable part having an illuminating window and an observing window in a tip part, an illuminating light transmitting means for leading an illuminating light to said illuminating window, an imaging means for receiving returning light from an object, said returning light entering from said observing window and imaging the object, a signal transmitting means connected at one end to said imaging means, an illumination connector provided at an entrance side of said illuminating light transmitting means, and a signal connector provided at another end of said signal transmitting means, each endoscope being different in at least one of illuminating method and signal processing system;

an illumination means, having an illumination connector receptacle removably connectable with respective illumination connectors of said plurality of endoscopes, and a signal connector receptacle removably connectable with respective signal connectors, for feeding illuminating light to said plurality of endoscopes; and a signal processing means for processing signals for said plurality of endoscopes;

said illumination means being provided with an electrical connecting means for connecting said illuminating means with said signal processing means, for feeding signals from said signal connector receptacle to said signal processing means located in a separate unit;

at least one of said illumination connector receptacle and said signal connector receptacle being plural.

31. An endoscope apparatus according to claim 30, wherein said illumination connector and said signal connector of one endoscope are made integral; and said illumination connector receptacle and said signal connector receptacle of one endoscope being provided adjacent to each other so as to be connectable to respective connectors of said endoscope.

32. An endoscope apparatus according to claim 30 wherein said plurality of kinds of endoscopes include a first kind of endoscope provided with a field sequential color imaging means for imaging respective images color-separating in time series, a second kind of endoscope provided with a synchronous color imaging means having a color separating means for color-separating an image into images of a plurality of wavelength regions and a fifth kind of endoscope for observing an image of a specific wavelength region.

33. An endoscope apparatus according to claim 32 wherein only said signal connector receptacle is plural in response to an imaging system of the imaging means and said illumination connector receptacle is a single receptacle.

34. An endoscope apparatus according to claim 33 wherein only said signal connector receptacles is plural in response to the imaging system of the imaging means, said illumination connector receptacle is single and said fifth kind of endoscope has a plurality of signal connectors to be connected to a plurality of signal connector receptacles provided in response to the imaging system.

* * * * *

UNITED STATES PATENT AND TRADEMARK OFFICE
CERTIFICATE OF CORRECTION

PATENT NO. : 4,860,094

DATED : August 22, 1989

INVENTOR(S) : HIBINO et al

It is certified that error appears in the above-identified patent and that said Letters Patent is hereby corrected as shown below:

On the cover page, Item [75], "Kenji Kumura" should read
--Kenji Kimura--.

Signed and Sealed this

Second Day of October, 1990

Attest:

HARRY F. MANBECK, JR.

*Attesting Officer*   *Commissioner of Patents and Trademarks*